US012534521B2

(12) United States Patent
Zhu et al.

(10) Patent No.: US 12,534,521 B2
(45) Date of Patent: Jan. 27, 2026

(54) ANTIBODIES SPECIFICALLY RECOGNIZING C5A AND USES THEREOF

(71) Applicant: STAIDSON (BEIJING) BIOPHARMACEUTICALS CO., LTD., Beijing (CN)

(72) Inventors: Pingxia Zhu, Beijing (CN); Zhong Li, Beijing (CN)

(73) Assignee: STAIDSON (BEIJING) BIOPHARMACEUTICALS CO., LTD., Beijing (CN)

( * ) Notice: Subject to any disclaimer, the term of this patent is extended or adjusted under 35 U.S.C. 154(b) by 559 days.

(21) Appl. No.: 18/012,580

(22) PCT Filed: Jun. 18, 2021

(86) PCT No.: PCT/CN2021/100863

§ 371 (c)(1),
(2) Date: Dec. 22, 2022

(87) PCT Pub. No.: WO2021/259160

PCT Pub. Date: Dec. 30, 2021

(65) Prior Publication Data

US 2023/0257454 A1 Aug. 17, 2023

Related U.S. Application Data

(63) Continuation of application No. PCT/CN2020/098081, filed on Jun. 24, 2020.

(51) Int. Cl.
*C07K 16/18* (2006.01)
*A61K 39/00* (2006.01)
*A61P 11/00* (2006.01)
*C12N 15/63* (2006.01)

(52) U.S. Cl.
CPC .............. *C07K 16/18* (2013.01); *A61P 11/00* (2018.01); *C12N 15/63* (2013.01); *A61K 2039/505* (2013.01); *C07K 2317/622* (2013.01); *C07K 2317/76* (2013.01)

(58) Field of Classification Search
None
See application file for complete search history.

(56) References Cited

U.S. PATENT DOCUMENTS

2017/0002067 A1 1/2017 Guo et al.

FOREIGN PATENT DOCUMENTS

| | | | | |
|---|---|---|---|---|
| CN | 103201289 | A | 7/2013 | |
| CN | 105963694 | A | 9/2016 | |
| CN | 107207607 | A | 9/2017 | |
| CN | 111201241 | A | 5/2020 | |
| EP | 2327725 | A1 | 6/2011 | |
| JP | 2013512209 | A | 4/2013 | |
| TW | 201904611 | A | 2/2019 | |
| WO | 2011137395 | A1 | 11/2011 | |
| WO | WO-2012088247 | A2 * | 6/2012 | ............. C07K 16/18 |
| WO | 2018234118 | A1 | 12/2018 | |

OTHER PUBLICATIONS

Chen Chen, LV et al. 2015. "Role of C5a in inflammatory reaction and development of anti-C5a antibody drugs." Chin J Biologicals, vol. 28 No. 5.
International Search Report and Written Opinion issued in counterpart PCT Application No. PCT/CN2021/100863 dated Sep. 16, 2021 (six (6) pages).
Chinese-language Notice to Grant for CN Appl. No. 202180001665.2 dated May 22, 2024 with English translation (three (3) pages).
Japanese-language Notice to Grant for JP Appl. No. 2022580950 dated Dec. 17, 2024 with English translation (eight (8) pages).
The magazine of Okayama Medical Association, 2009, vol. 121, pp. 119-122. History and Production Technology of Antibody Drugs. Hidenori Wake.
Johnson R Jet al. 1987. "Identification of an Antigenic Epitope and Receptor Binding Domain of Human C5A", the Journal of Immunology, Williams & Wilkins Co, US, vol. 138, No. 11, pp. 3856-3862.
Extended European Search Report issued in counterpart EP Application No. 21829626.7 dated Oct. 1, 2024 (ten (10) pages).

* cited by examiner

*Primary Examiner* — Anne M. Gussow
*Assistant Examiner* — Brianna K Swartwout
(74) *Attorney, Agent, or Firm* — David S. Bradin; Maynard Nexsen PC

(57) ABSTRACT

The present application provides antibodies including antigen-binding fragments thereof that specifically recognizing Complement component 5a (C5a). Also provided are methods of making and using these antibodies.

11 Claims, 14 Drawing Sheets

Specification includes a Sequence Listing.

ANTIBODIES SPECIFICALLY RECOGNIZING C5A AND USES THEREOF

CROSS REFERENCE TO RELATED APPLICATIONS

This is a national stage application filed under 37 U.S.C. 371 based on International Patent Application No. PCT/CN2021/100863, filed Jun. 18, 2021, which claims priority to International Patent Application No. PCT/CN2020/098081, filed Jun. 24, 2020, the disclosures of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 202006095269_SEQLIST.txt, date recorded: Jun. 10, 2020, size: 96.5 KB).

TECHNICAL FIELD

This application pertains to antibodies that specifically recognize complement component 5a (C5a), and methods of manufacture and uses thereof, including methods of treating autoimmune and/or inflammatory conditions and/or cancer and/or pain and/or transplantation.

BACKGROUND

C5a is cleaved from complement component C5 by C5-convertase in the complement cascade, and it is an active peptide in anaphylactic reactions and inflammatory processes. C5a stimulates mast cell degranulation, stimulates the release of tumor necrosis factor-α (TNF-α) and histamine, and recruits phagocytes to sites of infection and inflammation by increasing adhesion molecule expression on the surface of endothelial cells (Mollnes, T. E. et al. Blood 2002, 100, 1869-1877; Riedemann, N.C. et al. Immunity 2003, 19, 193-202). C5a also increases vascular permeability in some pathological stimuli, such as allograft rejection after transplantation and asthma (Gueler, F. et al. J. Am. Soc. Nephrol. 2008, 19, 2302-2312; Krug, N. et al. Am. J. Respir. Crit. Care Med. 2001, 164, 1841-1843; Khan, M. A. et al. Proc. Natl. Acad. Sci. USA 2013, 110, 6061-6066). The serum level of C5a has been discussed in several studies. In a study by Lechner et al., the C5a level was 8.34+2.05 (ng/mL) in the control group (Lechner, J. et al. Immun. Ageing 2016, 13, 4). Under normal conditions, the plasma C5a level is quite low because of the rapid clearance of anaphylatoxin (Oppermann, M. et al. Immunology 1994, 82, 516-521). In murine cortical tubular cells, after treatment with C5a (25 nM), transforming growth factor-β (TGF-β) was elevated which has been shown to lead to renal fibrosis and renal scar formation (Boor, P. et al. J. Am. Soc. Nephrol. 2007, 18, 1508-1515).

C5a is a potent proinflammatory molecule which binds to C5aRI (CD88), a classical G protein-coupled receptor (GPCR), and elicits the signaling pathways of proinflammatory responses (Li, R. et al. FASEB J. 2013, 27, 855-864). C5aR is expressed in different non-myeloid cells, such as human umbilical vascular endothelial cells (HUVEC), murine dermal, liver, pulmonary and renal proximal tubules (Monsinjon, T. et al. FASEB J. 2003, 17, 1003-1014; Gerard, C. et al. Annu. Rev. Immunol. 1994, 12, 775-808; Haviland, D. L. et al. J. Immunol. 1995, 154, 1861-1869). Also, it was demonstrated that C5aR was expressed in glomerular endothelial cells but not in podocytes, indicating that C5a may cause proteinuria on the primary target of renal endothelial cells (Tsai, I. J. et al. Cell. Mol. Life Sci. 2015, 72, 3157-3171).

Neutralization of C5a binding to C5aR is therefore a therapeutic approach to treating diseases and conditions mediated through C5a. An antibody against human C5a, designated INab308 (InflaRx), was described in WO2011063980. Other C5a antibodies such as MEDI-7814 (MedImmune) was described in WO2012088247, and BNJ383 (Alexion) was described in U.S. Ser. No. 10/450,370.

The disclosures of all publications, patents, patent applications and published patent applications referred to herein are hereby incorporated herein by reference in their entirety.

SUMMARY

In one aspect, the present application provides an isolated anti-C5a antibody that specifically binds to an epitope on human C5a, wherein the isolated anti-C5a antibody specifically binds to at least one amino acid residue selected from residue D at position 31, residue E at position 32 and residue R at position 40 of human C5a as shown in SEQ ID NO: 141. In some embodiments, the isolated anti-C5a antibody specifically binds to residues 31-40 of human C5a as shown in SEQ ID NO: 141. In some embodiments, the isolated anti-C5a antibody that specifically binds to an epitope within, consisting of or comprising the sequence as follows: (i) DGACVNNDETCEQRAARISLGPR (SEQ ID NO: 145), (ii) NDETCEQRAARISLGPR (SEQ ID NO: 146), or (iii) DETCEQRAAR (SEQ ID NO: 147). In some embodiments, the isolated anti-C5a antibody that specifically binds to a peptide consisting of or comprising the sequence as follows: (i) DGACVNNDETCEQRAARISLGPR (SEQ ID NO: 145), (ii) NDETCEQRAARISLGPR (SEQ ID NO: 146), or (iii) DETCEQRAAR (SEQ ID NO: 147). In some embodiments, the isolated anti-C5a antibody binds to the human C5a with a Kd from about 0.1 pM to about 1 nM. In some embodiments, the isolated anti-C5a antibody binds to free human C5a polypeptide in the presence of a 2-fold or more molar excess of uncleaved, native human C5.

In some embodiments according to any one of the isolated anti-C5a antibodies described above, the isolated anti-C5a antibody comprises: a heavy chain variable domain ($V_H$) comprising a heavy chain complementarity determining region HC-CDR1 comprising $X_1YYX_2Q$ (SEQ ID NO: 67), wherein $X_1$ is D, or N, and $X_2$ is M, or I; an HC-CDR2 comprising $LIRX_1KX_2X_3GX_4TX_5X_6X_7AASX_8KG$ (SEQ ID NO: 68), wherein $X_1$ is K, or N, $X_2$ is A, or V, $X_3$ is V, N, or I, $X_4$ is G, E, F, H, I, Q, or R, $X_5$ is T, V, or A, $X_6$ is Q, E, T, or S, $X_7$ is Y or F, and $X_8$ is V or L; and an HC-CDR3 comprising $RX_1GPPGLX_2$ (SEQ ID NO: 69), wherein $X_1$ is A, L, or V, and $X_2$ is T, S, or A; and a light chain variable domain ($V_L$) comprising a light chain complementarity determining region (LC-CDR) 1 comprising $RSSQX_1LLX_2X_3X_4X_5YX_6YX_7D$ (SEQ ID NO: 70), wherein $X_1$ is S, R, or N, $X_2$ is A, H, or D, $X_3$ is S or T, $X_4$ is D or N, $X_6$ is G, A, or R, $X_6$ is N, I, T, E, or A, and $X_7$ is I, M, L, or V; a LC-CDR2 comprising $GX_1SX_2RAS$ (SEQ ID NO: 71), wherein $X_1$ is G or A, $X_2$ is N or K; and a LC-CDR3 comprising $X_1QHX_2X_3LPX_4T$ (SEQ ID NO: 72), wherein $X_1$ is L or M, $X_2$ is R or K, $X_3$ is A or V, and $X_4$ is P, or L.

In some embodiments, there is provided an isolated anti-C5a antibody comprises: a $V_H$ comprising an HC-CDR1 comprising an amino acid sequence having at least about 90% sequence identify with any one of SEQ ID NOs: 1-6; an HC-CDR2 comprising an amino acid sequence having at least about 90% sequence identify with any one of SEQ ID NOs: 7-29; and an HC-CDR3 comprising an amino acid sequence having at least about 90% sequence identify with any one of SEQ ID NOs: 30-38; and a $V_L$ comprising a LC-CDR1 comprising an amino acid sequence having at least about 90% sequence identify with any one of SEQ ID NOs: 39-56; a LC-CDR2 comprising an amino acid sequence having at least about 90% sequence identify with any one of SEQ ID NOs: 57-59; and a LC-CDR3 comprising an amino acid sequence having at least about 90% sequence identify with any one of SEQ ID NOs: 60-66.

In some embodiments, there is provided an isolated anti-C5a antibody comprising a $V_H$ comprising an HC-CDR1, an HC-CDR2, and an HC-CDR3 of a $V_H$ comprising the amino acid sequence of any one of SEQ ID NOs: 73-111; and a $V_L$ comprising an LC-CDR1, an LC-CDR2, and an LC-CDR3 of a $V_L$ comprising the amino acid sequence of any one of SEQ ID NOs: 112-140.

In some embodiments, there is provided an isolated anti-C5a antibody comprises: (i) a $V_H$ comprising an HC-CDR1 comprising an amino acid sequence having at least about 90% sequence identify with SEQ ID NO: 1, an HC-CDR2 comprising an amino acid sequence having at least about 90% sequence identify with SEQ ID NO: 7, and an HC-CDR3 comprising an amino acid sequence having at least about 90% sequence identify with SEQ ID NO: 30; and a $V_L$ comprising an LC-CDR1 comprising an amino acid sequence having at least about 90% sequence identify with SEQ ID NO: 39, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 60; (ii) a $V_H$ comprising an HC-CDR1 comprising an amino acid sequence having at least about 90% sequence identify with SEQ ID NO: 2, an HC-CDR2 comprising an amino acid sequence having at least about 90% sequence identify with SEQ ID NO: 8, and an HC-CDR3 comprising an amino acid sequence having at least about 90% sequence identify with SEQ ID NO: 31; and a $V_L$ comprising an LC-CDR1 comprising an amino acid sequence having at least about 90% sequence identify with SEQ ID NO: 40, an LC-CDR2 comprising an amino acid sequence having at least about 90% sequence identify with SEQ ID NO: 57, and an LC-CDR3 comprising an amino acid sequence of SEQ ID NO: 61; (iii) a $V_H$ comprising an HC-CDR1 comprising an amino acid sequence having at least about 90% sequence identify with SEQ ID NO: 2, an HC-CDR2 comprising an amino acid sequence having at least about 90% sequence identify with SEQ ID NO: 10, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 42, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61; (iv) a $V_H$ comprising an HC-CDR1 comprising an amino acid sequence having at least about 90% sequence identify with SEQ ID NO: 2, an HC-CDR2 comprising an amino acid sequence having at least about 90% sequence identify with SEQ ID NO: 11, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 41, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 64 (v) a $V_H$ comprising an HC-CDR1 comprising an amino acid sequence having at least about 90% sequence identify with SEQ ID NO: 2, an HC-CDR2 comprising an amino acid sequence having at least about 90% sequence identify with SEQ ID NO: 9, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 43, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 63; (vi) a $V_H$ comprising an HC-CDR1 comprising an amino acid sequence having at least about 90% sequence identify with SEQ ID NO: 2, an HC-CDR2 comprising an amino acid sequence having at least about 90% sequence identify with SEQ ID NO: 11, and an HC-CDR3 comprising an amino acid sequence having at least about 90% sequence identify with SEQ ID NO: 35; and a $V_L$ comprising an LC-CDR1 comprising an amino acid sequence having at least about 90% sequence identify with SEQ ID NO: 44, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 60; (vii) a $V_H$ comprising an HC-CDR1 comprising an amino acid sequence having at least about 90% sequence identify with SEQ ID NO: 6, an HC-CDR2 comprising an amino acid sequence having at least about 90% sequence identify with SEQ ID NO: 18, and an HC-CDR3 comprising an amino acid sequence having at least about 90% sequence identify with SEQ ID NO: 36; and a $V_L$ comprising an LC-CDR1 comprising an amino acid sequence having at least about 90% sequence identify with SEQ ID NO: 42, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61; (viii) a $V_H$ comprising an HC-CDR1 comprising an amino acid sequence having at least about 90% sequence identify with SEQ ID NO: 5, an HC-CDR2 comprising an amino acid sequence having at least about 90% sequence identify with SEQ ID NO: 21, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 42, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61; (ix) a $V_H$ comprising an HC-CDR1 comprising an amino acid sequence having at least about 90% sequence identify with SEQ ID NO: 2, an HC-CDR2 comprising an amino acid sequence having at least about 90% sequence identify with SEQ ID NO: 10, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 53, an LC-CDR2 comprising an amino acid sequence having at least about 90% sequence identify with SEQ ID NO: 59, and an LC-CDR3 comprising an amino acid sequence having at least about 90% sequence identify with SEQ ID NO: 65; (x) a $V_H$ comprising an HC-CDR1 comprising an amino acid sequence having at least about 90% sequence identify with SEQ ID NO: 2, an HC-CDR2 comprising an amino acid sequence having at least about 90% sequence identify with SEQ ID NO: 23, and an HC-CDR3 comprising an amino acid sequence having at least about 90% sequence identify with SEQ ID NO: 32; and a $V_L$ comprising an LC-CDR1 comprising the amino acid sequence having at least about 90% sequence identify with SEQ ID NO: 42, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61; (xi) a $V_H$ comprising an HC-CDR1 comprising an amino acid sequence having at least about 90% sequence identify with SEQ ID NO: 2, an HC-CDR2 comprising an amino acid sequence having at least about 90% sequence identify with SEQ ID NO: 23, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 56, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61; (xii) a $V_H$ comprising an HC-CDR1 comprising an amino acid sequence having at least about 90% sequence identify with SEQ ID NO: 6, an HC-CDR2 comprising an amino acid sequence having at least about 90% sequence identify with SEQ ID NO: 18, and an HC-CDR3 comprising an amino acid sequence having at least about 90% sequence identify with SEQ ID NO: 36; and a $V_L$ comprising an LC-CDR1 comprising an amino acid sequence having at least about 90% sequence identify with SEQ ID NO: 52, an LC-CDR2 comprising an amino acid sequence having at least about 90% sequence identify with SEQ ID NO: 58, and an LC-CDR3 comprising an amino acid sequence having at least about 90% sequence identify with SEQ ID NO: 61; (xiii) a $V_H$ comprising an HC-CDR1 comprising an amino acid sequence having at least about 90% sequence identify with SEQ ID NO: 6, an HC-CDR2 comprising an amino acid sequence having at least about 90% sequence identify with SEQ ID NO: 18, and an HC-CDR3 comprising an amino acid sequence having at least about 90% sequence identify with SEQ ID NO: 36; and a $V_L$ comprising an LC-CDR1 comprising an amino acid sequence having at least about 90% sequence identify with SEQ ID NO: 53, an LC-CDR2 comprising an amino acid sequence having at least about 90% sequence identify with SEQ ID NO: 59, and an LC-CDR3 comprising an amino acid sequence having at least about 90% sequence identify with SEQ ID NO: 65; (xiv) a $V_H$ comprising an HC-CDR1 comprising an amino acid sequence having at least about 90% sequence identify with SEQ ID NO: 5, an HC-CDR2 comprising an amino acid sequence having at least about 90% sequence identify with SEQ ID NO: 21, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 52, an LC-CDR2 comprising an amino acid sequence having at least about 90% sequence identify with SEQ ID NO: 58, and an LC-CDR3 comprising an amino acid sequence having at least about 90% sequence identify with SEQ ID NO: 61; or (xv) a $V_H$ comprising an HC-CDR1 comprising an amino acid sequence having at least about 90% sequence identify with SEQ ID NO: 5, an HC-CDR2 comprising an amino acid sequence having at least about 90% sequence identify with SEQ ID NO: 21, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 53, an LC-CDR2 comprising an amino acid sequence having at least about 90% sequence identify with SEQ ID NO: 59, and an LC-CDR3 comprising an amino acid sequence having at least about 90% sequence identify with SEQ ID NO: 65.

In some embodiments, according to anyone of the isolated anti-C5a antibodies described above, the isolated anti-C5a antibody comprises: a $V_H$ comprising an amino acid sequence having at least about 90% sequence identify with any one of SEQ ID NOs: 73-111; and a $V_L$ comprising an amino acid sequence having at least about 90% sequence identify with any one of SEQ ID NOs: 112-140. In some embodiments, the isolated anti-C5a antibody comprises: (i) a $V_H$ comprising the amino acid sequence of SEQ ID NO: 73; and a $V_L$ comprising the amino acid sequence of SEQ ID NO: 112; (ii) a $V_H$ comprising the amino acid sequence of SEQ ID NO: 75; and a $V_L$ comprising the amino acid sequence of SEQ ID NO: 114; (iii) a $V_H$ comprising the amino acid sequence of SEQ ID NO: 100; and a $V_L$ comprising the amino acid sequence of SEQ ID NO: 135; (iv) a $V_H$ comprising the amino acid sequence of SEQ ID NO: 79; and a $V_L$ comprising the amino acid sequence of SEQ ID NO: 118; (v) a $V_H$ comprising the amino acid sequence of SEQ ID NO: 85; and a $V_L$ comprising the amino acid sequence of SEQ ID NO: 117; (vi) a $V_H$ comprising the amino acid sequence of SEQ ID NO: 88; and a $V_L$ comprising the amino acid sequence of SEQ ID NO: 126; (vii) a $V_H$ comprising the amino acid sequence of SEQ ID NO: 93; and a $V_L$ comprising the amino acid sequence of SEQ ID NO: 116; (viii) a $V_H$ comprising the amino acid sequence of SEQ ID NO: 97; and a $V_L$ comprising the amino acid sequence of SEQ ID NO: 116; (ix) a $V_H$ comprising the amino acid sequence of SEQ ID NO: 77; and a $V_L$ comprising the amino acid sequence of SEQ ID NO: 132; (x) a $V_H$ comprising the amino acid sequence of SEQ ID NO: 102; and a $V_L$ comprising the amino acid sequence of SEQ ID NO: 135; (xi) a $V_H$ comprising the amino acid sequence of SEQ ID NO: 109; and a $V_L$ comprising the amino acid sequence of SEQ ID NO: 138; (xii) a $V_H$ comprising the amino acid sequence of SEQ ID NO: 110; and a $V_L$ comprising the amino acid sequence of SEQ ID NO: 139; (xiii) a $V_H$ comprising the amino acid sequence of SEQ ID NO: 110; and a $V_L$ comprising the amino acid sequence of SEQ ID NO: 140; (xiv) a $V_H$ comprising the amino acid sequence of SEQ ID NO: 111; and a $V_L$ comprising the amino acid sequence of SEQ ID NO: 139; or (xv) a $V_H$ comprising the amino acid sequence of SEQ ID NO: 111; and a $V_L$ comprising the amino acid sequence of SEQ ID NO: 140.

In some embodiments, there is provided an isolated anti-C5a antibody that specifically binds to C5a competitively with any one of the isolated anti-C5a antibodies described above. In some embodiments, there is provided an isolated anti-C5a antibody that specifically binds to the same epitope as any one of isolated anti-C5a antibodies described above.

In some embodiments according to any of the isolated anti-C5a antibodies described above, the isolated anti-C5a antibody comprises an Fc fragment. In some embodiments, the isolated anti-C5a antibody is a full-length IgG antibody. In some embodiments, the isolated anti-C5a antibody is a full-length IgG1 or IgG4 antibody. In some embodiments, the anti-C5a antibody is chimeric, human, or humanized. In some embodiments, the anti-C5a antibody is an antigen binding fragment selected from the group consisting of a Fab, a Fab', a F(ab)'2, a Fab'-SH, a single-chain Fv (scFv), an Fv fragment, a dAb, a Fd, a nanobody, a diabody, and a linear antibody.

In some embodiments, there is provided isolated nucleic acid molecule(s) that encodes any one of the anti-C5a antibodies described above. In some embodiments, there is provided a vector comprising any one of the nucleic acid molecules described above. In some embodiments, there is provided a host cell comprising any one of the anti-C5a antibodies described above, any one of the nucleic acid molecules described above, or any one of the vectors described above. In some embodiments, there is provided a method of producing an anti-C5a antibody, comprising: a) culturing any one of the host cells described above under conditions effective to express the anti-C5a antibody; and b) obtaining the expressed anti-C5a antibody from the host cell.

In some embodiments, there is provided a method of treating a disease or condition in an individual in need thereof, comprising administering to the individual an effective amount of any one of the anti-C5a antibodies described above. In some embodiments, use of any one of the anti-C5a antibodies described above, or a pharmaceutical composition comprising an anti-C5a antibody in the manufacture of a medicament for treating a disease or condition. In some embodiments, the disease or condition is an inflammatory, respiratory or autoimmune disease or condition. In some embodiments, the disease or condition is selected from the group consisting of inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer.

Also provided are pharmaceutical compositions, kits and articles of manufacture comprising any one of the anti-C5a antibodies described above.

BRIEF DESCRIPTION OF DRAWINGS

FIG. 1A shows the binding curve of Cab01, Cab03, Cab04, Cab05, Cab13 or Cab15 to human recombinant C5a. FIG. 1B shows the binding curves of Cab01, Cab03, Cab04, Cab05, Cab13 or Cab15 to human endogenous C5a.

FIG. 3A shows the binding curve of Cab01, Cab03, Cab04, Cab05, Cab13 (reformatted as human IgG4) or the reference antibody INab308 to human native C5. FIG. 3B shows the binding curve of Cab05-IgG4, Cab35, Cab38, Cab42 (reformatted as human IgG1) or the reference antibody INab308 to human native C5. FIG. 3C shows the binding curve of Cab42, Cab44, Cab45 (reformatted as human IgG1) or the reference antibody INab308 to human native C5.

FIG. 9A shows the competitive binding ELISA with INab308, FIG. 9B shows the competitive binding ELISA with Cab42-IgG1, FIG. 9C shows the competitive binding ELISA with BNJ383, FIG. 9D shows the competitive binding ELISA with MEDI-7814.

IgG1. FIG. 9E shows the competitive binding ELISA with INab308, FIG. 9F shows the competitive binding ELISA with Cab35-IgG1.

FIGS. 10A-10D show the results of the ELISA binding curves of the antibody Cab42-IgG1 with mutated C5a. FIGS. 10E-10H show the results of the ELISA binding curves of the antibody Cab44-IgG1 with mutated C5a. FIGS. 10I-10L show the results of the ELISA binding curves of the antibody Cab45-IgG1 with mutated C5a.

DETAILED DESCRIPTION

Figure 1A:
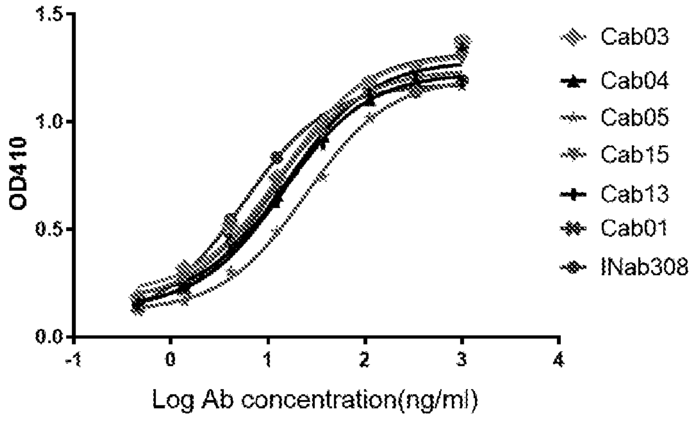
FIGS. 1A-1B show the binding affinity of exemplary anti-C5a antibodies to human recombinant C5a or endogenous C5a as analyzed by ELISA.

The present application in one aspect provides anti-C5a antibodies or antigen binding fragments. By using a combination of selections on scFv phage libraries, affinity maturation and appropriately designed biochemical and biological assays, we have identified highly potent antibody molecules that bind to human C5a and inhibit the action of human C5a. The results presented herein indicate that our antibodies or binding fragments bind a different region or epitope of C5a compared with the known anti-C5a antibodies, and didn't compete with the known anti-C5a antibodies. In some embodiments, the isolated anti-C5a antibodies or antigen binding fragments bind to the human C5 and C5a. In some embodiments, the isolated anti-C5a antibodies or antigen binding fragments bind to the free human C5a polypeptide in the presence of a 2 fold or more molar excess of uncleaved, native human C5, and inhibit the C5a-mediated inflammatory response, which is known to play an integral part in the pathogenesis of complement-associated disorders, such as, but not limited to, sepsis, RA, and asthma. As the concentration of C5 in human serum is much higher than C5a, if the antibodies bind both C5 and C5a with equal binding strength, high concentrations and/or frequent administration of anti-C5a antibodies will be needed. The advantages of antibodies or antigen binding fragments described herein are that, as they bind a new epitope of C5a, and exhibit extremely lower binding affinity to human C5 in ELISA binding assay and Biacore assay, it can be administered to a human at a much lower dose and/or less frequently than other anti-C5a antibodies, and effectively provides the same or greater inhibition of C5a in a human. Surprisingly, in some aspects, the antibodies were even more potent than the control antibody INab308 as demonstrated in a variety of biological assays.

The anti-C5a antibodies provided by the present application include, for example, full-length anti-C5a antibodies, anti-C5a scFvs, anti-C5a Fc fusion proteins, multi-specific (such as bispecific) anti-C5a antibodies, anti-C5a immunoconjugates, and the like.

In one aspect, the present application provides an isolated anti-C5a antibody that specifically binds to an epitope on human C5a, wherein the isolated anti-C5a antibody specifically binds to at least one amino acid residue selected from residue D at position 31, residue E at position 32 and residue R at position 40 of human C5a as shown in SEQ ID NO: 141. In some embodiments, the isolated anti-C5a antibody specifically binds residues 31-40 of human C5a as shown in SEQ ID NO: 141.

In another aspect, there is provided an anti-C5a antibody, wherein the anti-C5a antibody comprises a heavy chain variable domain ($V_H$) comprising a heavy chain complementarity determining region HC-CDR1 comprising $X_1YYX_2Q$ (SEQ ID NO: 67), wherein $X_1$ is D, or N, and $X_2$ is M, or I; an HC-CDR2 comprising $LIRX_1KX_2X_3GX_4TX_5X_6X_7AASX_8KG$ (SEQ ID NO: 68), wherein $X_1$ is K, or N, $X_2$ is A, or V, $X_3$ is V, N, or I, $X_4$ is G, E, F, H, I, Q, or R, $X_5$ is T, V, or A, $X_6$ is Q, E, T, or S, $X_7$ is Y or F, and $X_8$ is V or L; and an HC-CDR3 comprising $RX_1GPPGLX_2$ (SEQ ID NO: 69), wherein $X_1$ is A, L, or V, and $X_2$ is T, S, or A; and a light chain variable domain ($V_L$) comprising a light chain complementarity determining region LC-CDR1 comprising $RSSQX_1LLX_2X_3X_4X_5YX_6YX_7D$ (SEQ ID NO: 70), wherein $X_1$ is S, R, or N, $X_2$ is A, H, or D, $X_3$ is S or T, $X_4$ is D or N, $X_5$ is G, A, or R, $X_6$ is N, I, T, E, or A, and $X_7$ is I, M, L, or V; a LC-CDR2 comprising $GX_1SX_2RAS$ (SEQ ID NO: 71), wherein $X_1$ is G or A, $X_2$ is N or K; and a LC-CDR3 comprising $X_1QHX_2X_3LPX_4T$ (SEQ ID NO: 72), wherein $X_1$ is L or M, $X_2$ is R or K, $X_3$ is A or V, and $X_4$ is P, or L.

Also provided are nucleic acids encoding the anti-C5a antibodies, compositions comprising the anti-C5a antibodies, and methods of making and using the anti-C5a antibodies.

Definitions

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of the disease (such as, for example, tumor volume for cancer). The methods of the application contemplate any one or more of these aspects of treatment.

The term "antibody" includes full-length antibodies and antigen-binding fragments thereof. A full-length antibody comprises two heavy chains and two light chains. The variable regions of the light and heavy chains are responsible for antigen binding. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a single domain antibody, a nanobody, a domain antibody, a bivalent domain antibody, or any other antibody fragments that bind to an antigen but do not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody "competes" for binding to a target C5a with a second antibody when the first antibody inhibits target C5a binding of the second antibody by at least about 50% (such as at least about any of 55%, 60%, 65%, 70%, 75%, 80%, 85%, 90%, 95%, 98% or 99%) in the presence of an equimolar concentration of the first antibody, or vice versa. A high throughput process for "binning" antibodies based upon their cross-competition is described in PCT Publication No. WO 03/48731.

As used herein, the term "specifically binds," "specifically recognizing," or "is specific for" refers to measurable and reproducible interactions, such as binding between a target and an antibody that is determinative of the presence of the target in the presence of a heterogeneous population of molecules, including biological molecules. For example, an antibody that specifically recognizes a target (which can be an epitope) is an antibody that binds to this target with greater affinity, avidity, more readily, and/or with greater duration than its bindings to other targets. In some embodiments, an antibody that specifically recognizes an antigen reacts with one or more antigenic determinants of the antigen with a binding affinity that is at least about 10 times its binding affinity for other targets.

An "isolated" anti-C5a antibody as used herein refers to an anti-C5a antibody that (1) is not associated with proteins found in nature, (2) is free of other proteins from the same source, (3) is expressed by a cell from a different species, or, (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.,* 273: 927-948 (1997); MacCallum et al., J. Mol. Biol. 262:732-745 (1996); Abhinandan and Martin, *Mol. Immunol.,* 45: 3832-3839 (2008); Lefranc M. P. et al., Dev. Comp. Immunol., 27: 55-77 (2003); and Honegger and Pluckthun, *J. Mol. Biol.,* 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, *Mol. Immunol.,* 45: 3832-3839 (2008); Ehrenmann F. et al., *Nucleic Acids Res.,* 38: D301-D307 (2010); and Adolf-Bryfogle J. et al., *Nucleic Acids Res.,* 43: D432-D438 (2015). The contents of the references cited in this paragraph are incorporated herein by reference in their entireties for use in the present application and for possible inclusion in one or more claims herein.

TABLE 1

CDR DEFINITIONS

| | Kabat[1] | Chothia[2] | MacCallum[3] | IMGT[4] | AHo[5] |
|---|---|---|---|---|---|
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The term "chimeric antibody" refers to a antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this application (see U.S. Pat. No. 4,816,567; and Morrison et al., Proc. Natl. Acad. Sci. USA, 81:6851-6855 (1984)).

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA,* 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skilled in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5):1792-1797, 2004; Edgar, R. C., *BMC Bioinformatics* 5(1):113, 2004).

The terms "Fc receptor" or "FcR" are used to describe a receptor that binds to the Fc region of an antibody. In some embodiments, an FcR of this application is one that binds to an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" comprises the stretch of residues of C-terminal to a CH2 domain in an Fc region (i.e. from about amino acid residue 341 to the C-terminal end of an antibody sequence, typically at amino acid residue 446 or 447 of an IgG).

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent Kd or $IC_{50}$ value) than the parent polypeptide or a native sequence IgG Fc. According to some embodiments, the improvement in binding compared to a parent polypeptide is about 3 fold, such as about any of 5, 10, 25, 50, 60, 100, 150, 200, or up to 500 fold, or about 25% to 1000% improvement in binding. The polypeptide variant which "exhibits decreased binding" to an FcR, binds at least one FcR with lower affinity (e.g., higher apparent Kd or higher $IC_{50}$ value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

The polypeptide comprising a variant Fc region which "exhibits increased ADCC" or mediates ADCC in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g., in an animal model etc. In some embodiments, the variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See also, Idusogie et al. *J. Immunol.* 164: 4178-4184 (2000).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position.

The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

An "effective amount" of an anti-C5a antibody or composition as disclosed herein, is an amount sufficient to carry out a specifically stated purpose. An "effective amount" can be determined empirically and by known methods relating to the stated purpose.

The term "therapeutically effective amount" refers to an amount of an anti-C5a antibody or composition as disclosed herein, effective to "treat" a disease or disorder in an individual. In the case of cancer, the therapeutically effective amount of the anti-C5a antibody or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the anti-C5a antibody or composition as disclosed herein can prevent growth and/or kill existing cancer cells, it can be cytostatic and/or cytotoxic. In some embodiments, the therapeutically effective amount is a growth inhibitory amount. In some embodiments, the therapeutically effective amount is an amount that extends the survival of a patient. In some embodiments, the therapeutically effective amount is an amount that improves progression free survival of a patient.

As used herein, by "pharmaceutically acceptable" or "pharmacologically compatible" is meant a material that is not biological or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that embodiments of the application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "an," and "the" include plural referents unless the context clearly dictates otherwise.

Anti-C5a Antibodies

In one aspect, the present application provides anti-C5a antibodies that specifically bind to C5a. Anti-C5a antibodies include, but are not limited to, humanized antibodies, chimeric antibodies, mouse antibodies, rabbit antibodies, monkey antibodies, human antibodies, and antibodies comprising the heavy chain and/or light chain CDRs discussed herein. In one aspect, the present application provides isolated antibodies that bind to C5a. Contemplated anti-C5a antibodies include, for example, full-length anti-C5a antibodies (e.g., full-length IgG1 or IgG4), anti-C5a scFvs, anti-C5a Fc fusion proteins, multi-specific (such as bispecific) anti-C5a antibodies, anti-C5a immunoconjugates, and the like. In some embodiments, the anti-C5a antibody is a full-length antibody (e.g., full-length IgG1 or IgG4) or antigen-binding fragment thereof, which specifically binds to C5a. In some embodiments, the anti-C5a antibody is a Fab, a Fab', a F(ab)'2, a Fab'-SH, a single-chain Fv (scFv), an Fv fragment, a dAb, a Fd, a nanobody, a diabody, or a linear antibody. In some embodiments, reference to an antibody that specifically binds to C5a means that the antibody binds to C5a with an affinity that is at least about 10 times (including for example at least about any one of 10, $10^2$, $10^3$, $10^4$, $10^5$, $10^6$, or $10^7$ times) more tightly than its binding affinity for a non-target. In some embodiments, the non-target is an antigen that is not C5a. Binding affinity can be determined by methods known in the art, such as ELISA, fluorescence activated cell sorting (FACS) analysis, or radioimmunoprecipitation assay (RIA). Kd can be determined by methods known in the art, such as surface plasmon resonance (SPR) assay or biolayer interferometry (BLI).

Although anti-C5a antibodies containing human sequences (e.g., human heavy and light chain variable domain sequences comprising human CDR sequences) are extensively discussed herein, non-human anti-C5a antibodies are also contemplated. In some embodiments, non-human anti-C5a antibodies comprise human CDR sequences from an anti-C5a antibody as described herein and non-human framework sequences. Non-human framework sequences include, in some embodiments, any sequence that can be used for generating synthetic heavy and/or light chain variable domains using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a non-human anti-C5a antibody includes an anti-C5a antibody generated by grafting one or more human CDR sequences as described herein onto a non-human framework sequence (e.g., a mouse or chicken framework sequence).

The complete amino acid sequence of an exemplary human C5a comprises or consists of the amino acid sequence of SEQ ID NO: 141.

In some embodiments, the anti-C5a antibody described herein specifically recognizes an epitope within human C5a. In some embodiments, the anti-C5a antibody cross-reacts with C5a from species other than human. In some embodiments, the anti-C5a antibody is completely specific for human C5a and does not exhibit cross-reactivity with non-human species or other types of C5a.

In some embodiments, the anti-C5a antibody described herein specifically binds to a linear epitope within human C5a. In some embodiments, the anti-C5a antibody described herein specifically binds to a nonlinear epitope within human C5a. In some embodiments, the anti-C5a antibody described herein specifically binds to an epitope on human C5a, wherein the isolated anti-C5a antibody specifically binds to at least one amino acid residue selected from residue D at position 31, residue E at position 32 and residue R at position 40 of human C5a as shown in SEQ ID NO: 141. In some embodiments, the isolated anti-C5a antibody specifically binds residues 31-40 of human C5a as shown in SEQ ID NO: 141.

In some embodiments, the anti-C5a antibody cross-reacts with at least one allelic variant of the C5a protein (or fragments thereof). In some embodiments, the allelic variant has up to about 30 (such as about any of 1, 2, 3, 4, 5, 6, 7, 8, 9, 10, 15, 20, 25, or 30) amino acid substitutions (such as a conservative substitution) when compared to the naturally occurring C5a (or fragments thereof). In some embodiments, the anti-C5a antibody does not cross-react with any allelic variants of the C5a protein (or fragments thereof).

In some embodiments, the anti-C5a antibody cross-reacts with at least one interspecies variant of the C5a protein. In some embodiments, for example, the C5a protein (or fragments thereof) is human C5a and the interspecies variant of the C5a protein (or fragments thereof) is a cynomolgus monkey variant thereof. In some embodiments, the anti-C5a antibody does not cross-react with any interspecies variants of the C5a protein.

In some embodiments, according to any of the anti-C5a antibodies described herein, the anti-C5a antibody comprises an antibody heavy chain constant region and an antibody light chain constant region. In some embodiments, the anti-C5a antibody comprises an IgG1 heavy chain constant region. In some embodiments, the anti-C5a antibody comprises an IgG2 heavy chain constant region. In some embodiments, the anti-C5a antibody comprises an IgG3 heavy chain constant region. In some embodiments, the anti-C5a antibody comprises an IgG4 heavy chain constant region. In some embodiments, the heavy chain constant region comprises (including consisting of or consisting essentially of) the amino acid sequence of SEQ ID NO: 142. In some embodiments, the heavy chain constant region comprises (including consisting of or consisting essentially of) the amino acid sequence of SEQ ID NO: 143. In some embodiments, the anti-C5a comprises a lambda light chain constant region. In some embodiments, the anti-C5a antibody comprises a kappa light chain constant region. In some embodiments, the light chain constant region comprises (including consisting of or consisting essentially of) the amino acid sequence of SEQ ID NO: 144. In some embodiments, the anti-C5a antibody comprises an antibody heavy chain variable domain and an antibody light chain variable domain.

In some embodiments, the anti-C5a antibody comprises a $V_H$ comprising an HC-CDR1 comprising $X_1YYX_2Q$ (SEQ ID NO: 67), wherein $X_1$ is D, or N, and $X_2$ is M, or I; an HC-CDR2 comprising $LIRX_1KX_2X_3GX_4TX_5X_6X_7AASX_8KG$ (SEQ ID NO: 68), wherein $X_1$ is K, or N, $X_2$ is A, or V, $X_3$ is V, N, or I, $X_4$ is G, E, F, H, I, Q, or R, $X_5$ is T, V, or A, $X_6$ is Q, E, T, or S, $X_7$ is Y or F, and $X_8$ is V or L; and an HC-CDR3 comprising $RX_1GPPGLX_2$ (SEQ ID NO: 69), wherein $X_1$ is A, L, or V, and $X_2$ is T, S, or A; and a $V_L$ comprising a LC-CDR1 comprising $RSSQX_1LLX_2X_3X_4X_5YX_6YX_7D$ (SEQ ID NO: 70), wherein $X_1$ is S, R, or N, $X_2$ is A, H, or D, $X_3$ is S or T, $X_4$ is D or N, $X_5$ is G, A, or R, $X_6$ is N, I, T, E, or A, and $X_7$ is I, M, L, or V; a LC-CDR2 comprising $GX_1SX_2RAS$ (SEQ ID NO: 71), wherein $X_1$ is G or A, $X_2$ is N or K; and a LC-CDR3 comprising $X_1QHX_2X_3LPX_4T$ (SEQ ID NO: 72), wherein $X_1$ is L or M, $X_2$ is R or K, $X_3$ is A or V, and $X_4$ is P, or L.

In some embodiments, the anti-C5a antibody comprises a $V_H$ comprising: an HC-CDR1 comprising an amino acid sequence having at least about 90% sequence identify with any one of SEQ ID NOs: 1-6, an HC-CDR2 comprising an amino acid sequence having at least about 90% sequence identify with any one of SEQ ID NOs: 7-29, and an HC-CDR3 comprising an amino acid sequence having at least about 90% sequence identify with any one of SEQ ID NOs: 30-38.

In some embodiments, the anti-C5a antibody comprises a $V_H$ comprising: an HC-CDR1 comprising the amino acid sequence of any one of SEQ ID NOs: 1-6, an HC-CDR2 comprising the amino acid sequence of any one of SEQ ID NOs: 7-29, and an HC-CDR3 comprising the amino acid sequence of any one of SEQ ID NOs: 30-38.

In some embodiments, the anti-C5a antibody comprises a $V_L$ comprising: an LC-CDR1 comprising an amino acid sequence having at least about 90% sequence identify with any one of SEQ ID NOs: 39-56, an LC-CDR2 comprising an amino acid sequence having at least about 90% sequence identify with any one of SEQ ID NOs: 57-59, and an LC-CDR3 comprising an amino acid sequence having at least about 90% sequence identify with any one of SEQ ID NOs: 60-66.

In some embodiments, the anti-C5a antibody comprises a $V_L$ comprising: an LC-CDR1 comprising the amino acid sequence of any one of SEQ ID NOs: 39-56, an LC-CDR2 comprising the amino acid sequence of any one of SEQ ID NOs: 57-59, and an LC-CDR3 comprising the amino acid sequence of any one of SEQ ID NOs: 60-66.

In some embodiments, the anti-C5a antibody comprises a $V_H$ comprising: an HC-CDR1 comprising an amino acid sequence having at least about 90% sequence identify with any one of SEQ ID NOs: 1-6, an HC-CDR2 comprising an amino acid sequence having at least about 90% sequence identify with any one of SEQ ID NOs: 7-29, and an HC-CDR3 comprising an amino acid sequence having at least about 90% sequence identify with any one of SEQ ID NOs: 30-38; and a $V_L$ comprising: an LC-CDR1 comprising an amino acid sequence having at least about 90% sequence identify with any one of SEQ ID NOs: 39-56, an LC-CDR2 comprising an amino acid sequence having at least about 90% sequence identify with any one of SEQ ID NOs: 57-59, and an LC-CDR3 comprising an amino acid sequence having at least about 90% sequence identify with any one of SEQ ID NOs: 60-66.

In some embodiments, the anti-C5a antibody comprises a $V_H$ comprising: an HC-CDR1 comprising the amino acid sequence of any one of SEQ ID NOs: 1-6, an HC-CDR2 comprising the amino acid sequence of any one of SEQ ID NOs: 7-29, and an HC-CDR3 comprising the amino acid sequence of any one of SEQ ID NOs: 30-38; and a $V_L$ comprising: an LC-CDR1 comprising the amino acid sequence of any one of SEQ ID NOs: 39-56, an LC-CDR2 comprising the amino acid sequence of any one of SEQ ID NOs: 57-59, and an LC-CDR3 comprising the amino acid sequence of any one of SEQ ID NOs: 60-66.

In some embodiments, the anti-C5a antibody comprises a $V_H$ comprising: an HC-CDR1 comprising an amino acid sequence having at least about 90% sequence identify with SEQ ID NO: 1, an HC-CDR2 comprising an amino acid sequence having at least about 90% sequence identify with SEQ ID NO: 7, and an HC-CDR3 comprising an amino acid sequence having at least about 90% sequence identify with SEQ ID NO: 30; and a $V_L$ comprising: an LC-CDR1 comprising an amino acid sequence having at least about 90% sequence identify with SEQ ID NO: 39, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 60.

In some embodiments, the anti-C5a antibody comprises a $V_H$ comprising: an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 30; and a $V_L$ comprising: an LC-CDR1 comprising the amino acid sequence of SEQ ID NO: 39, an LC-CDR2 comprising the amino acid sequence of SEQ ID NO: 57, and an LC-CDR3 comprising the amino acid sequence of SEQ ID NO: 60.

In some embodiments, the anti-C5a antibody comprises a $V_H$ comprising: an HC-CDR1 comprising an amino acid sequence having at least about 90% sequence identify with SEQ ID NO: 2, an HC-CDR2 comprising an amino acid sequence having at least about 90% sequence identify with SEQ ID NO: 8, and an HC-CDR3 comprising an amino acid sequence having at least about 90% sequence identify with SEQ ID NO: 31; and a $V_L$ comprising an LC-CDR1 comprising an amino acid sequence having at least about 90% sequence identify with SEQ ID NO: 40, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61.

In some embodiments, the anti-C5a antibody comprises a $V_H$ comprising: an HC-CDR1 comprising the amino acid sequence of SEQ ID NO: 2, an HC-CDR2 comprising the amino acid sequence of SEQ ID NO: 8, and an HC-CDR3 comprising the amino acid sequence of SEQ ID NO: 31; and a $V_L$ comprising an LC-CDR1 comprising the amino acid sequence of SEQ ID NO: 40, an LC-CDR2 comprising the amino acid sequence of SEQ ID NO: 57, and an LC-CDR3 comprising the amino acid sequence of SEQ ID NO: 61.

In some embodiments, the anti-C5a antibody comprises a $V_H$ comprising: an HC-CDR1 comprising an amino acid sequence having at least about 90% sequence identify with SEQ ID NO: 2, an HC-CDR2 comprising an amino acid sequence having at least about 90% sequence identify with SEQ ID NO: 10, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 42, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61.

In some embodiments, the anti-C5a antibody comprises a $V_H$ comprising: an HC-CDR1 comprising the amino acid sequence of SEQ ID NO: 2, an HC-CDR2 comprising the amino acid sequence of SEQ ID NO: 10, and an HC-CDR3 comprising the amino acid sequence of SEQ ID NO: 32; and a $V_L$ comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61.

In some embodiments, the anti-C5a antibody comprises a $V_H$ comprising: an HC-CDR1 comprising an amino acid sequence having at least about 90% sequence identify with SEQ ID NO: 2, an HC-CDR2 comprising an amino acid sequence having at least about 90% sequence identify with SEQ ID NO: 11, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 41, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 64.

In some embodiments, the anti-C5a antibody comprises a $V_H$ comprising: an HC-CDR1 comprising the amino acid sequence of SEQ ID NO: 2, an HC-CDR2 comprising the amino acid sequence of SEQ ID NO: 11, and an HC-CDR3 comprising the amino acid sequence of SEQ ID NO: 32; and a $V_L$ comprising an LC-CDR1 comprising the amino acid sequence of SEQ ID NO: 41, an LC-CDR2 comprising the amino acid sequence of SEQ ID NO: 57, and an LC-CDR3 comprising the amino acid sequence of SEQ ID NO: 64.

In some embodiments, the anti-C5a antibody comprises a $V_H$ comprising: an HC-CDR1 comprising an amino acid sequence having at least about 90% sequence identify with SEQ ID NO: 2, an HC-CDR2 comprising an amino acid sequence having at least about 90% sequence identify with SEQ ID NO: 9, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 43, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 63.

In some embodiments, the anti-C5a antibody comprises a $V_H$ comprising: an HC-CDR1 comprising the amino acid sequence of SEQ ID NO: 2, an HC-CDR2 comprising the amino acid sequence of SEQ ID NO: 9, and an HC-CDR3 comprising the amino acid sequence of SEQ ID NO: 32; and a $V_L$ comprising an LC-CDR1 comprising the amino acid sequence of SEQ ID NO: 43, an LC-CDR2 comprising the amino acid sequence of SEQ ID NO: 57, and an LC-CDR3 comprising the amino acid sequence of SEQ ID NO: 63.

In some embodiments, the anti-C5a antibody comprises a $V_H$ comprising an HC-CDR1 comprising an amino acid sequence having at least about 90% sequence identify with SEQ ID NO: 2, an HC-CDR2 comprising an amino acid sequence having at least about 90% sequence identify with SEQ ID NO: 11, and an HC-CDR3 comprising an amino acid sequence having at least about 90% sequence identify with SEQ ID NO: 35; and a $V_L$ comprising an LC-CDR1 comprising an amino acid sequence having at least about 90% sequence identify with SEQ ID NO: 44, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 60.

In some embodiments, the anti-C5a antibody comprises a $V_H$ comprising an HC-CDR1 comprising the amino acid sequence of SEQ ID NO: 2, an HC-CDR2 comprising the amino acid sequence of SEQ ID NO: 11, and an HC-CDR3 comprising the amino acid sequence of SEQ ID NO: 35; and a $V_L$ comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 60.

In some embodiments, the anti-C5a antibody comprises a $V_H$ comprising: an HC-CDR1 comprising an amino acid sequence having at least about 90% sequence identify with SEQ ID NO: 6, an HC-CDR2 comprising an amino acid sequence having at least about 90% sequence identify with SEQ ID NO: 18, and an HC-CDR3 comprising an amino acid sequence having at least about 90% sequence identify with SEQ ID NO: 36; and a $V_L$ comprising an LC-CDR1 comprising an amino acid sequence having at least about 90% sequence identify with SEQ ID NO: 42, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61.

In some embodiments, the anti-C5a antibody comprises a $V_H$ comprising: an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 36; and a $V_L$ comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61.

In some embodiments, the anti-C5a antibody comprises a $V_H$ comprising: an HC-CDR1 comprising an amino acid sequence having at least about 90% sequence identify with SEQ ID NO: 5, an HC-CDR2 comprising an amino acid sequence having at least about 90% sequence identify with SEQ ID NO: 21, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 42, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61.

In some embodiments, the anti-C5a antibody comprises a $V_H$ comprising: an HC-CDR1 comprising the amino acid sequence of SEQ ID NO: 5, an HC-CDR2 comprising the amino acid sequence of SEQ ID NO: 21, and an HC-CDR3 comprising the amino acid sequence of SEQ ID NO: 32; and a $V_L$ comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61.

In some embodiments, the anti-C5a antibody comprises a $V_H$ comprising: an HC-CDR1 comprising an amino acid sequence having at least about 90% sequence identify with SEQ ID NO: 2, an HC-CDR2 comprising an amino acid sequence having at least about 90% sequence identify with SEQ ID NO: 10, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 53, an LC-CDR2 comprising an amino acid sequence having at least about 90% sequence identify with SEQ ID NO: 59, and an LC-CDR3 comprising an amino acid sequence having at least about 90% sequence identify with SEQ ID NO: 65.

In some embodiments, the anti-C5a antibody comprises a $V_H$ comprising: an HC-CDR1 comprising the amino acid sequence of SEQ ID NO: 2, an HC-CDR2 comprising the amino acid sequence of SEQ ID NO: 10, and an HC-CDR3 comprising the amino acid sequence of SEQ ID NO: 32; and a $V_L$ comprising an LC-CDR1 comprising the amino acid sequence of SEQ ID NO: 53, an LC-CDR2 comprising the amino acid sequence of SEQ ID NO: 59, and an LC-CDR3 comprising the amino acid sequence of SEQ ID NO: 65.

In some embodiments, the anti-C5a antibody comprises a $V_H$ comprising: an HC-CDR1 comprising an amino acid sequence having at least about 90% sequence identify with SEQ ID NO: 2, an HC-CDR2 comprising an amino acid sequence having at least about 90% sequence identify with SEQ ID NO: 23, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 42, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61.

In some embodiments, the anti-C5a antibody comprises a $V_H$ comprising: an HC-CDR1 comprising the amino acid sequence of SEQ ID NO: 2, an HC-CDR2 comprising the amino acid sequence of SEQ ID NO: 23, and an HC-CDR3 comprising the amino acid sequence of SEQ ID NO: 32; and a $V_L$ comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61.

In some embodiments, the anti-C5a antibody comprises a $V_H$ comprising: an HC-CDR1 comprising an amino acid sequence having at least about 90% sequence identify with SEQ ID NO: 2, an HC-CDR2 comprising an amino acid sequence having at least about 90% sequence identify with SEQ ID NO: 23, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 56, an LC-CDR2 comprising an amino acid sequence having at least about 90% sequence identify with SEQ ID NO: 57, and an LC-CDR3 comprising an amino acid sequence having at least about 90% sequence identify with SEQ ID NO: 61.

In some embodiments, the anti-C5a antibody comprises a $V_H$ comprising: an HC-CDR1 comprising the amino acid sequence of SEQ ID NO: 2, an HC-CDR2 comprising the amino acid sequence of SEQ ID NO: 23, and an HC-CDR3 comprising the amino acid sequence of SEQ ID NO: 32; and a $V_L$ comprising an LC-CDR1 comprising the amino acid sequence of SEQ ID NO: 56, an LC-CDR2 comprising the amino acid sequence of SEQ ID NO: 57, and an LC-CDR3 comprising the amino acid sequence of SEQ ID NO: 61.

In some embodiments, the anti-C5a antibody comprises a $V_H$ comprising: an HC-CDR1 comprising an amino acid sequence having at least about 90% sequence identify with SEQ ID NO: 6, an HC-CDR2 comprising an amino acid sequence having at least about 90% sequence identify with SEQ ID NO: 18, and an HC-CDR3 comprising an amino acid sequence having at least about 90% sequence identify with SEQ ID NO: 36; and a $V_L$ comprising an LC-CDR1 comprising an amino acid sequence having at least about 90% sequence identify with SEQ ID NO: 52, an LC-CDR2 comprising an amino acid sequence having at least about 90% sequence identify with SEQ ID NO: 58, and an LC-CDR3 comprising an amino acid sequence having at least about 90% sequence identify with SEQ ID NO: 61.

In some embodiments, the anti-C5a antibody comprises a $V_H$ comprising: an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 36; and a $V_L$ comprising an LC-CDR1 comprising the amino acid sequence of SEQ ID NO: 52, an LC-CDR2 comprising the amino acid sequence of SEQ ID NO: 58, and an LC-CDR3 comprising the amino acid sequence of SEQ ID NO: 61.

In some embodiments, the anti-C5a antibody comprises a $V_H$ comprising: an HC-CDR1 comprising an amino acid sequence having at least about 90% sequence identify with SEQ ID NO: 6, an HC-CDR2 comprising an amino acid sequence having at least about 90% sequence identify with SEQ ID NO: 18, and an HC-CDR3 comprising an amino acid sequence having at least about 90% sequence identify with SEQ ID NO: 36; and a $V_L$ comprising an LC-CDR1 comprising an amino acid sequence having at least about 90% sequence identify with SEQ ID NO: 53, an LC-CDR2 comprising an amino acid sequence having at least about 90% sequence identify with SEQ ID NO: 59, and an LC-CDR3 comprising an amino acid sequence having at least about 90% sequence identify with SEQ ID NO: 65.

In some embodiments, the anti-C5a antibody comprises a $V_H$ comprising: an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 36; and a $V_L$ comprising an LC-CDR1 comprising the amino acid sequence of SEQ ID NO: 53, an LC-CDR2 comprising the amino acid sequence of SEQ ID NO: 59, and an LC-CDR3 comprising the amino acid sequence of SEQ ID NO: 65.

In some embodiments, the anti-C5a antibody comprises a $V_H$ comprising: an HC-CDR1 comprising an amino acid sequence having at least about 90% sequence identify with SEQ ID NO: 5, an HC-CDR2 comprising an amino acid sequence having at least about 90% sequence identify with SEQ ID NO: 21, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 52, an LC-CDR2 comprising an amino acid sequence having at least about 90% sequence identify with SEQ ID NO: 58, and an LC-CDR3 comprising an amino acid sequence having at least about 90% sequence identify with SEQ ID NO: 61.

In some embodiments, the anti-C5a antibody comprises a $V_H$ comprising: an HC-CDR1 comprising the amino acid sequence of SEQ ID NO: 5, an HC-CDR2 comprising the amino acid sequence of SEQ ID NO: 21, and an HC-CDR3 comprising the amino acid sequence of SEQ ID NO: 32; and a $V_L$ comprising an LC-CDR1 comprising the amino acid sequence of SEQ ID NO: 52, an LC-CDR2 comprising the amino acid sequence of SEQ ID NO: 58, and an LC-CDR3 comprising the amino acid sequence of SEQ ID NO: 61.

In some embodiments, the anti-C5a antibody comprises a $V_H$ comprising: an HC-CDR1 comprising an amino acid sequence having at least about 90% sequence identify with SEQ ID NO: 5, an HC-CDR2 comprising an amino acid sequence having at least about 90% sequence identify with SEQ ID NO: 21, and an HC-CDR3 comprising an amino acid sequence having at least about 90% sequence identify with SEQ ID NO: 32; and a $V_L$ comprising an LC-CDR1 comprising an amino acid sequence having at least about 90% sequence identify with SEQ ID NO: 53, an LC-CDR2 comprising an amino acid sequence having at least about 90% sequence identify with SEQ ID NO: 59, and an LC-CDR3 comprising an amino acid sequence having at least about 90% sequence identify with SEQ ID NO: 65.

In some embodiments, the anti-C5a antibody comprises a $V_H$ comprising: an HC-CDR1 comprising the amino acid sequence of SEQ ID NO: 5, an HC-CDR2 comprising the amino acid sequence of SEQ ID NO: 21, and an HC-CDR3 comprising the amino acid sequence of SEQ ID NO: 32; and a $V_L$ comprising an LC-CDR1 comprising the amino acid sequence of SEQ ID NO: 53, an LC-CDR2 comprising the amino acid sequence of SEQ ID NO: 59, and an LC-CDR3 comprising the amino acid sequence of SEQ ID NO: 65.

In some embodiments, the anti-C5a antibody comprises a $V_H$ comprising an amino acid sequences having at least about 90% sequence identify with any one of SEQ ID NOs: 1-38; and a $V_L$ comprising an amino acid sequences having at least about 90% sequence identify with any one of SEQ ID NOs: 39-66. In some embodiments, the anti-C5a antibody comprises a $V_H$ comprising the amino acid sequences of any one of SEQ ID NOs: 1-38; and a $V_L$ comprising the amino acid sequences of any one of SEQ ID NOs: 39-66.

In some embodiments, the anti-C5a antibody comprises a $V_H$ comprising the amino acid sequences having at least about 90% sequence identify with SEQ ID NOs: 1, 7 and 30; and a $V_L$ comprising the amino acid sequences having at least about 90% sequence identify with SEQ ID NOs: 39, 57 and 60. In some embodiments, the anti-C5a antibody comprises a $V_H$ comprising the amino acid sequences of SEQ ID NOs: 1, 7 and 30; and a $V_L$ comprising the amino acid sequences of SEQ ID NOs: 39, 57 and 60.

In some embodiments, the anti-C5a antibody comprises a $V_H$ comprising the amino acid sequences having at least about 90% sequence identify with SEQ ID NOs: 2, 8 and 31; and a $V_L$ comprising the amino acid sequences having at least about 90% sequence identify with SEQ ID NOs: 40, 57 and 61. In some embodiments, the anti-C5a antibody comprises a $V_H$ comprising the amino acid sequences of SEQ ID NOs: 2, 8 and 31; and a $V_L$ comprising the amino acid sequences of SEQ ID NOs: 40, 57 and 61.

In some embodiments, the anti-C5a antibody comprises a $V_H$ comprising the amino acid sequences having at least about 90% sequence identify with SEQ ID NOs: 2, 10 and 32; and a $V_L$ comprising the amino acid sequences having at least about 90% sequence identify with SEQ ID NOs: 42, 57 and 61. In some embodiments, the anti-C5a antibody comprises a $V_H$ comprising the amino acid sequences of SEQ ID NOs: 2, 10 and 32; and a $V_L$ comprising the amino acid sequences of SEQ ID NOs: 42, 57 and 61.

In some embodiments, the anti-C5a antibody comprises a $V_H$ comprising the amino acid sequences having at least about 90% sequence identify with SEQ ID NOs: 2, 11 and 32; and a $V_L$ comprising the amino acid sequences having at least about 90% sequence identify with SEQ ID NOs: 41, 57 and 64. In some embodiments, the anti-C5a antibody comprises a $V_H$ comprising the amino acid sequences of SEQ ID NOs: 2, 11 and 32; and a $V_L$ comprising the amino acid sequences of SEQ ID NOs: 41, 57 and 64.

In some embodiments, the anti-C5a antibody comprises a $V_H$ comprising the amino acid sequences having at least about 90% sequence identify with SEQ ID NOs: 2, 9 and 32; and a $V_L$ comprising the amino acid sequences of SEQ ID NOs: 43, 57 and 63. In some embodiments, the anti-C5a antibody comprises a $V_H$ comprising the amino acid sequences of SEQ ID NOs: 2, 9 and 32; and a $V_L$ comprising the amino acid sequences of SEQ ID NOs: 43, 57 and 63.

In some embodiments, the anti-C5a antibody comprises a $V_H$ comprising the amino acid sequences having at least about 90% sequence identify with SEQ ID NOs: 2, 11 and 35; and a $V_L$ comprising the amino acid sequences having at least about 90% sequence identify with SEQ ID NOs: 44, 57 and 60. In some embodiments, the anti-C5a antibody comprises a $V_H$ comprising the amino acid sequences of SEQ ID NOs: 2, 11 and 35; and a $V_L$ comprising the amino acid sequences of SEQ ID NOs: 44, 57 and 60.

In some embodiments, the anti-C5a antibody comprises a $V_H$ comprising the amino acid sequences having at least about 90% sequence identify with SEQ ID NOs: 6, 18 and 36; and a $V_L$ comprising the amino acid sequences having at least about 90% sequence identify with SEQ ID NOs: 42, 57 and 61. In some embodiments, the anti-C5a antibody comprises a $V_H$ comprising the amino acid sequences of SEQ ID NOs: 6, 18 and 36; and a $V_L$ comprising the amino acid sequences of SEQ ID NOs: 42, 57 and 61.

In some embodiments, the anti-C5a antibody comprises a $V_H$ comprising the amino acid sequences having at least about 90% sequence identify with SEQ ID NOs: 5, 21 and 32; and a $V_L$ comprising the amino acid sequences having at least about 90% sequence identify with SEQ ID NOs: 42, 57 and 61. In some embodiments, the anti-C5a antibody comprises a $V_H$ comprising the amino acid sequences of SEQ ID NOs: 5, 21 and 32; and a $V_L$ comprising the amino acid sequences of SEQ ID NOs: 42, 57 and 61.

In some embodiments, the anti-C5a antibody comprises a $V_H$ comprising the amino acid sequences having at least about 90% sequence identify with SEQ ID NOs: 2, 10 and 32; and a $V_L$ comprising the amino acid sequences having at least about 90% sequence identify with SEQ ID NOs: 53, 59 and 65. In some embodiments, the anti-C5a antibody comprises a $V_H$ comprising the amino acid sequences of SEQ ID NOs: 2, 10 and 32; and a $V_L$ comprising the amino acid sequences of SEQ ID NOs: 53, 59 and 65.

In some embodiments, the anti-C5a antibody comprises a $V_H$ comprising the amino acid sequences having at least about 90% sequence identify with SEQ ID NOs: 2, 23 and 32; and a $V_L$ comprising the amino acid sequences having at least about 90% sequence identify with SEQ ID NOs: 42, 57 and 61. In some embodiments, the anti-C5a antibody comprises a $V_H$ comprising the amino acid sequences of SEQ ID NOs: 2, 23 and 32; and a $V_L$ comprising the amino acid sequences of SEQ ID NOs: 42, 57 and 61.

In some embodiments, the anti-C5a antibody comprises a $V_H$ comprising the amino acid sequences having at least about 90% sequence identify with SEQ ID NOs: 2, 23 and 32; and a $V_L$ comprising the amino acid sequences having at least about 90% sequence identify with SEQ ID NOs: 56, 57 and 61. In some embodiments, the anti-C5a antibody comprises a $V_H$ comprising the amino acid sequences of SEQ ID NOs: 2, 23 and 32; and a $V_L$ comprising the amino acid sequences of SEQ ID NOs: 56, 57 and 61.

In some embodiments, the anti-C5a antibody comprises a $V_H$ comprising the amino acid sequences having at least about 90% sequence identify with SEQ ID NOs: 6, 18 and 36; and a $V_L$ comprising the amino acid sequences having at least about 90% sequence identify with SEQ ID NOs: 52, 58 and 61. In some embodiments, the anti-C5a antibody comprises a $V_H$ comprising the amino acid sequences of SEQ ID NOs: 6, 18 and 36; and a $V_L$ comprising the amino acid sequences of SEQ ID NOs: 52, 58 and 61.

In some embodiments, the anti-C5a antibody comprises a $V_H$ comprising the amino acid sequences having at least about 90% sequence identify with SEQ ID NOs: 6, 18 and 36; and a $V_L$ comprising the amino acid sequences having at least about 90% sequence identify with SEQ ID NOs: 53, 59 and 65. In some embodiments, the anti-C5a antibody comprises a $V_H$ comprising the amino acid sequences of SEQ ID NOs: 6, 18 and 36; and a $V_L$ comprising the amino acid sequences of SEQ ID NOs: 53, 59 and 65.

In some embodiments, the anti-C5a antibody comprises a $V_H$ comprising the amino acid sequences having at least about 90% sequence identify with SEQ ID NOs: 5, 21 and 32; and a $V_L$ comprising the amino acid sequences having at least about 90% sequence identify with SEQ ID NOs: 52, 58 and 61. In some embodiments, the anti-C5a antibody comprises a $V_H$ comprising the amino acid sequences of SEQ ID NOs: 5, 21 and 32; and a $V_L$ comprising the amino acid sequences of SEQ ID NOs: 52, 58 and 61.

In some embodiments, the anti-C5a antibody comprises a $V_H$ comprising the amino acid sequences having at least about 90% sequence identify with SEQ ID NOs: 5, 21 and 32; and a $V_L$ comprising the amino acid sequences having at least about 90% sequence identify with SEQ ID NOs: 53, 59 and 65. In some embodiments, the anti-C5a antibody comprises a $V_H$ comprising the amino acid sequences of SEQ ID NOs: 5, 21 and 32; and a $V_L$ comprising the amino acid sequences of SEQ ID NOs: 53, 59 and 65.

In some embodiments, the anti-C5a antibody comprises a $V_H$ comprising an HC-CDR1, an HC-CDR2, and an HC-CDR3 of a $V_H$ comprising the amino acid sequence of any one of SEQ ID NOs: 73-111; and a $V_L$ comprising a LC-CDR1, a LC-CDR2, and a LC-CDR3 of a $V_L$ comprising the amino acid sequence of any one of SEQ ID NOs: 112-140.

In some embodiments, the anti-C5a antibody comprises a $V_H$ comprising one, two or three HC-CDRs of SEQ ID NO: 73. In some embodiments, the anti-C5a antibody comprises a $V_H$ comprising one, two or three HC-CDRs of SEQ ID NO: 75. In some embodiments, the anti-C5a antibody comprises a $V_H$ comprising one, two or three HC-CDRs of SEQ ID NO: 100. In some embodiments, the anti-C5a antibody comprises a $V_H$ comprising one, two or three HC-CDRs of SEQ ID NO: 79. In some embodiments, the anti-C5a antibody comprises a $V_H$ comprising one, two or three HC-CDRs of SEQ ID NO: 85. In some embodiments, the anti-C5a antibody comprises a $V_H$ comprising one, two or three HC-CDRs of SEQ ID NO: 88. In some embodiments, the anti-C5a antibody comprises a $V_H$ comprising one, two or three HC-CDRs of SEQ ID NO: 93. In some embodiments, the anti-C5a antibody comprises a $V_H$ comprising one, two or three HC-CDRs of SEQ ID NO: 97. In some embodiments, the anti-C5a antibody comprises a $V_H$ comprising one, two or three HC-CDRs of SEQ ID NO: 77. In some embodiments, the anti-C5a antibody comprises a $V_H$ comprising one, two or three HC-CDRs of SEQ ID NO: 102. In some embodiments, the anti-C5a antibody comprises a $V_H$ comprising one, two or three HC-CDRs of SEQ ID NO: 109. In some embodiments, the anti-C5a antibody comprises a $V_H$ comprising one, two or three HC-CDRs of SEQ ID NO: 110. In some embodiments, the anti-C5a antibody comprises a $V_H$ comprising one, two or three HC-CDRs of SEQ ID NO: 111.

In some embodiments, the anti-C5a antibody comprises a $V_L$ comprising one, two or three LC-CDRs of SEQ ID NO: 112. In some embodiments, the anti-C5a antibody comprises a $V_L$ comprising one, two or three LC-CDRs of SEQ ID NO: 114. In some embodiments, the anti-C5a antibody comprises a $V_L$ comprising one, two or three LC-CDRs of SEQ ID NO: 135. In some embodiments, the anti-C5a antibody comprises a $V_L$ comprising one, two or three LC-CDRs of SEQ ID NO: 118. In some embodiments, the anti-C5a antibody comprises a $V_L$ comprising one, two or three LC-CDRs of SEQ ID NO: 117. In some embodiments, the anti-C5a antibody comprises a $V_L$ comprising one, two or three LC-CDRs of SEQ ID NO: 126. In some embodiments, the anti-C5a antibody comprises a $V_L$ comprising one, two or three LC-CDRs of SEQ ID NO: 116.

In some embodiments, the anti-C5a antibody comprises a $V_L$ comprising one, two or three LC-CDRs of SEQ ID NO: 132. In some embodiments, the anti-C5a antibody comprises a $V_L$ comprising one, two or three LC-CDRs of SEQ ID NO: 138. In some embodiments, the anti-C5a antibody comprises a $V_L$ comprising one, two or three LC-CDRs of SEQ ID NO: 139. In some embodiments, the anti-C5a antibody comprises a $V_L$ comprising one, two or three LC-CDRs of SEQ ID NO: 140.

In some embodiments, the anti-C5a antibody comprises a $V_H$ comprising HC-CDR1, HC-CDR2 and HC-CDR3 of the $V_H$ of SEQ ID NO: 73, and a $V_L$ comprising LC-CDR1, LC-CDR2 and LC-CDR3 of the $V_L$ of SEQ ID NO: 112. In some embodiments, the anti-C5a antibody comprises a $V_H$ comprising HC-CDR1, HC-CDR2 and HC-CDR3 of the $V_H$ of SEQ ID NO: 75, and a $V_L$ comprising LC-CDR1, LC-CDR2 and LC-CDR3 of the $V_L$ of SEQ ID NO: 114. In some embodiments, the anti-C5a antibody comprises a $V_H$ comprising HC-CDR1, HC-CDR2 and HC-CDR3 of the $V_H$ of SEQ ID NO: 100, and a $V_L$ comprising LC-CDR1, LC-CDR2 and LC-CDR3 of the $V_L$ of SEQ ID NO: 135. In some embodiments, the anti-C5a antibody comprises a $V_H$ comprising HC-CDR1, HC-CDR2 and HC-CDR3 of the $V_H$ of SEQ ID NO: 79, and a $V_L$ comprising LC-CDR1, LC-CDR2 and LC-CDR3 of the $V_L$ of SEQ ID NO: 118. In some embodiments, the anti-C5a antibody comprises a $V_H$ comprising HC-CDR1, HC-CDR2 and HC-CDR3 of the $V_H$ of SEQ ID NO: 85, and a $V_L$ comprising LC-CDR1, LC-CDR2 and LC-CDR3 of the $V_L$ of SEQ ID NO: 117. In some embodiments, the anti-C5a antibody comprises a $V_H$ comprising HC-CDR1, HC-CDR2 and HC-CDR3 of the $V_H$ of SEQ ID NO: 88, and a $V_L$ comprising LC-CDR1, LC-CDR2 and LC-CDR3 of the $V_L$ of SEQ ID NO: 126. In some embodiments, the anti-C5a antibody comprises a $V_H$ comprising HC-CDR1, HC-CDR2 and HC-CDR3 of the $V_H$ of SEQ ID NO: 93, and a $V_L$ comprising LC-CDR1, LC-CDR2 and LC-CDR3 of the $V_L$ of SEQ ID NO: 116. In some embodiments, the anti-C5a antibody comprises a $V_H$ comprising HC-CDR1, HC-CDR2 and HC-CDR3 of the $V_H$ of SEQ ID NO: 97, and a $V_L$ comprising LC-CDR1, LC-CDR2 and LC-CDR3 of the $V_L$ of SEQ ID NO: 116. In some embodiments, the anti-C5a antibody comprises a $V_H$ comprising HC-CDR1, HC-CDR2 and HC-CDR3 of the $V_H$ of SEQ ID NO: 77, and a $V_L$ comprising LC-CDR1, LC-CDR2 and LC-CDR3 of the $V_L$ of SEQ ID NO: 132. In some embodiments, the anti-C5a antibody comprises a $V_H$ comprising HC-CDR1, HC-CDR2 and HC-CDR3 of the $V_H$ of SEQ ID NO: 102, and a $V_L$ comprising LC-CDR1, LC-CDR2 and LC-CDR3 of the $V_L$ of SEQ ID NO: 135. In some embodiments, the anti-C5a antibody comprises a $V_H$ comprising HC-CDR1, HC-CDR2 and HC-CDR3 of the $V_H$ of SEQ ID NO: 109, and a $V_L$ comprising LC-CDR1, LC-CDR2 and LC-CDR3 of the $V_L$ of SEQ ID NO: 138. In some embodiments, the anti-C5a antibody comprises a $V_H$ comprising HC-CDR1, HC-CDR2 and HC-CDR3 of the $V_H$ of SEQ ID NO: 110, and a $V_L$ comprising LC-CDR1, LC-CDR2 and LC-CDR3 of the $V_L$ of SEQ ID NO: 139. In some embodiments, the anti-C5a antibody comprises a $V_H$ comprising HC-CDR1, HC-CDR2 and HC-CDR3 of the $V_H$ of SEQ ID NO: 110, and a $V_L$ comprising LC-CDR1, LC-CDR2 and LC-CDR3 of the $V_L$ of SEQ ID NO: 140. In some embodiments, the anti-C5a antibody comprises a $V_H$ comprising HC-CDR1, HC-CDR2 and HC-CDR3 of the $V_H$ of SEQ ID NO: 111, and a $V_L$ comprising LC-CDR1, LC-CDR2 and LC-CDR3 of the $V_L$ of SEQ ID NO: 139. In some embodiments, the anti-C5a antibody comprises a $V_H$ comprising HC-CDR1, HC-CDR2 and HC-CDR3 of the $V_H$ of SEQ ID NO: 111, and a $V_L$ comprising LC-CDR1, LC-CDR2 and LC-CDR3 of the $V_L$ of SEQ ID NO: 140.

In some embodiments, the anti-C5a antibody comprises a $V_H$ comprising the amino acid sequence of any one of SEQ ID NOs: 73-111, or a variant thereof having at least about 90% (for example at least about any of 91%, 92%, 93%, 94%, 95%, 96%, 97%, 98%, or 99%) sequence identity, and a $V_L$ comprising the amino acid sequence of any one of SEQ ID NOs: 112-140, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of any one of SEQ ID NOs: 73-111, and a $V_L$ comprising the amino acid sequence of any one of SEQ ID NOs: 112-140.

In some embodiments, the anti-C5a antibody comprises a $V_H$ comprising the amino acid sequence of SEQ ID NO: 73, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 112, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 73 and a $V_L$ comprising the amino acid sequence of SEQ ID NO: 112.

In some embodiments, the anti-C5a antibody comprises a $V_H$ comprising the amino acid sequence of SEQ ID NO: 75, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 114, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 75 and a $V_L$ comprising the amino acid sequence of SEQ ID NO: 114.

In some embodiments, the anti-C5a antibody comprises a $V_H$ comprising the amino acid sequence of SEQ ID NO: 100, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 135, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 100 and a $V_L$ comprising the amino acid sequence of SEQ ID NO: 135.

In some embodiments, the anti-C5a antibody comprises a $V_H$ comprising the amino acid sequence of SEQ ID NO: 79, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 118, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 79 and a $V_L$ comprising the amino acid sequence of SEQ ID NO: 118.

In some embodiments, the anti-C5a antibody comprises a $V_H$ comprising the amino acid sequence of SEQ ID NO: 85, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 117, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 85 and a $V_L$ comprising the amino acid sequence of SEQ ID NO: 117.

In some embodiments, the anti-C5a antibody comprises a $V_H$ comprising the amino acid sequence of SEQ ID NO: 88, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 126, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 88 and a $V_L$ comprising the amino acid sequence of SEQ ID NO: 126.

In some embodiments, the anti-C5a antibody comprises a $V_H$ comprising the amino acid sequence of SEQ ID NO: 93, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 116, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 93 and a $V_L$ comprising the amino acid sequence of SEQ ID NO: 116.

In some embodiments, the anti-C5a antibody comprises a $V_H$ comprising the amino acid sequence of SEQ ID NO: 97, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 116, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 97 and a $V_L$ comprising the amino acid sequence of SEQ ID NO: 116.

In some embodiments, the anti-C5a antibody comprises a $V_H$ comprising the amino acid sequence of SEQ ID NO: 77, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 132, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 77 and a $V_L$ comprising the amino acid sequence of SEQ ID NO: 132.

In some embodiments, the anti-C5a antibody comprises a $V_H$ comprising the amino acid sequence of SEQ ID NO: 102, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 135, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 102 and a $V_L$ comprising the amino acid sequence of SEQ ID NO: 135.

In some embodiments, the anti-C5a antibody comprises a $V_H$ comprising the amino acid sequence of SEQ ID NO: 109, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 138, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 109 and a $V_L$ comprising the amino acid sequence of SEQ ID NO: 138.

In some embodiments, the anti-C5a antibody comprises a $V_H$ comprising the amino acid sequence of SEQ ID NO: 110, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 139, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 110 and a $V_L$ comprising the amino acid sequence of SEQ ID NO: 139.

In some embodiments, the anti-C5a antibody comprises a $V_H$ comprising the amino acid sequence of SEQ ID NO: 110, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 140, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 110 and a $V_L$ comprising the amino acid sequence of SEQ ID NO: 140.

In some embodiments, the anti-C5a antibody comprises a $V_H$ comprising the amino acid sequence of SEQ ID NO: 111, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 139, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 111 and a $V_L$ comprising the amino acid sequence of SEQ ID NO: 139.

In some embodiments, the anti-C5a antibody comprises a $V_H$ comprising the amino acid sequence of SEQ ID NO: 111, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 140, or a variant thereof having at least about 90% (for example at least about any of 91%, 92%, 93%, 94%, 95%, 96%, 97%, 98%, or 99%) sequence identity. In some embodiments, the anti-C5a antibody comprises a $V_H$ comprising the amino acid sequence of SEQ ID NO: 111 and a $V_L$ comprising the amino acid sequence of SEQ ID NO: 140.

In some embodiments, functional epitopes can be mapped by combinatorial alanine scanning. In this process, a combinatorial alanine-scanning strategy can be used to identify amino acids in the C5a protein that are necessary for interaction with C5a antibodies. In some embodiments, the epitope is conformational and crystal structure of anti-C5a antibodies bound to C5a may be employed to identify the epitopes.

In some embodiments, the present application provides antibodies which compete with any one of the C5a antibodies described herein for binding to C5a. In some embodiments, the present application provides antibodies which compete with any one of the anti-C5a antibodies provided herein for binding to an epitope on the C5a. In some embodiments, an anti-C5a antibody is provided that binds to the same epitope as an anti-C5a antibody comprising a $V_H$ comprising the amino acid sequence of any one of SEQ ID NOs: 73-111, and a $V_L$ comprising the amino acid sequence of any one of SEQ ID NOs: 112-140. In some embodiments, an anti-C5a antibody is provided that specifically binds to C5a competitively with an anti-C5a antibody comprising a $V_H$ comprising the amino acid sequence of any one of SEQ ID NOs: 73-111, and a $V_L$ comprising the amino acid sequence of any one of SEQ ID NOs: 112-140.

In some embodiments, competition assays may be used to identify a monoclonal antibody that competes with an anti-C5a antibody described herein for binding to C5a. Competition assays can be used to determine whether two antibodies bind the same epitope by recognizing identical or sterically overlapping epitopes or one antibody competitively inhibits binding of another antibody to the antigen. In certain embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-C5a antibody described herein is a chimeric, humanized or human antibody.

Exemplary anti-C5a antibody sequences are shown in Tables 2 and 3, wherein the CDR numbering is according to the EU index of Kabat. Those skilled in the art will recognize that many algorithms are known for prediction of CDR positions and for delimitation of antibody heavy chain and light chain variable regions. Anti-C5a antibodies comprising CDRs, $V_H$ and/or $V_L$ sequences from antibodies described herein, but based on prediction algorithms other than those exemplified in the tables below, are within the scope of this invention.

TABLE 2

Exemplary anti-C5a antibody CDR sequences.

| Antibody Name | HC-CDR1 | HC-CDR2 | HC-CDR3 |
|---|---|---|---|
| Cab01 | KYYMQ (SEQ ID NO: 1) | LIRNKANGGTAEYVASVKD (SEQ ID NO: 7) | RDNGYH (SEQ ID NO: 30) |
| Cab02 | DYYMQ (SEQ ID NO: 2) | LIRKKVNGGTTEYAASVKG (SEQ ID NO: 8) | RAGPPGLT (SEQ ID NO: 31) |
| Cab03 | DYYMQ (SEQ ID NO: 2) | LIRKKVNGGTTEYAASVKG (SEQ ID NO: 8) | RAGPPGLT (SEQ ID NO: 31) |
| Cab04 | DYYMQ (SEQ ID NO: 2) | LIRNKAIGGTTQYAASVKG (SEQ ID NO: 9) | RAGPPGLS (SEQ ID NO: 32) |
| Cab05 | DYYMQ (SEQ ID NO: 2) | LIRNKAVGGTTQYAASVKG (SEQ ID NO: 10) | RAGPPGLS (SEQ ID NO: 32) |
| Cab06 | DYYMQ (SEQ ID NO: 2) | LIRKKVNGGTTEYAASVKG (SEQ ID NO: 8) | RAGPPGLT (SEQ ID NO: 31) |
| Cab07 | DYYMQ (SEQ ID NO: 2) | LIRNKAIGETTEYAASVKG (SEQ ID NO: 11) | RAGPPGLS (SEQ ID NO: 32) |
| Cab08 | DYYLQ (SEQ ID NO: 3) | LIRTKRYGGTSEYAASVKG (SEQ ID NO: 12) | RIFTGLH (SEQ ID NO: 33) |
| Cab09 | DYYMQ (SEQ ID NO: 2) | LIRKKVNGGTTEYAASVKG (SEQ ID NO: 8) | RAGPPGLT (SEQ ID NO: 31) |
| Cab10 | DYYMQ (SEQ ID NO: 2) | LIRKKVNGGTTEYAASVKG (SEQ ID NO: 8) | RAGPPGLT (SEQ ID NO: 31) |
| Cab11 | DFYMQ (SEQ ID NO: 4) | LIRNKPYGGTAEYAASVKG (SEQ ID NO: 13) | RNNGYH (SEQ ID NO: 34) |
| Cab12 | DYYMQ (SEQ ID NO: 2) | LIRNKAIGETTQYAASVKG (SEQ ID NO: 14) | RAGPPGLS (SEQ ID NO: 32) |
| Cab13 | DYYMQ (SEQ ID NO: 2) | LIRNKAIGGTTQYAASVKG (SEQ ID NO: 9) | RAGPPGLS (SEQ ID NO: 32) |
| Cab14 | DYYMQ (SEQ ID NO: 2) | LIRNKAIGGTTQYAASVKG (SEQ ID NO: 9) | RAGPPGLS (SEQ ID NO: 32) |
| Cab15 | DYYMQ (SEQ ID NO: 2) | LIRNKAIGETTEYAASVKG (SEQ ID NO: 11) | RLGPPGLS (SEQ ID NO: 35) |
| Cab16 | DYYMQ (SEQ ID NO: 2) | LIRNKAIGETTEYAASVKG (SEQ ID NO: 11) | RLGPPGLS (SEQ ID NO: 35) |
| Cab17 | DYYIQ (SEQ ID NO: 5) | LIRNKAVGETVQYAASLKG (SEQ ID NO: 15) | RAGPPGLT (SEQ ID NO: 31) |

TABLE 2-continued

| Exemplary anti-C5a antibody CDR sequences. | | | |
|---|---|---|---|
| Cab18 | DYYMQ (SEQ ID NO: 2) | LIRNKAIGETTQYAASVKG (SEQ ID NO: 14) | RAGPPGLS (SEQ ID NO: 32) |
| Cab19 | DYYIQ (SEQ ID NO: 5) | LIRNKAVGGTTSYAASVKG (SEQ ID NO: 16) | RAGPPGLS (SEQ ID NO: 32) |
| Cab20 | DYYMQ (SEQ ID NO: 2) | LIRNKAIGETAEYAASVKG (SEQ ID NO: 17) | RAGPPGLS (SEQ ID NO: 32) |
| Cab21 | NYYIQ (SEQ ID NO: 6) | LIRNKAIGETTEFAASVKG (SEQ ID NO: 18) | RLGPPGLT (SEQ ID NO: 36) |
| Cab22 | DYYMQ (SEQ ID NO: 2) | LIRNKANGGTTEYAASVKG (SEQ ID NO: 19) | RLGPPGLT (SEQ ID NO: 36) |
| Cab23 | DYYIQ (SEQ ID NO: 5) | LIRNKAIGGTVEYAASVKG (SEQ ID NO: 20) | RVGPPGLT (SEQ ID NO: 37) |
| Cab24 | DYYMQ (SEQ ID NO: 2) | LIRKKVNGGTTEYAASVKG (SEQ ID NO: 8) | RAGPPGLA (SEQ ID NO: 38) |
| Cab25 | DYYIQ (SEQ ID NO: 5) | LIRNKAVGGTTTYAASVKG (SEQ ID NO: 21) | RAGPPGLS (SEQ ID NO: 32) |
| Cab26 | DYYIQ (SEQ ID NO: 5) | LIRNKAVGETVQYAASLKG (SEQ ID NO: 15) | RAGPPGLT (SEQ ID NO: 31) |
| Cab27 | DYYMQ (SEQ ID NO: 2) | LIRNKAIGGTTQYAASVKG (SEQ ID NO: 9) | RAGPPGLS (SEQ ID NO: 32) |
| Cab28 | DYYMQ (SEQ ID NO: 2) | LIRNKAVGGTTQYAASVKG (SEQ ID NO: 10) | RAGPPGLS (SEQ ID NO: 32) |
| Cab29 | DYYMQ (SEQ ID NO: 2) | LIRNKAVGGTTQYAASVKG (SEQ ID NO: 10) | RAGPPGLS (SEQ ID NO: 32) |
| Cab30 | DYYMQ (SEQ ID NO: 2) | LIRNKAVGGTTQYAASVKG (SEQ ID NO: 10) | RAGPPGLS (SEQ ID NO: 32) |
| Cab31 | DYYMQ (SEQ ID NO: 2) | LIRNKAVGGTTQYAASVKG (SEQ ID NO: 10) | RAGPPGLS (SEQ ID NO: 32) |
| Cab32 | DYYMQ (SEQ ID NO: 2) | LIRNKAVGGTTQYAASVKG (SEQ ID NO: 10) | RAGPPGLS (SEQ ID NO: 32) |
| Cab33 | DYYMQ (SEQ ID NO: 2) | LIRNKAVGGTTQYAASVKG (SEQ ID NO: 10) | RAGPPGLS (SEQ ID NO: 32) |
| Cab34 | DYYMQ (SEQ ID NO: 2) | LIRNKAVGGTTEYAASVKG (SEQ ID NO: 22) | RAGPPGLS (SEQ ID NO: 32) |
| Cab35 | DYYMQ (SEQ ID NO: 2) | LIRNKAVGETTQYAASVKG (SEQ ID NO: 23) | RAGPPGLS (SEQ ID NO: 32) |
| Cab36 | DYYMQ (SEQ ID NO: 2) | LIRNKAVGETTEYAASVKG (SEQ ID NO: 24) | RAGPPGLS (SEQ ID NO: 32) |

TABLE 2-continued

Exemplary anti-C5a antibody CDR sequences.

| | | | |
|---|---|---|---|
| Cab37 | DYYMQ (SEQ ID NO: 2) | LIRNKAVGFTTQYAASVKG (SEQ ID NO: 25) | RAGPPGLS (SEQ ID NO: 32) |
| Cab38 | DYYMQ (SEQ ID NO: 2) | LIRNKAVGHTTQYAASVKG (SEQ ID NO: 26) | RAGPPGLS (SEQ ID NO: 32) |
| Cab39 | DYYMQ (SEQ ID NO: 2) | LIRNKAVGITTQYAASVKG (SEQ ID NO: 27) | RAGPPGLS (SEQ ID NO: 32) |
| Cab40 | DYYMQ (SEQ ID NO: 2) | LIRNKAVGQTTQYAASVKG (SEQ ID NO: 28) | RAGPPGLS (SEQ ID NO: 32) |
| Cab41 | DYYMQ (SEQ ID NO: 2) | LIRNKAVGRTTQYAASVKG (SEQ ID NO: 29) | RAGPPGLS (SEQ ID NO: 32) |
| Cab42 | DYYMQ (SEQ ID NO: 2) | LIRNKAVGETTQYAASVKG (SEQ ID NO: 23) | RAGPPGLS (SEQ ID NO: 32) |
| Cab43 | NYYIQ (SEQ ID NO: 6) | LIRNKAIGETTEFAASVKG (SEQ ID NO: 18) | RLGPPGLT (SEQ ID NO: 36) |
| Cab44 | NYYIQ (SEQ ID NO: 6) | LIRNKAIGETTEFAASVKG (SEQ ID NO: 18) | RLGPPGLT (SEQ ID NO: 36) |
| Cab45 | DYYIQ (SEQ ID NO: 5) | LIRNKAVGGTTTYAASVKG (SEQ ID NO: 21) | RAGPPGLS (SEQ ID NO: 32) |
| Cab46 | DYYIQ (SEQ ID NO: 5) | LIRNKAVGGTTTYAASVKG (SEQ ID NO: 21) | RAGPPGLS (SEQ ID NO: 32) |

| Antibody Name | LC-CDR1 | LC-CDR2 | LC-CDR3 |
|---|---|---|---|
| Cab01 | RSSQRLLHSDGYTYLD (SEQ ID NO: 39) | GGSNRAS (SEQ ID NO: 57) | MQHKALPLT (SEQ ID NO: 60) |
| Cab02 | RSSQRLLHSDGYTYLD (SEQ ID NO: 39) | GGSNRAS (SEQ ID NO: 57) | MQHKALPLT (SEQ ID NO: 60) |
| Cab03 | RSSQSLLASDGYTYLD (SEQ ID NO: 40) | GGSNRAS (SEQ ID NO: 57) | LQHRALPPT (SEQ ID NO: 61) |
| Cab04 | RSSQRLLHTDGYTYLD (SEQ ID NO: 41) | GGSNRAS (SEQ ID NO: 57) | LQHKALPLT (SEQ ID NO: 62) |
| Cab05 | RSSQSLLASDGYNYID (SEQ ID NO: 42) | GGSNRAS (SEQ ID NO: 57) | LQHRALPPT (SEQ ID NO: 61) |
| Cab06 | RSSQSLLASDGYNYMD (SEQ ID NO: 43) | GGSNRAS (SEQ ID NO: 57) | MQHKVLPPT (SEQ ID NO: 63) |
| Cab07 | RSSQRLLHTDGYTYLD (SEQ ID NO: 41) | GGSNRAS (SEQ ID NO: 57) | MQHKALPPT (SEQ ID NO: 64) |
| Cab08 | RSSQSLLHTDGYTYLD (SEQ ID NO: 44) | GGSNRAS (SEQ ID NO: 57) | MQHKALPLT (SEQ ID NO: 60) |
| Cab09 | RSSQSLLHSDGYTYVD (SEQ ID NO: 45) | GGSNRAS (SEQ ID NO: 57) | LQHKALPPT (SEQ ID NO: 65) |

TABLE 2-continued

Exemplary anti-C5a antibody CDR sequences.

| | | | |
|---|---|---|---|
| Cab10 | RSSQSLLHTDGY IYLD (SEQ ID NO: 46) | GGSNRAS (SEQ ID NO: 57) | MQHKALPLT (SEQ ID NO: 60) |
| Cab11 | RSSQSLLHTDGY TYLD (SEQ ID NO: 44) | GGSNRAS (SEQ ID NO: 57) | MQHKALPPT (SEQ ID NO: 64) |
| Cab12 | RSSQRLLHSDG YTYMD (SEQ ID NO: 47) | GGSNRAS (SEQ ID NO: 57) | MQHKALPPT (SEQ ID NO: 64) |
| Cab13 | RSSQSLLASDGY NYMD (SEQ ID NO: 43) | GGSNRAS (SEQ ID NO: 57) | MQHKVLPPT (SEQ ID NO: 63) |
| Cab14 | RSSQSLLHTDGY TYLD (SEQ ID NO: 44) | GGSNRAS (SEQ ID NO: 57) | MQHKALPLT (SEQ ID NO: 60) |
| Cab15 | RSSQSLLATDGY TYLD (SEQ ID NO: 48) | GGSKRAS (SEQ ID NO: 58) | MQHKALPPT (SEQ ID NO: 64) |
| Cab16 | RSSQSLLHTDGY TYLD (SEQ ID NO: 44) | GGSNRAS (SEQ ID NO: 57) | MQHKALPLT (SEQ ID NO: 60) |
| Cab17 | RSSQRLLASDG YTYVD (SEQ ID NO: 49) | GGSNRAS (SEQ ID NO: 57) | MQHKALPPT (SEQ ID NO: 64) |
| Cab18 | RSSQSLLDSNRY AYVD (SEQ ID NO: 50) | GGSNRAS (SEQ ID NO: 57) | MQHKVLPPT (SEQ ID NO: 63) |
| Cab19 | RSSQSLLHSDGY TYLD (SEQ ID NO: 51) | GGSNRAS (SEQ ID NO: 57) | MQHKALPPT (SEQ ID NO: 64) |
| Cab20 | RSSQSLLHSDGY TYLD (SEQ ID NO: 51) | GGSNRAS (SEQ ID NO: 57) | MQHKVLPLT (SEQ ID NO: 66) |
| Cab21 | RSSQSLLASDGY NYID (SEQ ID NO: 42) | GGSNRAS (SEQ ID NO: 57) | LQHRALPPT (SEQ ID NO: 61) |
| Cab22 | RSSQSLLASDGY NYID (SEQ ID NO: 42) | GGSNRAS (SEQ ID NO: 57) | LQHRALPPT (SEQ ID NO: 61) |
| Cab23 | RSSQSLLASDGY NYID (SEQ ID NO: 42) | GGSNRAS (SEQ ID NO: 57) | LQHRALPPT (SEQ ID NO: 61) |
| Cab24 | RSSQSLLASDGY NYID (SEQ ID NO: 42) | GGSNRAS (SEQ ID NO: 57) | LQHRALPPT (SEQ ID NO: 61) |
| Cab25 | RSSQSLLASDGY NYID (SEQ ID NO: 42) | GGSNRAS (SEQ ID NO: 57) | LQHRALPPT (SEQ ID NO: 61) |
| Cab26 | RSSQSLLASDGY NYID (SEQ ID NO: 42) | GGSNRAS (SEQ ID NO: 57) | LQHRALPPT (SEQ ID NO: 61) |
| Cab27 | RSSQSLLASDGY NYID (SEQ ID NO: 42) | GGSNRAS (SEQ ID NO: 57) | LQHRALPPT (SEQ ID NO: 61) |
| Cab28 | RSSQNLLATDG YTYLD (SEQ ID NO: 52) | GGSKRAS (SEQ ID NO: 58) | LQHRALPPT (SEQ ID NO: 61) |

TABLE 2-continued

| Exemplary anti-C5a antibody CDR sequences. | | | |
|---|---|---|---|
| Cab29 | RSSQSLLATDGY EYLD (SEQ ID NO: 53) | GASNRAS (SEQ ID NO: 59) | LQHKALPPT (SEQ ID NO: 65) |
| Cab30 | RSSQSLLHSDGY TYLD (SEQ ID NO: 51) | GGSNRAS (SEQ ID NO: 57) | MQHKVLPPT (SEQ ID NO: 63) |
| Cab31 | RSSQSLLHSDGY TYMD (SEQ ID NO: 54) | GGSNRAS (SEQ ID NO: 57) | MQHKVLPPT (SEQ ID NO: 63) |
| Cab32 | RSSQSLLASDGY IYID (SEQ ID NO: 55) | GGSNRAS (SEQ ID NO: 57) | LQHRALPPT (SEQ ID NO: 61) |
| Cab33 | RSSQSLLASDGY NYID (SEQ ID NO: 42) | GGSNRAS (SEQ ID NO: 57) | LQHKALPPT (SEQ ID NO: 65) |
| Cab34 | RSSQSLLASDGY NYID (SEQ ID NO: 42) | GGSNRAS (SEQ ID NO: 57) | LQHRALPPT (SEQ ID NO: 61) |
| Cab35 | RSSQSLLASDGY NYID (SEQ ID NO: 42) | GGSNRAS (SEQ ID NO: 57) | LQHRALPPT (SEQ ID NO: 61) |
| Cab36 | RSSQSLLASDGY NYID (SEQ ID NO: 42) | GGSNRAS (SEQ ID NO: 57) | LQHRALPPT (SEQ ID NO: 61) |
| Cab37 | RSSQSLLASDGY NYID (SEQ ID NO: 42) | GGSNRAS (SEQ ID NO: 57) | LQHRALPPT (SEQ ID NO: 61) |
| Cab38 | RSSQSLLASDGY NYID (SEQ ID NO: 42) | GGSNRAS (SEQ ID NO: 57) | LQHRALPPT (SEQ ID NO: 61) |
| Cab39 | RSSQSLLASDGY NYID (SEQ ID NO: 42) | GGSNRAS (SEQ ID NO: 57) | LQHRALPPT (SEQ ID NO: 61) |
| Cab40 | RSSQSLLASDGY NYID (SEQ ID NO: 42) | GGSNRAS (SEQ ID NO: 57) | LQHRALPPT (SEQ ID NO: 61) |
| Cab41 | RSSQSLLASDGY NYID (SEQ ID NO: 42) | GGSNRAS (SEQ ID NO: 57) | LQHRALPPT (SEQ ID NO: 61) |
| Cab42 | RSSQSLLASDAY NYID (SEQ ID NO: 56) | GGSNRAS (SEQ ID NO: 57) | LQHRALPPT (SEQ ID NO: 61) |
| Cab43 | RSSQNLLATDG YTYLD (SEQ ID NO: 52) | GGSKRAS (SEQ ID NO: 58) | LQHRALPPT (SEQ ID NO: 61) |
| Cab44 | RSSQSLLATDGY EYLD (SEQ ID NO: 53) | GASNRAS (SEQ ID NO: 59) | LQHKALPPT (SEQ ID NO: 65) |
| Cab45 | RSSQNLLATDG YTYLD (SEQ ID NO: 52) | GGSKRAS (SEQ ID NO: 58) | LQHRALPPT (SEQ ID NO: 61) |
| Cab46 | RSSQSLLATDGY EYLD (SEQ ID NO: 53) | GASNRAS (SEQ ID NO: 59) | LQHKALPPT (SEQ ID NO: 65) |

TABLE 3

| Exemplary sequences. | |
|---|---|
| Description | Sequence |
| Cab01 $V_H$ | EVQLVESGGGMVQPGGSLRVSCAASGFTFTKYYMQWVRQAPGK GPEWVGLIRNKANGGTA EYVASVKDRFTISRDDSKSIAYLQMSSLKTEDTAVYYCVMRDNGY HWGQGVLVTVSS (SEQ ID NO: 73) |
| Cab02 $V_H$ | EVQLVESGGGLVQPGGSLKVSCAASGFIFSDYYMQWVRQAPGKG PEWVGLIRKKVNGGTT EYAASVKGRFTISRDDSKSIAYLQMSSLKIEDTAVYYCVSRAGPPG LTWGQGVLVTISS (SEQ ID NO: 74) |
| Cab03 $V_H$ | EVQLVESGGGLVQPGGSLKVSCAASGFIFSDYYMQWVRQAPGKG PEWVGLIRKKVNGGTT EYAASVKGRFTISRDDSKSIVYLQMSSLKIEDTAVYYCVSRAGPPG LTWGQGVLVTVSS (SEQ ID NO: 75) |
| Cab04 $V_H$ | EVQLVQSGGGLVQPGGSLKVSCAASGFTFSDYYMQWVRQAPGKG PEWVGLIRNKAIGGTT QYAASVKGRFTISRDDSKSIVYLQMSSLKTEDTAVYYCVSRAGPPG LSWGQGVVVTVSS (SEQ ID NO: 76) |
| Cab28 $V_H$ Cab29 $V_H$ Cab30 $V_H$ Cab31 $V_H$ | DMQLVESGGGLVQPGGSLKVSCAASGFTFSDYYMQWVRQAPGK GPEWVGLIRNKAVGGTT QYAASVKGRFTISRDDSKSIVYLEMSSLKTEDTAVYYCVSRAGPPG LSWGQGVLVTVSS (SEQ ID NO: 77) |
| Cab06 $V_H$ | EVHLVESGGGLVQPGGSLKVSCAASGFIFSDYYMQWVRQAPGKG PEWVGLIRKKVNGGTT EYAASVKGRFTISRDDSKSIVYLQMSSLKIEDTAVYYCVSRAGPPG LTWGQGVLVTISS (SEQ ID NO: 78) |
| Cab07 $V_H$ | DVQLVESGGGLVQPGGSLKVSCAASGFTFSDYYMQWVRQAPGKG PEWVGLIRNKAIGETT EYAASVKGRFTISRDDSKSIVYLQMSSLKTEDTAVYYCVSRAGPPG LSWGQGVLVTISS (SEQ ID NO: 79) |
| Cab08 $V_H$ | EVQLVESGGGLIQPGGSLRVSCAASGFTFSDYYLQWVRQAPGKGP EWVGLIRTKRYGGTS EYAASVKGRYTISRDDSKAIAYLQMSSLKTEDTAVYYCVVRIFTGL HWGKGTPVTVSS (SEQ ID NO: 80) |
| Cab09 $V_H$ | EVQLVESGGGLVQPGGSLKVSCAASGFIFSDYYMQWVRQAPGKG PEWVGLIRKKVNGGTT EYAASVKGRFTISRDDSKSIAYLQMSSLKIEDTAVYYCVSRAGPPG LTWGQGVLVTISS (SEQ ID NO: 81) |
| Cab10 $V_H$ | QVQLVESGGGLVQPGGSLKVSCAASGFIFSDYYMQWVRQAPGKG PEWVGLIRKKVNGGTT EYAASVKGRFTISRDDSKSIVYLQMSSLKIEDTAVYYCVSRAGPPG LTWGQGVLITVSS (SEQ ID NO: 82) |
| Cab11 $V_H$ | EVQLVESGGGLVQPGGSLRVSCAASGFRFSDFYMQWVRQAPGKR PEWVGLIRNKPYGGTA EYAASVKGRFTISRDDSKSVTDLQMSSLKTEDTAIYYCVMRNNGY HWGQGVLVTISS (SEQ ID NO: 83) |
| Cab12 $V_H$ | VVQLVESGGGLVQPGGSLKVSCAASGFTFSDYYMQWVRQAPGKG PEWVGLIRNKAIGETT QYAASVKGRFTISRDDSKSIVYLQMSSLKTEDTAVYYCVSRAGPPG LSWGQGVLVTISS (SEQ ID NO: 84) |

TABLE 3-continued

| Exemplary sequences. | |
|---|---|
| Description | Sequence |
| Cab13 $V_H$ | VVQLVESGGGLVQPGGSLKVSCAASGFTFSDYYMQWVRQAPGKG PEWVGLIRNKAIGGTT QYAASVKGRFTISRDDSKSIVYLQMSSLKTEDTAVYYCVSRAGPPG LSWGQGVLVTISS (SEQ ID NO: 85) |
| Cab14 $V_H$ | VVQLVESGGGLVQPGGSLKVSCATSGFTFSDYYMQWVRQAPGKG PEWLGLIRNKAIGGTT QYAASVKGRFTISRDDSKGIAYLQMSSLKTEDTAVYYCVCRAGPP GLSWGQGVLVTVSS (SEQ ID NO: 86) |
| Cab15 $V_H$ | VVQLVESGGGLVQPGGSLKVSCAASGFTFSDYYMQWVRQAPGKG PEWVGLIRNKAIGETT EYAASVKGRFTISRDDSKSIVYLQMSSLKPEDTAVYYCAGRLGPPG LSWGQGVLVTVSS (SEQ ID NO: 87) |
| Cab16 $V_H$ | EVHLVESGGGLVQPGGSLKVSCAASGFTFSDYYMQWVRQAPGKG PEWVGLIRNKAIGETT EYAASVKGRFTISRDDSKSIVYLQMSSLKPEDTAVYYCAGRLGPPG LSWGQGVLVTVSS (SEQ ID NO: 88) |
| Cab17 $V_H$ | VVQLVESGGGLVLPGGSLKVSCAASGFIFSDYYIQWVRQAPGKGP EWVGLIRNKAVGETV QYAASLKGRFTISRDDSKSIAYLQMTSLKTEDTAMYYCVSRAGPP GLTWGQGVLVTVSS (SEQ ID NO: 89) |
| Cab18 $V_H$ | VVQLVESGGGLVQPGGSLKVSCAASGFTFSDYYMQWVRQAPGKG PEWVGLIRNKAIGETT QYAASVKGRFTISRDDSKSIVYLQMSSLKTEDTAVYYCVSRAGPPG LSWGQGVLVTVSS (SEQ ID NO: 90) |
| Cab19 $V_H$ | EVQLVESGGGLVQPGGSLKVSCVASGFTFSDYYIQWVRQAPGKGP EWVGLIRNKAVGGTT SYAASVKGRFTISRDDSKSVAYLQMTSLKTEDTAVYFCVSRAGPPG LSWGQGVLVTVSS (SEQ ID NO: 91) |
| Cab20 $V_H$ | EVQLVESGGGLVQPGGSLKVSCAASGFTFRDYYMQWVRQAPGKG PEWVGLIRNKAIGETA EYAASVKGRFTISRDDSKSIVYLQMSSLKTEDTAVYYCTSRAGPPG LSWGQGVLVTVSS (SEQ ID NO: 92) |
| Cab21 $V_H$ | EVQLVQSGGGLVQPGGSLKVSCAASGFIFSNYYIQWVRQAPGKGP EWVGLIRNKAIGETT EFAASVKGRFTISRDDSKSIVYLQMTRLKTEDTAVYYCAGRLGPPG LTWGQGVLVTISS (SEQ ID NO: 93) |
| Cab22 $V_H$ | VVQLVESGGGLVQPGGSLKVSCTASGFIFNDYYMQWVRQAPGKG PEWVGLIRNKANGGTT EYAASVKGRFTISRDDSKSIVYLQMSSLKTEDTAVYFCTGRLGPPG LTWGQGVLVTISS (SEQ ID NO: 94) |
| Cab23 $V_H$ | EVQLVESGGGLVQPGGSLRLSCAASGFTFSDYYIQWVRQAPGKGP EWVGLIRNKAIGGTV EYAASVKGRFTISRDDSKRIAYLQMRSLKTEDTAVYFCTGRVGPPG LTWGQGVLVTISS (SEQ ID NO: 95) |
| Cab24 $V_H$ | VVQLVESGGGLVQPGGSLKVSCAASGFIFSDYYMQWVRQAPGKG PEWVGLIRKKVNGGTT EYAASVKGRFTISRDDSKSIVYLQMSSLKIEDTAVYYCVSRAGPPG LAWGQGVLVTISS (SEQ ID NO: 96) |

TABLE 3-continued

Exemplary sequences.

| Description | Sequence |
|---|---|
| Cab25 $V_H$ | EVQLVESGGGFVQPGGSLKVSCVASGFTFSDYYIQWVRQAPGKGP EWVGLIRNKAVGGTT TYAASVKGRFTISRDDSKSVAYLQMTSLKTEDTAVYFCVSRAGPPG LSWGQGVLVTISS (SEQ ID NO: 97) |
| Cab26 $V_H$ | EVQLVESGGGLVLPGGSLKVSCAASGFIFSDYYIQWVRQAPGKGP EWVGLIRNKAVGETV QYAASLKGRFTISRDDSKSIAYLQMTSLKTEDTAMYYCVSRAGPP GLTWGQGVLVTISS (SEQ ID NO: 98) |
| Cab27 $V_H$ | EVQLVQSGGGLVQPGGSLKVSCAASGFTFRDYYMQWVRQAPGK GPEWVGLIRNKAIGGTT QYAASVKGRFTISRDDSKSIVYLQMSSLKTEDTAVYYCVSRAGPPG LSWGQGVLVTVSS (SEQ ID NO: 99) |
| Cab05 $V_H$<br>Cab32 $V_H$<br>Cab33 $V_H$ | EMQLVESGGGLVQPGGSLRLSCAASGFTFSDYYMQWVRQAPGKG PEWVGLIRNKAVGGTT QYAASVKGRFTISRDDSKNSVYLQMNSLKTEDTAVYYCVSRAGPP GLSWGQGVLVTVSS (SEQ ID NO: 100) |
| Cab34 $V_H$ | EMQLVESGGGLVQPGGSLRLSCAASGFTFSDYYMQWVRQAPGKG PEWVGLIRNKAVGGTT EYAASVKGRFTISRDDSKNSVYLQMNSLKTEDTAVYYCVSRAGPP GLSWGQGVLVTVSS (SEQ ID NO: 101) |
| Cab35 $V_H$ | EMQLVESGGGLVQPGGSLRLSCAASGFTFSDYYMQWVRQAPGKG PEWVGLIRNKAVGETT QYAASVKGRFTISRDDSKNSVYLQMNSLKTEDTAVYYCVSRAGPP GLSWGQGVLVTVSS (SEQ ID NO: 102) |
| Cab36 $V_H$ | EMQLVESGGGLVQPGGSLRLSCAASGFTFSDYYMQWVRQAPGKG PEWVGLIRNKAVGETT EYAASVKGRFTISRDDSKNSVYLQMNSLKTEDTAVYYCVSRAGPP GLSWGQGVLVTVSS (SEQ ID NO: 103) |
| Cab37 $V_H$ | EMQLVESGGGLVQPGGSLRLSCAASGFTFSDYYMQWVRQAPGKG PEWVGLIRNKAVGFTT QYAASVKGRFTISRDDSKNSVYLQMNSLKTEDTAVYYCVSRAGPP GLSWGQGVLVTVSS (SEQ ID NO: 104) |
| Cab38 $V_H$ | EMQLVESGGGLVQPGGSLRLSCAASGFTFSDYYMQWVRQAPGKG PEWVGLIRNKAVGHTT QYAASVKGRFTISRDDSKNSVYLQMNSLKTEDTAVYYCVSRAGPP GLSWGQGVLVTVSS (SEQ ID NO: 105) |
| Cab39 $V_H$ | EMQLVESGGGLVQPGGSLRLSCAASGFTFSDYYMQWVRQAPGKG PEWVGLIRNKAVGITT QYAASVKGRFTISRDDSKNSVYLQMNSLKTEDTAVYYCVSRAGPP GLSWGQGVLVTVSS (SEQ ID NO: 106) |
| Cab40 $V_H$ | EMQLVESGGGLVQPGGSLRLSCAASGFTFSDYYMQWVRQAPGKG PEWVGLIRNKAVGQTT QYAASVKGRFTISRDDSKNSVYLQMNSLKTEDTAVYYCVSRAGPP GLSWGQGVLVTVSS (SEQ ID NO: 107) |
| Cab41 $V_H$ | EMQLVESGGGLVQPGGSLRLSCAASGFTFSDYYMQWVRQAPGKG PEWVGLIRNKAVGRTT QYAASVKGRFTISRDDSKNSVYLQMNSLKTEDTAVYYCVSRAGPP GLSWGQGVLVTVSS (SEQ ID NO: 108) |

TABLE 3-continued

| Exemplary sequences. | |
|---|---|
| Description | Sequence |
| Cab42 $V_H$ | EMQLVESGGGLVQPGGSLRLSCAASGFTFSDYYMQWVRQAPGKG PEWVGLIRNKAVGETT QYAASVKGRFTISRDDSKNSVYLQMNSLKTEDTAVYYCVSRAGPP GLSWGQGVLVTVSS (SEQ ID NO: 109) |
| Cab43 $V_H$<br>Cab44 $V_H$ | EVQLVESGGGLVQPGGSLRLSCAASGFTFSNYYIQWVRQAPGKGP EWVGLIRNKAIGE TTEFAASVKGRFTISRDDSKNSVYLQMNSLKTEDTAVYYCAGRLG PPGLTWGQGVLVTVSS (SEQ ID NO: 110) |
| Cab45 $V_H$<br>Cab46 $V_H$ | EVQLVESGGGLVQPGGSLRLSCAASGFTFSDYYIQWVRQAPGKGP EWVGLIRNKAVGG TTTYAASVKGRFTISRDDSKNSAYLQMNSLKTEDTAVYFCVSRAG PPGLSWGQGVLVTVSS (SEQ ID NO: 111) |
| Cab01 $V_L$ | DIVLTQTPLSLPVTPGEPASISCRSSQRLLHSDGYTYLDWYLQKPG QSPQLLIYGGSNRASGVP DRFSGSGSGTDFTLKISKVEAEDVGVYYCMQHKALPLTFGGGTKV EIK (SEQ ID NO: 112) |
| Cab02 $V_L$ | DIVMIQTPLSLPVTPGEPASISCRSSQRLLHSDGYTYLDWYLQKPG QSPQLLIYGGSNRASGVP DRFSGSGSGTDFTLKISKVEAEDVGVYYCMQHKALPLTFGGGTKL EIK (SEQ ID NO: 113) |
| Cab03 $V_L$ | DIVLTQTPLSLAVSPGEPASISCRSSQSLL- ASDGYTYLDWYLQKPGQ SPQILIYGGSNRASGVP DRFSGRGSGTDFTLKITKVEAEDVGVYYCLQHRALPPTFGQGTKL EIK (SEQ ID NO: 114) |
| Cab04 $V_L$ | DIVMIQTPLSLPVTPGEPASISCRSSQRLLHTDGYTYLDWYLQKPG QSPQLLIYGGSNRASGVP DRFSGSGSGSDFTLKISKVEAEDVGVYYCLQHKALPLTFGGGTKL EIK (SEQ ID NO: 115) |
| Cab21 $V_L$<br>Cab22 $V_L$<br>Cab23 $V_L$<br>Cab24 $V_L$<br>Cab25 $V_L$<br>Cab26 $V_L$<br>Cab27 $V_L$ | DAVMTQTPLSLPVTPGEPASISCRSSQSLLASDGYNYIDWYLQRPG QSPKVLIYGGSNRASGVP DRFSGSGSGTYFTLKISKVEAEDVGFYFCLQHRALPPTFGQGTKLE IK (SEQ ID NO: 116) |
| Cab06 $V_L$<br>Cab13 $V_L$ | DIVMIQNPLSLPVTPGEPASISCRSSQSLLASDGYNYMDWYLQKPG QSPKVLIYGGSNRASGVP DRFSGSGSGTDFTLKITKVEAEDVGIYYCMQHKVLPPTFGQGTKL EIK (SEQ ID NO: 117) |
| Cab07 $V_L$ | DTVMTQIPLSLSVTPGEPASISCRSSQRLLHTDGYTYLDWYHQKPG QSPQLLIYGGSNRASGVP DRFSGSGSVTDFTLKISKMEAEDVGVYYCMQHKALPPTFGGGTKL EIK (SEQ ID NO: 118) |
| Cab08 $V_L$ | DIVMTQTPLSRPVTPGEPASISCRSSQSLLHTDGYTYLDWYLQKPG QSPQLLIYGGSNRASGVP DRFSGSGSGTDFTLKISKVEAEDVGVYYCMQHKALPLTFGGGTKL EIK (SEQ ID NO: 119) |
| Cab09 $V_L$ | DIVMIQTPLSLPVTPGEPASISCRSSQSLLHSDGYTYVDWYLQKPG QSPQILIYGGSNRASGVP DRFSGSGSGTDFTLKITNVEAEDVGVYYCLQHKALPPTFGQGTKL EIK (SEQ ID NO: 120) |

TABLE 3-continued

Exemplary sequences.

| Description | Sequence |
|---|---|
| Cab10 $V_L$ | DTVMSQIPLSLPVTPGEPASIS-CRSSQSLLHTDGYIYLDWYLQKPGQ SPQLLIYGGSNRASGVP DRFSGSGSGTDFTLKISKVEAEDVGVYYCMQHKALPLTFGGGTKL EIK (SEQ ID NO: 121) |
| Cab11 $V_L$ | DAVMTQIPLSLPVTPGEPASISCRSSQSLLHTDGYTYLDWYLQKPG QSPQLLIYGGSNRASGVP DRFSGSGSGTDFTLKISKVEAEDVGVYYCMQHKALPPTFGGGTKL EIK (SEQ ID NO: 122) |
| Cab12 $V_L$ | DIVLTQTPLSLPVTPGEPASISCRSSQRLLHSDGYTYMDWYLQKPG QSPQILIYGGSNRASGVP DRFSGSGSGTDFTLKISKVEAEDVGVYYCMQHKALPPTFGQGTKL EIK (SEQ ID NO: 123) |
| Cab14 $V_L$ | DIELTQTPLSRPVTPGEPASIS-CRSSQSLLHTDGYTYLDWYLQKPGQ SPQLLIYGGSNRASGVP DRFSGSGSGTDFTLKISKVEAEDVGVYYCMQHKALPLTFGGGTKL EIK (SEQ ID NO: 124) |
| Cab15 $V_L$ | DIVMTQNPLSLPVTPGEPASISCRSSQSLLATDGYTYLDWYLQKPG QSPQVLIYGGSKRASGVP DRFSGSGSGTDFTLKITKVEAEDVGIYYCMQHKALPPTFGQGTKL EIK (SEQ ID NO: 125) |
| Cab16 $V_L$ | DAVMTQIPLSLPVTPGEPASISCRSSQSLLHTDGYTYLDWYLQKPG QSPQLLIYGGSNRASGVP DRFSGSGSGTDFTLKISKVEAEDVGVYYCMQHKALPLTFGGGTRL EIK (SEQ ID NO: 126) |
| Cab17 $V_L$ | DIVMIQNPLSLSVTPGEPASISCRSSQRLLASDGYTYVDWYLQKPG QSPQILIYGGSNRASGVP DRFSGSGSGTDFTLKISKVEAEDVGVYYCMQHKALPPTFGQGTKL EIK (SEQ ID NO: 127) |
| Cab18 $V_L$ | DIVMTQNPLSLPVTPGEPASISCRSSQSLLDSNRYAYVDWYLQKPG QSPQILVYGGSNRASGVP DRFSGSGSGTDFTLKISKVEAEDVGIYYCMQHKVLPPTFGQGTKL EIK (SEQ ID NO: 128) |
| Cab19 $V_L$ | DIVMIQNPLSLPVTPGEPASISCRSSQSLLHSDGYTYLDWYQQKPG QAPQLLIYGGSNRASGVP DRFSGSGSATDFTLKISKMEAEDVGVYYCMQHKALPPTFGGGTKV EIK (SEQ ID NO: 129) |
| Cab20 $V_L$ | DIVMIQNPLSLPVTPGEPASISCRSSQSLLHSDGYTYLDWYLQKPG QSPQLLIYGGSNRASGVP DRFSGSGSGTDFTLKISKVEAEDVGVYYCMQHKVLPLTFAGGTKL EIK (SEQ ID NO: 130) |
| Cab28 $V_L$ | DIVMIQNPLSLPVTPGEPASISCRSSQNLLATDGYTYLDWYLQKPG QSPQVLIYGGSKRASGVP DRFSGSGSGTDFTLKISKVEAEDVGIYYCLQHRALPPTFGQGTKLE IK (SEQ ID NO: 131) |
| Cab29 $V_L$ | DIVMIQNPLSLSVSLGEPASISCRSSQSLLATDGYEYLDWYLQKPG QSPQILIYGASNRASGVP DRFSGRGSGTDFTLKITKVEAEDVGVYYCLQHKALPPTFGQGTKL EIK (SEQ ID NO: 132) |

TABLE 3-continued

| Exemplary sequences. | |
|---|---|
| Description | Sequence |
| Cab30 $V_L$ | DIVMTQTPLSLPVTPGEPASISCRSSQSLLHSDGYTYLDWYLQRPG QSPHLLIYGGSNRASGVP DRFSGSGSGTDFTLKISKVEAEDVGVYYCMQHKVLPPTFGQGTKL EIK (SEQ ID NO: 133) |
| Cab31 $V_L$ | DTVMSQIPLSLPVTPGEPASISCRSSQSLLHSDGYTYMDWYLQKPG QSPQLLIYGGSNRASGVP DRFSGSGSGTDFTLKISKVEAEDVGVYYCMQHKVLPPTFGQGTRL EIK (SEQ ID NO: 134) |
| Cab05 $V_L$<br>Cab34 $V_L$<br>Cab35 $V_L$<br>Cab36 $V_L$<br>Cab37 $V_L$<br>Cab38 $V_L$<br>Cab39 $V_L$<br>Cab40 $V_L$<br>Cab41 $V_L$ | DIVMTQSPLSLPVTPGEPASISCRSSQSLLASDGYNYIDWYLQKPG QSPQLLIYGGSNRASGVP DRFSGSGSGTDFTLKISRVEAEDVGVYFCLQHRALPPTFGQGTKLE IK (SEQ ID NO: 135) |
| Cab32 $V_L$ | DIVMTQSPLSLPVTPGEPASISCRSSQSLL- ASDGYIYIDWYLQKPGQ SPQLLIYGGSNRASGVP DRFSGSGSGTDFTLKISRVEAEDVGVYFCLQHRALPPTFGQGTKLE IK (SEQ ID NO: 136) |
| Cab33 $V_L$ | DIVMTQSPLSLPVTPGEPASISCRSSQSLLASDGYNYIDWYLQKPG QSPQLLIYGGSNRASGVP DRFSGSGSGTDFTLKISRVEAEDVGVYFCLQHKALPPTFGQGTKLE IK (SEQ ID NO: 137) |
| Cab42 $V_L$ | DIVMTQSPLSLPVTPGEPASISCRSSQSLLAS- DAYNYIDWYLQKPGQ SPQLLIYGGSNRASGVP DRFSGSGSGTDFTLKISRVEAEDVGVYFCLQHRALPPTFGQGTKLE IK (SEQ ID NO: 138) |
| Cab43 $V_L$<br>Cab45 $V_L$ | DIVMTQSPLSLPVTPGEPASISCRSSQNLLATDGYTYLDWYLQKPG QSPQLLIYGGS KRASGVPDRFSGSGSGTDFTLKISRVEAEDVGVYYCLQHRALPPTF GQGTKLEIK (SEQ ID NO: 139) |
| Cab44 $V_L$<br>Cab46 $V_L$ | DIVMTQSPLSLPVTPGEPASISCRSSQSLLATDGYEYLDWYLQKPG QSPQLLIYGAS NRASGVPDRFSGSGSGTDFTLKISRVEAEDVGVYYCLQHKALPPTF GQGTKLEIK (SEQ ID NO: 140) |
| Human C5a | TLQKKIEEIAAKYKHSVVKKCCYDGACVNNDETCEQRAARISLGP RCIKAFTECCVVASQLRANISHKDMQLGR (SEQ ID NO: 141) |
| IgG1 heavy chain constant region | ASTKGPSVFPLAPSSKSTSGGTAALGCLVKDYFPEPVTVSWNSGAL TSGVHTFPAVLQSSGLYS- LSSVVTVPSSSLGTQTYICNVNHKPSNTK VDKKVEPKSCDKTHTCPPCPAPELLGGPSVFLFPPKPKDTLMIS- RTP EVTCVVVDVSHEDPEVKFNWYVDGVEVHNAKTKPREEQYNSTY RVVSVLTVLHQDWLNGKEYKCKVSNKALPAPIEKTISKAKGQPRE PQVYTLPPSREEMTKNQVSLTCLVKGFYPSDIAVEWESNGQPENN YKTTPPVLDSDGSFFLYSKLTVDKSRWQQGNVFSCSVMHEALHNH YTQKSLSLSPGK (SEQ ID NO: 142) |
| IgG4 heavy chain constant region | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPSCPAPEFLGGPSVFLFPPKPKDTLMISRT- PEV |

TABLE 3-continued

| Exemplary sequences. | |
|---|---|
| Description | Sequence |
| | TCVVVDVSQEDPEVQFNWYVDGVEVHNAKTKPREEQFNSTYRVV SVLTVLHQDWLNGKEYKCKVSNKGLPSSIEKTISKAKGQPREPQV YTLPPSQEEMTKNQVSLTCLVKGFYPSDIAVEWESNGQPENNYKT TPPVLDSDGSFFLYSRLTVDKSRWQEGNVFSCSVMHEALHNHYTQ KSLSLSLGK (SEQ ID NO: 143) |
| Light chain constant region | RTVAAPSVFIFPPSDEQLKSGTASVVCLLNNFYPREAKVQWKVDN ALQSGNSQESVTEQDSKDSTYSLSSTLTLSKADYEKHKVYACEVT HQGLSSPVTKSFNRGEC (SEQ ID NO: 144) |

C5a

The complement system is composed of over 30 proteins, activated in response to tissue injury, invading pathogens or other foreign surfaces. Complement component 5a (C5a) was first described as a cleavage product of complement factor 5 (C5) with chemotactic and anaphylatoxic properties (Shin et al., 1968). The precursor for C5a, C5, is a 1676 amino acid, 188 kDa protein whose gene is located at 9q33-9q34 (Wetsel et al., 1988). Human C5a is an ~11 kDa, 74 amino acid glycoprotein released from the alpha-chain of C5 by C5 convertase enzymes. The N-linked glycosylation is not essential for function. Further characterization revealed that C5a is an essential part of the innate immune response and evidence now suggests that it may also play a role in adaptive immunity (Kohl, 2006). Although not necessarily the initiating factor, the excessive or uncontrolled production of C5a that occurs in a number of inflammatory diseases, suggests that C5a promotes and perpetuates inflammatory reactions (Guo and Ward, 2005). C5a has four anti-parallel alpha helices connected by peptide loops, stabilized by three critical disulphide linkages (Monk et al., 2007). Mutagenesis and antibody studies have identified several basic residues that are involved in the interaction with receptors (reviewed in Monk et al., 2007).

The complement cascade is activated via four pathways: the classical, the alternative, the mannan-binding lectin (MBL) or the extrinsic protease pathway (Ricklin and Lambris, 2007). The classical and lectin pathways are activated by the formation of antibody complexes on the surface of pathogens and by the interaction with mannose on bacterial surfaces, respectively. Both pathways lead to the cleavage of C4 to C4b and C4a by serine proteases. C4b binds C2 and the same proteases lead to the generation of C2a which is part of the classical pathway C3 convertase (or C4b2a). The alternative pathway can be activated by foreign surfaces or by 'tickover'; the spontaneous hydrolysis of C3 allowing binding of factor B and formation of the alternative pathway C3 convertase (C3bBb), which maintains a continuous low level of complement cascade activation to ensure a rapid response to pathogens (Ricklin and Lambris, 2007). All three pathways result in the formation of C3 convertases which cleave C3 to form C3a and C3b. C3b acts to opsonize pathogen surfaces for recognition and clearance, but also forms part of the C5 convertases (C4b2aC3b or C3bBbC3b) that cleaves C5 to yield C5a and C5b. C5b goes on to initiate the assembly of the poreforming membrane attack complex (MAC; C5b-9). The complement cascade is closely regulated by a series of soluble and membrane bound regulatory proteins which prevent complement activation products from targeting host tissues (Ricklin and Lambris, 2007). However, this control can be bypassed by extrinsic pathways that involve direct cleavage of C3 and C5 by proteases such as thrombin (Amara et al., 2008). Further, activated neutrophils and alveolar macrophages can generate C5a from C5 with secreted serine proteases (Amara et al., 2008). Upon cleavage from C5, C5a is quickly metabolized by plasma and cell surface carboxypeptidases which remove the C-terminal arginine to form C5adesArg (Bokisch and Muller-Eberhard, 1970). C5adesArg has reduced potency compared to C5a, in line with a reduced binding affinity for the classical C5a receptor, CD88 (Higginbottom et al., 2005). C5a and C5adesArg are cleared quickly from the body, with ~50% of both cleared from the circulation within 2-3 min, mediated partly by the binding of C5a to CD88 on leukocytes and other cells (Oppermann and Gotze, 1994). However, the second receptor, C5a receptor-like 2 (C5L2), may be more effective at the removal of complement fragments, particularly C5adesArg by rapidly internalizing C5a/C5adesArg, where it is retained and, in some cell types, degraded (Scola et al., 2009). In contrast, cells expressing CD88 internalize C5a but release a higher proportion in an undegraded, possibly still active form. Plasma C5a may also be cleared by the liver (Chenoweth and Goodman, 1983).

CD88

C5a binds with similar high affinity to both CD88 and C5L2. In contrast, while the affinity of C5adesArg for C5L2 is similar to C5a (~12 nM), the affinity for CD88 is much lower (~660 nM) (Monk et al., 2007). CD88 and C5L2 share a 35% sequence homology and are located in the same region of chromosome 19 (19q13.3-19q13.4). They are clustered together with genes for other chemoattractant receptors, such as the formyl peptide receptor family and bradykinin receptors. Both are glycosylated, seven transmembrane spanning proteins with molecular weights of –45 kDa. CD88 is a G protein-coupled receptor and a member of the rhodopsin gene family (Monk et al., 2007). C5a is thought to interact with CD88 via a two-site binding process, whereby binding occurs at two distinct and physically separate sites. The first 'recognition' site, located in the receptor's extracellular amino terminus (N-terminus), binds the C5a N-terminus and disulphide-linked core. The second 'activation' site is formed by the transmembrane domains of the receptor, which interact with the C-terminus of C5a and results in generation of specific signal transduction pathways that are mediated by receptor coupled G proteins (Monk et al., 2007).

C5L2

C5L2 is expressed on most of the same cell types as CD88, such as neutrophils, monocytes, lymphocytes and macrophages, as well as non-myeloid cells such as vascular smooth muscle cells and cells from tissues such as adrenal gland, heart, liver, lung spleen and brain, albeit at much lower levels than CD88 under noninflammatory conditions (Gao et al., 2005). The function of C5L2 remains unclear. Some experimental data suggest that C5L2 functions as a non-signaling decoy receptor; knockout or blockade of C5L2 was found to exacerbate the inflammatory response in mice (Gao et al., 2005; Gerard et al., 2005). This suggests C5L2 has anti-inflammatory functions, possibly by reducing the C5a available to bind to CD88. However, C5L2 can act as a positive regulator that is critical for C5a and C3a signaling (at least in mice) (Chen et al., 2007). In vitro, it was found that C5L2 is required to facilitate C5a signaling in neutrophils, macrophages and fibroblasts, while lack of C5L2 in vivo resulted in reduced ovalbumin-induced airway hyperresponsiveness and inflammation (Chen et al., 2007). Furthermore, in a mouse model of 'high-grade' sepsis (100% lethality), only blockade of both C5L2 and CD88 provided protection (Rittirsch et al., 2008).

Full-Length Anti-C5a Antibody

The anti-C5a antibody in some embodiments is a full-length anti-C5a antibody. In some embodiments, the full-length anti-C5a antibody is an IgA, IgD, IgE, IgG, or IgM. In some embodiments, the full-length anti-C5a antibody comprises IgG constant domains, such as constant domains of any one of IgG1, IgG2, IgG3, and IgG4 including variants thereof. In some embodiments, the full-length anti-C5a antibody comprises a lambda light chain constant region. In some embodiments, the full-length anti-C5a antibody comprises a kappa light chain constant region. In some embodiments, the full-length anti-C5a antibody is a full-length human anti-C5a antibody. In some embodiments, the full-length anti-C5a antibody comprises an Fc sequence of a mouse immunoglobulin. In some embodiments, the full-length anti-C5a antibody comprises an Fc sequence that has been altered or otherwise changed so that it has enhanced antibody dependent cellular cytotoxicity (ADCC) or complement dependent cytotoxicity (CDC) effector function.

Thus, for example, in some embodiments, there is provided a full-length anti-C5a antibody comprising IgG1 constant domains, wherein the anti-C5a antibody specifically binds to C5a. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG2 constant domains, wherein the anti-C5a antibody specifically binds to C5a. In some embodiments, the IgG2 is human IgG2. In some embodiments, the light chain constant region comprises or consists of the amino acid sequence of SEQ ID NO: 144.

In some embodiments, there is provided a full-length anti-C5a antibody comprising IgG3 constant domains, wherein the anti-C5a antibody specifically binds to C5a. In some embodiments, the IgG3 is human IgG3. In some embodiments, the light chain constant region comprises or consists of the amino acid sequence of SEQ ID NO: 144.

In some embodiments, there is provided a full-length anti-C5a antibody comprising IgG4 constant domains, wherein the anti-C5a antibody specifically binds to C5a. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising an amino acid sequence having at least about 90% sequence identify with any one of SEQ ID NOs: 1-6, an HC-CDR2 comprising an amino acid sequence having at least about 90% sequence identify with any one of SEQ ID NOs: 7-29, and an HC-CDR3 comprising an amino acid sequence having at least about 90% sequence identify with any one of SEQ ID NOs: 30-38; and b) a light chain variable domain comprising an LC-CDR1 comprising the amino acid sequence having at least about 90% sequence identify with any one of SEQ ID NOs: 39-56, an LC-CDR2 comprising the amino acid sequence having at least about 90% sequence identify with any one of SEQ ID NOs: 57-59, and an LC-CDR3 comprising the amino acid sequence having at least about 90% sequence identify with any one of SEQ ID NOs: 60-66.

In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG2 constant domains, wherein the anti-C5a antibody comprises a) a heavy chain variable domain comprising an HC-CDR1 comprising an amino acid sequence having at least about 90% sequence identify with any one of SEQ ID NOs: 1-6, an HC-CDR2 comprising an amino acid sequence having at least about 90% sequence identify with any one of SEQ ID NOs: 7-29, and an HC-CDR3 comprising an amino acid sequence having at least about 90% sequence identify with any one of SEQ ID NOs: 30-38; and b) a light chain variable domain comprising an LC-CDR1 comprising an amino acid sequence having at least about 90% sequence identify with any one of SEQ ID NOs: 39-56, an LC-CDR2 comprising an amino acid sequence having at least about 90% sequence identify with any one of SEQ ID NOs: 57-59, and an LC-CDR3 comprising an amino acid sequence having at least about 90% sequence identify with any one of SEQ ID NOs: 60-66. In some embodiments, the IgG2 is human IgG2. In some embodiments, the light chain constant region comprises or consists of the amino acid sequence of SEQ ID NO: 144.

In some embodiments, there is provided a full-length anti-C5a antibody comprising IgG3 constant domains, wherein the anti-C5a antibody comprises a) a heavy chain variable domain comprising an HC-CDR1 comprising an amino acid sequence having at least about 90% sequence identify with any one of SEQ ID NOs: 1-6, an HC-CDR2 comprising an amino acid sequence having at least about 90% sequence identify with any one of SEQ ID NOs: 7-29, and an HC-CDR3 comprising an amino acid sequence having at least about 90% sequence identify with any one of SEQ ID NOs: 30-38; and b) a light chain variable domain comprising an LC-CDR1 comprising an amino acid sequence having at least about 90% sequence identify with any one of SEQ ID NOs: 39-56, an LC-CDR2 comprising an amino acid sequence having at least about 90% sequence identify with any one of SEQ ID NOs: 57-59, and an LC-CDR3 comprising an amino acid sequence having at least about 90% sequence identify with any one of SEQ ID NOs: 60-66. In some embodiments, the IgG3 is human IgG3. In some embodiments, the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising an amino acid sequence having at least about 90% sequence identify with any one of SEQ ID NOs: 1-6, an HC-CDR2 comprising an amino acid sequence having at least about 90% sequence identify with any one of SEQ ID NOs: 7-29, and an HC-CDR3 comprising an amino acid sequence having at least about 90% sequence identify with any one of SEQ ID NOs: 30-38; and b) a light chain variable domain comprising an LC-CDR1 comprising an amino acid sequence having at least about 90% sequence identify with any one of SEQ ID NOs: 39-56, an LC-CDR2 comprising an amino acid sequence having at least about 90% sequence identify with any one of SEQ ID NOs: 57-59, and an LC-CDR3 comprising an amino acid sequence having at least about 90% sequence identify with any one of SEQ ID NOs: 60-66. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of any one of SEQ ID NOs: 1-6, an HC-CDR2 comprising the amino acid sequence of any one of SEQ ID NOs: 7-29, and an HC-CDR3 comprising the amino acid sequence of any one of SEQ ID NOs: 30-38; and b) a light chain variable domain comprising an LC-CDR1 comprising the amino acid sequence of any one of SEQ ID NOs: 39-56, an LC-CDR2 comprising the amino acid sequence of any one of SEQ ID NOs: 57-59, and an LC-CDR3 comprising the amino acid sequence of any one of SEQ ID NOs: 60-66. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of any one of SEQ ID NOs: 1-6, an HC-CDR2 comprising the amino acid sequence of any one of SEQ ID NOs: 7-29, and an HC-CDR3 comprising the amino acid sequence of any one of SEQ ID NOs: 30-38; and b) a light chain variable domain comprising an LC-CDR1 comprising the amino acid sequence of any one of SEQ ID NOs: 39-56, an LC-CDR2 comprising the amino acid sequence of any one of SEQ ID NOs: 57-59, and an LC-CDR3 comprising the amino acid sequence of any one of SEQ ID NOs: 60-66.

In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 30; and b) a light chain variable domain comprising an LC-CDR1 comprising the amino acid sequence of SEQ ID NO: 39, an LC-CDR2 comprising the amino acid sequence of SEQ ID NO: 57, and an LC-CDR3 comprising the amino acid sequence of SEQ ID NO: 60. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 8, and an HC-CDR3 comprising the amino acid sequence of SEQ ID NO: 31; and b) a light chain variable domain comprising an LC-CDR1 comprising the amino acid sequence of SEQ ID NO: 40, an LC-CDR2 comprising the amino acid sequence of SEQ ID NO: 57, and an LC-CDR3 comprising the amino acid sequence of SEQ ID NO: 61. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 10, and an HC-CDR3 comprising the amino acid sequence of SEQ ID NO: 32; and b) a light chain variable domain comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 11, and an HC-CDR3 comprising the amino acid sequence of SEQ ID NO: 32; and b) a light chain variable domain comprising an LC-CDR1 comprising the amino acid sequence of SEQ ID NO: 41, an LC-CDR2 comprising the amino acid sequence of SEQ ID NO: 57, and an LC-CDR3 comprising the amino acid sequence of SEQ ID NO: 64. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 9, and an HC-CDR3 comprising the amino acid sequence of SEQ ID NO: 32; and b) a light chain variable domain comprising an LC-CDR1 comprising the amino acid sequence of SEQ ID NO: 43, an LC-CDR2 comprising the amino acid sequence of SEQ ID NO: 57, and an LC-CDR3 comprising the amino acid sequence of SEQ ID NO: 63. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 11, and an HC-CDR3 comprising the amino acid sequence of SEQ ID NO: 35; and b) a light chain variable domain comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 60. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 36; and b) a light chain variable domain comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 5, an HC-CDR2 comprising the amino acid sequence of SEQ ID NO: 21, and an HC-CDR3 comprising the amino acid sequence of SEQ ID NO: 32; and b) a light chain variable domain comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 10, and an HC-CDR3 comprising the amino acid sequence of SEQ ID NO: 32; and b) a light chain variable domain comprising an LC-CDR1 comprising the amino acid sequence of SEQ ID NO: 53, an LC-CDR2 comprising the amino acid sequence of SEQ ID NO: 59, and an LC-CDR3 comprising the amino acid sequence of SEQ ID NO: 65. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 23, and an HC-CDR3 comprising the amino acid sequence of SEQ ID NO: 32; and b) a light chain variable domain comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 23, and an HC-CDR3 comprising the amino acid sequence of SEQ ID NO: 32; and b) a light chain variable domain comprising an LC-CDR1 comprising the amino acid sequence of SEQ ID NO: 56, an LC-CDR2 comprising the amino acid sequence of SEQ ID NO: 57, and an LC-CDR3 comprising the amino acid sequence of SEQ ID NO: 61. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 36; and b) a light chain variable domain comprising an LC-CDR1 comprising the amino acid sequence of SEQ ID NO: 52, an LC-CDR2 comprising the amino acid sequence of SEQ ID NO: 58, and an LC-CDR3 comprising the amino acid sequence of SEQ ID NO: 61. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 36; and b) a light chain variable domain comprising an LC-CDR1 comprising the amino acid sequence of SEQ ID NO: 53, an LC-CDR2 comprising the amino acid sequence of SEQ ID NO: 59, and an LC-CDR3 comprising the amino acid sequence of SEQ ID NO: 65. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 5, an HC-CDR2 comprising the amino acid sequence of SEQ ID NO: 21, and an HC-CDR3 comprising the amino acid sequence of SEQ ID NO: 32; and b) a light chain variable domain comprising an LC-CDR1 comprising the amino acid sequence of SEQ ID NO: 52, an LC-CDR2 comprising the amino acid sequence of SEQ ID NO: 58, and an LC-CDR3 comprising the amino acid sequence of SEQ ID NO: 61. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a) a heavy chain variable domain comprising an HC-CDR1 comprising the amino acid sequence of SEQ ID NO: 5, an HC-CDR2 comprising the amino acid sequence of SEQ ID NO: 21, and an HC-CDR3 comprising the amino acid sequence of SEQ ID NO: 32; and b) a light chain variable domain comprising an LC-CDR1 comprising the amino acid sequence of SEQ ID NO: 53, an LC-CDR2 comprising the amino acid sequence of SEQ ID NO: 59, and an LC-CDR3 comprising the amino acid sequence of SEQ ID NO: 65. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO:

142 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 30; and b) a light chain variable domain comprising an LC-CDR1 comprising the amino acid sequence of SEQ ID NO: 39, an LC-CDR2 comprising the amino acid sequence of SEQ ID NO: 57, and an LC-CDR3 comprising the amino acid sequence of SEQ ID NO: 60. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 8, and an HC-CDR3 comprising the amino acid sequence of SEQ ID NO: 31; and b) a light chain variable domain comprising an LC-CDR1 comprising the amino acid sequence of SEQ ID NO: 40, an LC-CDR2 comprising the amino acid sequence of SEQ ID NO: 57, and an LC-CDR3 comprising the amino acid sequence of SEQ ID NO: 61. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 10, and an HC-CDR3 comprising the amino acid sequence of SEQ ID NO: 32; and b) a light chain variable domain comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 11, and an HC-CDR3 comprising the amino acid sequence of SEQ ID NO: 32; and b) a light chain variable domain comprising an LC-CDR1 comprising the amino acid sequence of SEQ ID NO: 41, an LC-CDR2 comprising the amino acid sequence of SEQ ID NO: 57, and an LC-CDR3 comprising the amino acid sequence of SEQ ID NO: 64. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 9, and an HC-CDR3 comprising the amino acid sequence of SEQ ID NO: 32; and b) a light chain variable domain comprising an LC-CDR1 comprising the amino acid sequence of SEQ ID NO: 43, an LC-CDR2 comprising the amino acid sequence of SEQ ID NO: 57, and an LC-CDR3 comprising the amino acid sequence of SEQ ID NO: 63. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 11, and an HC-CDR3 comprising the amino acid sequence of SEQ ID NO: 35; and b) a light chain variable domain comprising an LC-CDR1 comprising the amino acid sequence of SEQ ID NO: 44, an LC-CDR2 comprising the amino acid sequence of SEQ ID NO: 57, and an LC-CDR3 comprising the amino acid sequence of SEQ ID NO: 60. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 36; and b) a light chain variable domain comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 5, an HC-CDR2 comprising the amino acid sequence of SEQ ID NO: 21, and an HC-CDR3 comprising the amino acid sequence of SEQ ID NO: 32; and b) a light chain variable domain comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 10, and an HC-CDR3 comprising the amino acid sequence of SEQ ID NO: 32; and b) a light chain variable domain comprising an LC-CDR1 comprising the amino acid sequence of SEQ ID NO: 53, an LC-CDR2 comprising the amino acid sequence of SEQ ID NO: 59, and an LC-CDR3 comprising the amino acid sequence of SEQ ID NO: 65. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 23, and an HC-CDR3 comprising the amino acid sequence of SEQ ID NO: 32; and b) a light chain variable domain comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 2, an HC-CDR2 comprising the amino acid sequence of SEQ ID NO: 23, and an HC-CDR3 comprising the amino acid sequence of SEQ ID NO: 32; and b) a light chain variable domain comprising an LC-CDR1 comprising the amino acid sequence of SEQ ID NO: 56, an LC-CDR2 comprising the amino acid sequence of SEQ ID NO: 57, and an LC-CDR3 comprising the amino acid sequence of SEQ ID NO: 61. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 36; and b) a light chain variable domain comprising an LC-CDR1 comprising the amino acid sequence of SEQ ID NO: 52, an LC-CDR2 comprising the amino acid sequence of SEQ ID NO: 58, and an LC-CDR3 comprising the amino acid sequence of SEQ ID NO: 61. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 6, an HC-CDR2 comprising the amino acid sequence of SEQ ID NO: 18, and an HC-CDR3 comprising the amino acid sequence of SEQ ID NO: 36; and b) a light chain variable domain comprising an LC-CDR1 comprising the amino acid sequence of SEQ ID NO: 53, an LC-CDR2 comprising the amino acid sequence of SEQ ID NO: 59, and an LC-CDR3 comprising the amino acid sequence of SEQ ID NO: 65. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 5, an HC-CDR2 comprising the amino acid sequence of SEQ ID NO: 21, and an HC-CDR3 comprising the amino acid sequence of SEQ ID NO: 32; and b) a light chain variable domain comprising an LC-CDR1 comprising the amino acid sequence of SEQ ID NO: 52, an LC-CDR2 comprising the amino acid sequence of SEQ ID NO: 58, and an LC-CDR3 comprising the amino acid sequence of SEQ ID NO: 61. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a) a heavy chain variable domain comprising an HC-CDR1 comprising the amino acid sequence of SEQ ID NO: 5, an HC-CDR2 comprising the amino acid sequence of SEQ ID NO: 21, and an HC-CDR3 comprising the amino acid sequence of SEQ ID NO: 32; and b) a light chain variable domain comprising an LC-CDR1 comprising the amino acid sequence of SEQ ID NO: 53, an LC-CDR2 comprising the amino acid sequence of SEQ ID NO: 59, and an LC-CDR3 comprising the amino acid sequence of SEQ ID NO: 65. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of any one of SEQ ID NOs: 73-111, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 112-140, or a variant thereof having at least about 90% (for example at least about any of 91%, 92%, 93%, 94%, 95%, 96%, 97%, 98%, or 99%) sequence identity. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG2 constant domains, wherein the anti-C5a antibody comprises a heavy chain variable domain comprising the amino acid sequence of any one of SEQ ID NOs: 73-111, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 112-140, or a variant thereof having at least about 90% (for example at least about any of 91%, 92%, 93%, 94%, 95%, 96%, 97%, 98%, or 99%) sequence identity. In some embodiments, the IgG2 is human IgG2. In some embodiments, the light chain constant region comprises or consists of the amino acid sequence of SEQ ID NO: 144.

In some embodiments, there is provided a full-length anti-C5a antibody comprising IgG3 constant domains, wherein the anti-C5a antibody comprises a heavy chain variable domain comprising the amino acid sequence of any one of SEQ ID NOs: 73-111, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 112-140, or a variant thereof having at least about 90% (for example at least about any of 91%, 92%, 93%, 94%, 95%, 96%, 97%, 98%, or 99%) sequence identity. In some embodiments, the IgG3 is human IgG3. In some embodiments, the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of any one of SEQ ID NOs: 73-111, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 112-140, or a variant thereof having at least about 90% (for example at least about any of 91%, 92%, 93%, 94%, 95%, 96%, 97%, 98%, or 99%) sequence identity. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO:143 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of any one of SEQ ID NOs: 73-111, and a light chain variable domain comprising the amino acid sequence of any one of SEQ ID NOs: 112-140. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of any one of SEQ ID NOs: 73-111, and a light chain variable domain comprising the amino acid sequence of any one of SEQ ID NOs: 112-140. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO:143 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 73 and a light chain variable domain comprising the amino acid sequence of SEQ ID NO: 112. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 75 and a light chain variable domain comprising the amino acid sequence of SEQ ID NO: 114. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 100 and a light chain variable domain comprising the amino acid sequence of SEQ ID NO: 135. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 79 and a light chain variable domain comprising the amino acid sequence of SEQ ID NO: 118. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 85 and a light chain variable domain comprising the amino acid sequence of SEQ ID NO: 117. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 88 and a light chain variable domain comprising the amino acid sequence of SEQ ID NO: 126. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 93 and a light chain variable domain comprising the amino acid sequence of SEQ ID NO: 116. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 97 and a light chain variable domain comprising the amino acid sequence of SEQ ID NO: 116. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 77 and a light chain variable domain comprising the amino acid sequence of SEQ ID NO: 132. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 102 and a light chain variable domain comprising the amino acid sequence of SEQ ID NO: 135. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 109 and a light chain variable domain comprising the amino acid sequence of SEQ ID NO: 138. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 110 and a light chain variable domain comprising the amino acid sequence of SEQ ID NO: 139. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 110 and a light chain variable domain comprising the amino acid sequence of SEQ ID NO: 140. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 111 and a light chain variable domain comprising the amino acid sequence of SEQ ID NO: 139. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG1 constant domains, wherein the anti-C5a antibody comprises a heavy chain variable domain comprising the amino acid sequence of SEQ ID NO: 111 and a light chain variable domain comprising the amino acid sequence of SEQ ID NO: 140. In some embodiments, the IgG1 is human IgG1. In some embodiments, the heavy chain constant region comprises or consists of the amino acid sequence of SEQ ID NO: 142. In some embodiments, the light chain constant region comprises or consists of the amino acid sequence of SEQ ID NO: 144. In some embodiments, the heavy chain constant region comprises or consists of the amino acid sequence of SEQ ID NO: 142 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 73 and a light chain variable domain comprising the amino acid sequence of SEQ ID NO: 112. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 75 and a light chain variable domain comprising the amino acid sequence of SEQ ID NO: 114. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 100 and a light chain variable domain comprising the amino acid sequence of SEQ ID NO: 135. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 79 and a light chain variable domain comprising the amino acid sequence of SEQ ID NO: 118. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 85 and a light chain variable domain comprising the amino acid sequence of SEQ ID NO: 117. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 88 and a light chain variable domain comprising the amino acid sequence of SEQ ID NO: 126. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 93 and a light chain variable domain comprising the amino acid sequence of SEQ ID NO: 116. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 97 and a light chain variable domain comprising the amino acid sequence of SEQ ID NO: 116. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 77 and a light chain variable domain comprising the amino acid sequence of SEQ ID NO: 132. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 102 and a light chain variable domain comprising the amino acid sequence of SEQ ID NO: 135. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 109 and a light chain variable domain comprising the amino acid sequence of SEQ ID NO: 138. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 110 and a light chain variable domain comprising the amino acid sequence of SEQ ID NO: 139. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 110 and a light chain variable domain comprising the amino acid sequence of SEQ ID NO: 140. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 111 and a light chain variable domain comprising the amino acid sequence of SEQ ID NO: 139. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

In some embodiments, there is provided a full-length anti-C5a antibody comprising IgG4 constant domains, wherein the anti-C5a antibody comprises a heavy chain variable domain comprising the amino acid sequence of SEQ ID NO: 111 and a light chain variable domain comprising the amino acid sequence of SEQ ID NO: 140. In some embodiments, the IgG4 is human IgG4. In some embodiments, the heavy chain constant region comprises or consists of the amino acid sequence of SEQ ID NO: 143. In some embodiments, the light chain constant region comprises or consists of the amino acid sequence of SEQ ID NO: 144. In some embodiments, the heavy chain constant region comprises or consists of the amino acid sequence of SEQ ID NO: 143 and the light chain constant region comprises or consists of the amino acid sequence of SEQ ID NO: 144.

Binding Affinity

Binding affinity can be indicated by Kd, Koff, Kon, or Ka. The term "Koff", as used herein, is intended to refer to the off-rate constant for dissociation of an antibody from the antibody/antigen complex, as determined from a kinetic selection set up. The term "Kon", as used herein, is intended to refer to the on-rate constant for association of an antibody to the antigen to form the antibody/antigen complex. The term dissociation constant "Kd", as used herein, refers to the dissociation constant of a particular antibody-antigen interaction, and describes the concentration of antigen required to occupy one half of all of the antibody-binding domains present in a solution of antibody molecules at equilibrium, and is equal to Koff/Kon. The measurement of Kd presupposes that all binding agents are in solution. In the case where the antibody is tethered to a cell wall, e.g., in a yeast expression system, the corresponding equilibrium rate constant is expressed as EC50, which gives a good approximation of Kd. The affinity constant, Ka, is the inverse of the dissociation constant, Kd.

The dissociation constant (Kd) is used as an indicator showing affinity of antibody moieties to antigens. For example, easy analysis is possible by the Scatchard method using antibodies marked with a variety of marker agents, as well as by using Biacore (made by Amersham Biosciences), analysis of biomolecular interactions by surface plasmon resonance, according to the user's manual and attached kit. The Kd value that can be derived using these methods is expressed in units of M. An antibody that specifically binds to a target may have a Kd of, for example, $\leq 10^{-7}$ M, $\leq 10^{-8}$ M, $\leq 10^{-9}$ M, $\leq 10^{-10}$ M, $\leq 10^{-11}$ M, $\leq 10^{-12}$ M, or $\leq 10^{-13}$ M.

Binding specificity of the antibody can be determined experimentally by methods known in the art. Such methods comprise, but are not limited to, Western blots, ELISA-, RIA-, ECL-, IRMA-, EIA-, BIAcore-tests and peptide scans.

In some embodiments, the anti-C5a antibody specifically binds to a target C5a with a Kd of about $10^{-7}$ M to about $10^{-13}$ M (such as about $10^{-7}$ M to about $10^{-13}$ M, about $10^{-8}$ M to about $10^{-13}$ M, about $10^{-9}$ M to about $10^{-13}$ M, or about $10^{-10}$ M to about $10^{-12}$ M). Thus in some embodiments, the Kd of the binding between the anti-C5a antibody and C5a, is about $10^{-7}$ M to about $10^{-13}$ M, about $1\times10^{-7}$ M to about $5\times10^{-13}$ M, about $10^{-7}$ M to about $10^{-12}$ M, about $10^{-7}$ M to about $10^{-11}$ M, about $10^{-7}$ M to about $10^{-10}$ M, about $10^{-7}$ M to about $10^{-9}$ M, about $10^{-8}$ M to about $10^{-13}$ M, about $1\times10^{-8}$ M to about $5\times10^{-13}$ M, about $10^{-8}$ M to about $10^{-12}$ M, about $10^{-8}$ M to about $10^{-11}$ M, about $10^{-8}$ M to about $10^{-10}$ M, about $10^{-8}$ M to about $10^{-9}$ M, about $5\times10^{-9}$ M to about $1\times10^{-13}$ M, about $5\times10^{-9}$ M to about $1\times10^{-12}$ M, about $5\times10^{-9}$ M to about $1\times10^{-11}$ M, about $5\times10^{-9}$ M to about $1\times10^{-10}$ M, about $10^{-9}$ M to about $10^{-13}$ M, about $10^{-9}$ M to about $10^{-12}$ M, about $10^{-9}$ M to about $10^{-11}$ M, about $10^{-9}$ M to about $10^{-10}$M, about $5\times10^{-10}$ M to about $1\times10^{-13}$ M, about $5\times10^{-10}$ M to about $1\times10^{-12}$M, about $5\times10^{-10}$M to about $1\times10^{-11}$M, about $10^{-10}$M to about $10^{-13}$ M, about $1\times10^{-10}$M to about $5\times10^{-13}$ M, about $1\times10^{-}$ 10 M to about $1\times10^{-12}$M, about $1\times10^{-IO}$M to about $5\times10^{-}$ 12M, about $1\times10^{-1o}$ M to about $1\times10^{-11}$ M, about $10^{-11}$ M to about $10^{-13}$ M, about $1\times10^{-1}$ M to about $5\times10^{-13}$ M, about $10^{-11}$ M to about $10^{-12}$M, or about $10^{-12}$M to about $10^{-13}$ M. In some embodiments, the Kd of the binding between the anti-C5a antibody and a C5a is about $10^{-7}$ M to about $10^{-13}$ M.

In some embodiments, the Kd of the binding between the anti-C5a antibody and a non-target is more than the Kd of the binding between the anti-C5a antibody and the target, and is herein referred to in some embodiments as the binding affinity of the anti-C5a antibody to the target (e.g., C5a) is higher than that to a non-target. In some embodiments, the non-target is an antigen that is not C5a. In some embodiments, the Kd of the binding between the anti-C5a antibody (against C5a) and a non-C5a target can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the Kd of the binding between the anti-C5a antibody and a target C5a.

In some embodiments, the anti-C5a antibody binds to a non-target with a Kd of about $10^{-1}$ M to about $10^{-6}$ M (such as about $10^{-1}$ M to about $10^{-6}$ M, about $10^{-1}$ M to about $10^{-5}$ M, or about $10^{-2}$ M to about 104 M). In some embodiments, the non-target is an antigen that is not C5a. Thus in some embodiments, the Kd of the binding between the anti-C5a antibody and a non-C5a target is about $10^{-1}$ M to about $10^{-6}$ M, about $1\times10^{-1}$ M to about $5\times10^{-6}$ M, about $10^{-1}$ M to about $10^{-5}$ M, about $1\times10^{-1}$ M to about $5\times10^{-5}$ M, about $10^{-1}$ M to about 104 M, about $1\times10^{-1}$ M to about $5\times10^{-4}$ M, about $10^{-1}$ M to about $10^{-3}$ M, about $1\times10^{-1}$ M to about $5\times10^{-3}$ M, about $10^{-1}$ M to about $10^{-2}$ M, about $10^{-2}$ M to about $10^{-6}$ M, about $1\times10^{-2}$ M to about $5\times10^{-6}$ M, about $10^{-2}$ M to about $10^{-5}$ M, about $1\times10^{-2}$ M to about $5\times10^{-5}$ M, about $10^{-2}$ M to about $10^{-4}$ M, about $1\times10^{-2}$ M to about $5\times10^{-4}$ M, about $10^{-2}$ M to about $10^{-3}$ M, about $10^{-3}$ M to about $10^{-6}$ M, about $1\times10^{-3}$ M to about $5\times10^{-6}$ M, about $10^{-3}$ M to about $10^{-5}$ M, about $1\times10^{-3}$ M to about $5\times10^{-5}$ M, about $10^{-3}$ M to about $10^{-4}$ M, about $10^{-4}$ M to about $10^{-6}$ M, about $1\times10^{-4}$M to about $5\times10^{-6}$ M, about $10^{-4}$ M to about $10^{-5}$ M, or about $10^{-5}$ M to about $10^{-6}$ M.

In some embodiments, when referring to that the anti-C5a antibody specifically recognizes a target C5a at a high binding affinity, and binds to a non-target at a low binding affinity, the anti-C5a antibody will bind to the target C5a with a Kd of about $10^{-7}$ M to about $10^{-13}$ M (such as about $10^{-7}$ M to about $10^{-13}$ M, about $10^{-9}$ M to about $10^{-13}$ M, about $10^{-9}$ M to about $10^{-13}$ M, or about $10^{-10}$ M to about $10^{-12}$ M), and will bind to the non-target with a Kd of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M).

In some embodiments, when referring to that the anti-C5a antibody specifically recognizes C5a, the binding affinity of the anti-C5a antibody is compared to that of a control anti-C5a antibody (such as INab308). In some embodiments, the Kd of the binding between the control anti-C5a antibody and C5a can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times of the Kd of the binding between the anti-C5a antibody described herein and C5a.

Nucleic Acids

Nucleic acid molecules encoding the anti-C5a antibodies are also contemplated. In some embodiments, there is provided a nucleic acid (or a set of nucleic acids) encoding a full-length anti-C5a antibody, including any of the full-length anti-C5a antibodies described herein. In some embodiments, the nucleic acid (or a set of nucleic acids) encoding the anti-C5a antibody described herein may further comprises a nucleic acid sequence encoding a peptide tag (such as protein purification tag, e.g., His-tag, HA tag).

Also contemplated here are isolated host cells comprising an anti-C5a antibody, an isolated nucleic acid encoding the polypeptide components of the anti-C5a antibody, or a vector comprising a nucleic acid encoding the polypeptide components of the anti-C5a antibody described herein.

The present application also includes variants to these nucleic acid sequences. For example, the variants include nucleotide sequences that hybridize to the nucleic acid sequences encoding the anti-C5a antibodies of the present application under at least moderately stringent hybridization conditions.

The present application also provides vectors in which a nucleic acid of the present application is inserted.

In brief summary, the expression of an anti-C5a antibody (e.g., full-length anti-C5a antibody) by a natural or synthetic nucleic acid encoding the anti-C5a antibody can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequences.

The nucleic acids of the present application may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the application provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Green and Sambrook (2013, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the application should not be limited to the use of constitutive promoters. Inducible promoters are also contemplated as part of the application. The use of an inducible promoter provides a molecular switch capable of turning on expression of the polynucleotide sequence to which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the expression of the anti-C5a antibody is inducible. In some embodiments, a nucleic acid sequence encoding the anti-C5a antibody is operably linked to an inducible promoter, including any inducible promoter described herein.

Inducible Promoters

The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. (1993) Proc. Natl. Acad. Sci. USA 90:5603-5607), synthetic ligand-regulated elements (see, e.g., Spencer, D. M. et al 1993) Science 262: 1019-1024) and ionizing radiation-regulated elements (e.g., see Manome, Y. et al. (1993) Biochemistry 32: 10607-10613; Datta, R. et al. (1992) Proc. Natl. Acad. Sci. USA 89: 1014-10153). Further exemplary inducible promoter systems for use in in vitro or in vivo mammalian systems are reviewed in Gingrich et al. (1998) Annual Rev. Neurosci 21:377-405. In some embodiments, the inducible promoter system for use to express the anti-C5a antibody is the Tet system. In some embodiments, the inducible promoter system for use to express the anti-C5a antibody is the lac repressor system from *E. coli*.

An exemplary inducible promoter system for use in the present application is the Tet system. Such systems are based on the Tet system described by Gossen et al. (1993). In an exemplary embodiment, a polynucleotide of interest is under the control of a promoter that comprises one or more Tet operator (TetO) sites. In the inactive state, Tet repressor (TetR) will bind to the TetO sites and repress transcription from the promoter. In the active state, e.g., in the presence of an inducing agent such as tetracycline (Tc), anhydrotetracycline, doxycycline (Dox), or an active analog thereof, the inducing agent causes release of TetR from TetO, thereby allowing transcription to take place. Doxycycline is a member of the tetracycline family of antibiotics having the chemical name of 1-dimethylamino-2,4a,5,7,12-pentahydroxy-11-methyl-4,6-dioxo-1,4a,11,11a,12,12a-hexahydrotetracene-3-carboxamide.

In one embodiment, a TetR is codon-optimized for expression in mammalian cells, e.g., murine or human cells. Most amino acids are encoded by more than one codon due to the degeneracy of the genetic code, allowing for substantial variations in the nucleotide sequence of a given nucleic acid without any alteration in the amino acid sequence encoded by the nucleic acid. However, many organisms display differences in codon usage, also known as "codon bias" (i.e., bias for use of a particular codon(s) for a given amino acid). Codon bias often correlates with the presence of a predominant species of tRNA for a particular codon, which in turn increases efficiency of mRNA translation. Accordingly, a coding sequence derived from a particular organism (e.g., a prokaryote) may be tailored for improved expression in a different organism (e.g., a eukaryote) through codon optimization.

Other specific variations of the Tet system include the following "Tet-Off" and "Tet-On" systems. In the Tet-Off system, transcription is inactive in the presence of Tc or Dox. In that system, a tetracycline-controlled transactivator protein (tTA), which is composed of TetR fused to the strong transactivating domain of VP16 from Herpes simplex virus, regulates expression of a target nucleic acid that is under transcriptional control of a tetracycline-responsive promoter element (TRE). The TRE is made up of TetO sequence concatamers fused to a promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

Conversely, in the Tet-On system, transcription is active in the presence of Tc or Dox. The Tet-On system is based on a reverse tetracycline-controlled transactivator, rtTA. Like tTA, rtTA is a fusion protein comprised of the TetR repressor and the VP16 transactivation domain. However, a four amino acid change in the TetR DNA binding moiety alters rtTA's binding characteristics such that it can only recognize the tetO sequences in the TRE of the target transgene in the presence of Dox. Thus, in the Tet-On system, transcription of the TRE-regulated target gene is stimulated by rtTA only in the presence of Dox.

Another inducible promoter system is the lac repressor system from *E. coli* (See Brown et al., Cell 49:603-612 (1987)). The lac repressor system functions by regulating transcription of a polynucleotide of interest operably linked to a promoter comprising the lac operator (lacO). The lac repressor (lacR) binds to LacO, thus preventing transcription of the polynucleotide of interest. Expression of the polynucleotide of interest is induced by a suitable inducing agent, e.g., isopropyl-β-D-thiogalactopyranoside (IPTG).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, there is provided nucleic acid encoding a full-length anti-C5a antibody according to any of the full-length anti-C5a antibodies described herein. In some embodiments, the nucleic acid comprises one or more nucleic acid sequences encoding the heavy and light chains of the full-length anti-C5a antibody. In some embodiments, each of the one or more nucleic acid sequences are contained in separate vectors. In some embodiments, at least some of the nucleic acid sequences are contained in the same vector. In some embodiments, all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Green and Sambrook (2013, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method of inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present application, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the application.

Preparation of Anti-C5a Antibodies

In some embodiments, the anti-C5a antibody is a monoclonal antibody or derived from a monoclonal antibody. In some embodiments, the anti-C5a antibody comprises $V_H$ and $V_L$ domains, or variants thereof, from the monoclonal antibody. In some embodiments, the anti-C5a antibody further comprises $C_H1$ and $C_L$ domains, or variants thereof, from the monoclonal antibody. Monoclonal antibodies can be prepared, e.g., using known methods in the art, including hybridoma methods, phage display methods, or using recombinant DNA methods. Additionally, exemplary phage display methods are described herein and in the Examples below.

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be sub-cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub-clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In some embodiments, according to any of the anti-C5a antibodies described herein, the anti-C5a antibody comprises sequences from a clone selected from an antibody library (such as a phage library or yeast library presenting scFv or Fab fragments). The following general methods can be used to generate antibody display library. Libraries were generated by PCR cassette mutagenesis with degenerate oligonucleotides as described in Kay et al. (1996), Phage display of peptides and proteins: a laboratory manual, San Diego, Academic Press (see, pages pg 277-291). The doping codon NNK was used to randomize one amino acid position to include 20 possible amino acids. To randomize one amino acid position to include only a subset of amino acids with specific properties, doping codons were used as described in Balint et al, (1993) Gene 137(1):109-18). Site directed mutagenesis was performed using recombinant PCR as described in Innis et al, (1990) PCR protocols: A guide to methods and applications (see, pp. 177-183). The clone may be identified by screening combinatorial libraries for antibody fragments with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J. Mol. Biol.* 222: 581-597 (1992); Marks and Bradbury, *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); *Fellouse, Proc. Natl. Acad. Sci. USA* 101(34): 12467-12472 (2004); and Lee et al., *J. Immunol. Methods* 284(1-2): 119-132(2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The anti-C5a antibodies can be prepared using phage display to screen libraries for anti-C5a antibody moieties specific to the target C5a. The library can be a human scFv phage display library having a diversity of at least $1\times10^9$ (such as at least about any of $1\times10^9$, $2.5\times10^9$, $5\times10^9$, $7.5\times10^9$, $1\times10^{10}$, $2.5\times10^{10}$, $5\times10^{10}$, $7.5\times10^{10}$, or $1\times10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23(3):344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a fully-synthetic phage display library. In some embodiments, the library is a non-human phage display library.

Phage clones that bind to the target C5a with high affinity can be selected by iterative binding of phage to the target C5a, which is bound to a solid support (such as, for example, beads for solution panning or mammalian cells for cell panning), followed by removal of non-bound phage and by elution of specifically bound phage. The bound phage clones are then eluted and used to infect an appropriate host cell, such as *E. coli* XL1-Blue, for expression and purification. The panning can be performed for multiple (such as about any of 2, 3, 4, 5, 6 or more) rounds with solution panning, cell panning, or a combination of both, to enrich for phage clones binding specifically to the target C5a. Enriched phage clones can be tested for specific binding to the target C5a by any methods known in the art, including for example ELISA and FACS.

An alternative method for screening antibody libraries is to display the protein on the surface of yeast cells. Wittrup et al. (U.S. Pat. Nos. 6,699,658 and 6,696,251) have developed a method for a yeast cell display library. In this yeast display system, a component involves the yeast agglutinin protein (Aga1), which is anchored to the yeast cell wall. Another component involves a second subunit of the agglutinin protein Aga2, which can display on the surface yeast cells through disulfide bonds to Aga1 protein. The protein Aga1 is expressed from a yeast chromosome after the Aga1 gene integration. A library of single chain variable fragments (scFv) is fused genetically to Aga2 sequence in the yeast display plasmid, which, after transformation, is maintained in yeast episomally with a nutritional marker. Both of the Aga1 and Aga2 proteins were expressed under the control of the galactose-inducible promoter.

Human antibody V gene repertoire (VH and VK fragments) are obtained by PCR method using a pool of degenerate primers (Sblattero, D. & Bradbury, A. Immunotechnology 3, 271-278 1998). The PCR templates are from the commercially available RNAs or cDNAs, including PBMC, spleen, lymph nodes, bone marrow and tonsils. Separate VH and VK PCR libraries were combined, then assembled together in the scFv format by overlap extension PCR (Sheets, M. D. et al. Proc. Natl. Acad. Sci. USA 95, 6157-6162 1998). To construct the yeast scFv display library, the resultant scFv PCR products are cloned into the yeast display plasmid in the yeasts by homologous recombination. (Chao, G, et al, Nat Protoc. 2006; 1(2):755-68. Miller K D, et al. Current Protocols in Cytometry 4.7.1-4.7.30, 2008).

The anti-C5a antibodies can be discovered using mammalian cell display systems in which antibody moieties are displayed on the cell surface and those specific to the target C5a are isolated by the antigen-guided screening method, as described in U.S. Pat. No. 7,732,195B2. A Chinese hamster ovary (CHO) cell library representing a large set of human IgG antibody genes can be established and used to discover the clones expressing high-affinity antibody genes. Another display system has been developed to enable simultaneous high-level cell surface display and secretion of the same protein through alternate splicing, where the displayed protein phenotype remains linked to genotype, allowing soluble secreted antibody to be simultaneously characterized in biophysical and cell-based functional assays. This approach overcomes many limitations of previous mammalian cell display, enabling direct selection and maturation of antibodies in the form of full-length, glycosylated IgGs (Peter M. Bowers, et al, Methods 2014, 65:44-56). Transient expression systems are suitable for a single round of antigen selection before recovery of the antibody genes and therefore most useful for the selection of antibodies from smaller libraries. Stable episomal vectors offer an attractive alternative. Episomal vectors can be transfected at high efficiency and stably maintained at low copy number, permitting multiple rounds of panning and the resolution of more complex antibody libraries.

The IgG library is based on germline sequence V-gene segments joined to rearranged (D)J regions isolated from a panel of human donors. RNA collected from 2000 human blood samples was reverse-transcribed into cDNA, and the $V_H$ and $V_K$ fragments were amplified using $V_H$- and $V_K$-specific primers and purified by gel extraction. IgG libraries were generated by sub-cloning the $V_H$ and $V_K$ fragments into the display vectors containing IgG1 or K constant regions respectively and then electroporating into or transducing 293T cells. To generate the scFv antibody display library, scFvs were generated by linking $V_H$ and $V_K$, and then sub-cloned into the display vector, which were then electroporated into or transduce 293T cells. As we known, the IgG library is based on germline sequence V-gene segments joined to rearranged (D)J regions isolated from a panel of donors, the donor can be a mouse, rat, rabbit, or monkey.

Monoclonal antibodies can also be made by recombinant DNA methods, such as those described in U.S. Pat. No. 4,816,567. DNA encoding the monoclonal antibodies of the application can be readily isolated and sequenced using conventional procedures (e.g., by using oligonucleotide probes that are capable of binding specifically to genes encoding the heavy and light chains of murine antibodies). Hybridoma cells as described above or C5a-specific phage clones of the application or other source of the C5a-specific clones can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the application, or can be substituted for the variable domains of one antigen-combining site of an antibody of the application to create a chimeric bivalent antibody.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region (CH1) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism.

Human and Humanized Antibodies

The anti-C5a antibodies (e.g., full-length anti-C5a antibodies) can be humanized antibodies or human antibodies. Humanized forms of non-human (e.g., murine) antibody moieties are chimeric immunoglobulins, immunoglobulin chains, or fragments thereof (such as Fv, Fab, Fab', $F(ab')_2$, scFv, or other antigen-binding subsequences of antibodies) that typically contain minimal sequence derived from non-human immunoglobulin. Humanized antibody moieties include human immunoglobulins, immunoglobulin chains, or fragments thereof (recipient antibody) in which residues from a CDR of the recipient are replaced by residues from a CDR of a non-human species (donor antibody) such as mouse, rat, monkey, or rabbit having the desired specificity, affinity, and capacity. In some instances, Fv framework residues of the human immunoglobulin are replaced by corresponding non-human residues. Humanized antibody moieties can also comprise residues that are found neither in the recipient antibody nor in the imported CDR or framework sequences. In general, the humanized antibody can comprise substantially at least one, and typically two, variable domains, in which all or substantially all of the CDR regions correspond to those of a non-human immunoglobulin, and all or substantially all of the FR regions are those of a human immunoglobulin consensus sequence.

Generally, a humanized antibody has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., *Nature,* 321: 522-525 (1986); Riechmann et al., *Nature,* 332: 323-327 (1988); Verhoeyen et al., *Science,* 239: 1534-1536 (1988)), by substituting rodent CDRs or CDR sequences for the corresponding sequences of a human antibody. Accordingly, such "humanized" antibody moieties are antibody moieties (U.S. Pat. No. 4,816,567), wherein substantially less than an intact human variable domain has been substituted by the corresponding sequence from a non-human species. In practice, humanized antibody moieties are typically human antibody moieties in which some CDR residues and possibly some FR residues are substituted by residues from analogous sites in rodent antibodies.

As an alternative to humanization, human antibody moieties can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA,* 90:2551 (1993); Jakobovits et al., *Nature,* 362:255-258 (1993); Bruggemann et al., *Year in Immunol.,* 7:33 (1993); U.S. Pat. Nos. 5,545,806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., *Bio/Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); Lonberg and Huszar, *Intern. Rev. Immunol.,* 13: 65-93 (1995).

Human antibodies may also be generated by in vitro activated B cells (see U.S. Pat. Nos. 5,567,610 and 5,229,275) or by using various techniques known in the art, including phage display libraries. Hoogenboom and Winter, *J. Mol. Biol.,* 227:381 (1991); Marks et al., *J. Mol. Biol.,* 222:581 (1991). The techniques of Cole et al. and Boerner et al. are also available for the preparation of human monoclonal antibodies. Cole et al., *Monoclonal Antibodies and Cancer Therapy*, Alan R. Liss, p. 77 (1985) and Boerner et al., *J. Immunol.,* 147(1): 86-95 (1991).

Anti-C5a Antibody Variants

In some embodiments, amino acid sequences of the anti-C5a antibody variants (e.g., full-length anti-C5a antibody) provided herein are contemplated. For example, it may be desirable to improve the binding affinity and/or other biological properties of the antibody. Amino acid sequence of an antibody variant may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, anti-C5a antibody variants having one or more amino acid substitutions are provided. Sites of interest for substitutional mutagenesis include the HVRs and FRs. Amino acid substitutions may be introduced into an antibody of interest and the products screened for a desired activity, e.g., improved bioactivity, retained/improved antigen binding, decreased immunogenicity, or improved ADCC or CDC.

Conservative substitutions are shown in Table 4 below.

TABLE 4

| CONSERVATIVE SUBSTITUTIONS | | |
|---|---|---|
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

a. hydrophobic: Norleucine, Met, Ala, Val, Leu, Ile;

b. neutral hydrophilic: Cys, Ser, Thr, Asn, Gln;

c. acidic: Asp, Glu;

d. basic: His, Lys, Arg;

e. residues that influence chain orientation: Gly, Pro;

f. aromatic: Trp, Tyr, Phe.

Non-conservative substitutions will entail exchanging a member of one of these classes for another class.

An exemplary substitutional variant is an affinity matured antibody, which may be conveniently generated, e.g., using phage display-based affinity maturation techniques. Briefly, one or more CDR residues are mutated and the variant antibody moieties displayed on phage and screened for a particular biological activity (e.g., bioactivity based on ROS release assay or binding affinity). Alterations (e.g., substitutions) may be made in HVRs, e.g., to improve bioactivity based on ROS release assay or antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ and $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)).

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant VH and $V_L$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or glu) to determine whether the interaction of the antibody with antigen is affected. Further substitutions may be introduced at the amino acid locations to demonstrate functional sensitivity to the initial substitutions. Alternatively, or additionally, a crystal structure of an antigen-antibody complex can be determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intra sequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Fc Region Variants

In some embodiments, one or more amino acid modifications may be introduced into the Fc region of an antibody (e.g., a full-length anti-C5a antibody or anti-C5a Fc fusion protein) provided herein, thereby generating an Fc region variant. In some embodiments, the Fc region variant has enhanced ADCC effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al. *J Biol. Chem.* 9(2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., an anti-C5a antibody). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII. Binding of the Fc receptor to the Fc region of an antibody results in NK cell activation, release of cytolytic granules and consequent target cell apoptosis. The contribution of ADCC to tumor cell killing can be measured with a specific test that uses NK-92 cells that have been transfected with a high-affinity FcR. Results are compared to wild-type NK-92 cells that do not express the FcR.

In some embodiments, the application contemplates an anti-C5a antibody variant (such as a full-length anti-C5a antibody variant) comprising an Fc region that possesses some but not all effector functions, which makes it a desirable candidate for applications in which the half-life of the anti-C5a antibody in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CYTOTOX 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, there is provided an anti-C5a antibody (such as a full-length anti-C5a antibody) variant comprising a variant Fc region comprising one or more amino acid substitutions which improve ADCC. In some embodiments, the variant Fc region comprises one or more amino acid substitutions which improve ADCC, wherein the substitutions are at positions 298, 333, and/or 334 of the variant Fc region (EU numbering of residues). In some embodiments, the anti-C5a antibody (e.g., full-length anti-C5a antibody) variant comprises the following amino acid substitution in its variant Fc region: S298A, E333A, and K334A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

In some embodiments, there is provided an anti-C5a antibody (such as a full-length anti-C5a antibody) variant comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-C5a antibodies (such as full-length anti-C5a antibodies) comprising any of the Fc variants described herein, or combinations thereof, are contemplated.

Glycosylation Variants

In some embodiments, an anti-C5a antibody (such as a full-length anti-C5a antibody) provided herein is altered to increase or decrease the extent to which the anti-C5a antibody is glycosylated. Addition or deletion of glycosylation sites to an anti-C5a antibody may be conveniently accomplished by altering the amino acid sequence of the anti-C5a antibody or polypeptide portion thereof such that one or more glycosylation sites are created or removed.

Wherein the anti-C5a antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-C5a antibody of the application may be made in order to create anti-C5a antibody variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., J. Biochem. 2006, 140:777-83. Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain antibody therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, anti-C5a antibody (such as a full-length anti-C5a antibody) variants are provided comprising an Fc region wherein a carbohydrate structure attached to the Fc region has reduced fucose or lacks fucose, which may improve ADCC function. Specifically, anti-C5a antibodies are contemplated herein that have reduced fucose relative to the amount of fucose on the same anti-C5a antibody produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-C5a antibody is one wherein less than about 50%, 40%, 30%, 20%, 10%, or 5% of the N-linked glycans thereon comprise fucose. For example, the amount of fucose in such an anti-C5a antibody may be from 1% to 80%, from 1% to 65%, from 5% to 65% or from 20% to 40%. In some embodiments, the anti-C5a antibody is one wherein none of the N-linked glycans thereon comprise fucose, i.e., wherein the anti-C5a antibody is completely without fucose, or has no fucose or is afucosylated. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as α-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-C5a antibody (such as a full-length anti-C5a antibody) variants are further provided with bisected oligosaccharides, e.g., in which a biantennary oligosaccharide attached to the Fc region of the anti-C5a antibody is bisected by GlcNAc. Such anti-C5a antibody (such as a full-length anti-C5a antibody) variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering,* 93(5): 851-861 (2006). Anti-C5a antibody (such as full-length anti-C5a antibody) variants with at least one galactose residue in the oligosaccharide attached to the Fc region are also provided. Such anti-C5a antibody variants may have improved CDC function. Such antibody variants are described, e.g., in WO 1997/30087 (Patel et al.); WO 1998/58964 (Raju, S.); and WO 1999/22764 (Raju, S.).

In some embodiments, the anti-C5a antibody (such as a full-length anti-C5a antibody) variants comprising an Fc region are capable of binding to an FcγRIII. In some embodiments, the anti-C5a antibody (such as a full-length anti-C5a antibody) variants comprising an Fc region have ADCC activity in the presence of human effector cells (e.g., T cell) or have increased ADCC activity in the presence of human effector cells compared to the otherwise same anti-C5a antibody (such as a full-length anti-C5a antibody) comprising a human wild-type IgG1Fc region.

Cysteine Engineered Variants

In some embodiments, it may be desirable to create cysteine engineered anti-C5a antibodies (such as a full-length anti-C5a antibody) in which one or more amino acid residues are substituted with cysteine residues. In some embodiments, the substituted residues occur at accessible sites of the anti-C5a antibody. By substituting those residues with cysteine, reactive thiol groups are thereby positioned at accessible sites of the anti-C5a antibody and may be used to conjugate the anti-C5a antibody to other moieties, such as drug moieties or linker-drug moieties, to create an anti-C5a immunoconjugate, as described further herein. Cysteine engineered anti-C5a antibodies (e.g., full-length anti-C5a antibodies) may be generated as described, e.g., in U.S. Pat. No. 7,521,541.

Derivatives

In some embodiments, an anti-C5a antibody (such as a full-length anti-C5a antibody) provided herein may be further modified to contain additional non-proteinaceous moieties that are known in the art and readily available. The moieties suitable for derivatization of the anti-C5a antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the anti-C5a antibody may vary, and if more than one polymers are attached, they can be the same or different molecules. In general, the number and/or type of polymers used for derivatization can be determined based on considerations including, but not limited to, the particular properties or functions of anti-C5a antibody to be improved, whether the anti-C5a antibody derivative will be used in a therapy under defined conditions, etc.

Pharmaceutical Compositions

Also provided herein are compositions (such as pharmaceutical compositions, also referred to herein as formulations) comprising any of the anti-C5a antibodies (such as a full-length anti-C5a antibody), nucleic acids encoding the antibodies, vectors comprising the nucleic acids encoding the antibodies, or host cells comprising the nucleic acids or vectors described herein. In some embodiments, there is provided a pharmaceutical composition comprising any one of the anti-C5a antibodies described herein and a pharmaceutically acceptable carrier.

Suitable formulations of the anti-C5a antibodies are obtained by mixing an anti-C5a antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-C5a antibodies of this application into cells.

The formulation herein may also contain one or more active compounds in addition to the anti-C5a antibody (such as a full-length anti-C5a antibody) as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent in addition to the anti-C5a antibody. Such molecules are suitably present in combination in amounts that are effective for the purpose intended. The effective amount of such other agents depends on the amount of anti-C5a antibody present in the formulation, the type of disease or disorder or treatment, and other factors discussed above. These are generally used in the same dosages and with administration routes as described herein or about from 1 to 99% of the heretofore employed dosages.

The anti-C5a antibodies (e.g., full-length anti-C5a antibodies) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Sustained-release preparations may be prepared.

Sustained-release preparations of the anti-C5a antibodies (e.g., full-length anti-C5a antibodies) can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D (−)-3-hydroxybutyric acid. While polymers such as ethylene-vinyl acetate and lactic acid-glycolic acid enable release of molecules for over 100 days, certain hydro gels release proteins for shorter time periods. When encapsulated antibody remain in the body for a long time, they can denature or aggregate as a result of exposure to moisture at 37° C., resulting in a loss of biological activity and possible changes in immunogenicity. Rational strategies can be devised for stabilization of anti-C5a antibodies depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-C5a antibody (such as a full-length anti-C5a antibody) is formulated in a buffer comprising a citrate, NaCl, acetate, succinate, glycine, polysorbate 80 (Tween 80), or any combination of the foregoing.

The formulations to be used for in vivo administration must be sterile. This is readily accomplished by, e.g., filtration through sterile filtration membranes.

Methods of Treatment Using Anti-C5a Antibodies

The anti-C5a antibodies (e.g., full-length anti-C5a antibodies) and/or compositions of the application can be administered to individuals (e.g., mammals such as humans) to treat a disease and/or disorder associated with high expression levels of C5a, and disease and/or disorder with deregulated C5a function, such as autoimmune and/or inflammatory conditions and/or cancer and/or pain and/or transplantation characterized by high C5a expression and/or abnormal C5a function.

The present application thus in some embodiments provides a method of preventing, treating, maintaining, ameliorating, and/or inhibiting a disease or disorder characterized by high C5a expression and/or abnormal C5a function (e.g., inflammatory disorders, autoimmune disorders, cancer, pain, and transplantation) in an individual comprising administering to the individual an effective amount of a composition (such as a pharmaceutical composition) comprising an anti-C5a antibody (e.g., a full-length anti-C5a antibody), such as any one of the anti-C5a antibodies (e.g., full-length anti-C5a antibodies) described herein.

In some embodiments, the disease or condition is selected, for example, from the group consisting of inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer. In some embodiments, the individual is human.

For example, in some embodiments, there is provided a method of treating an individual having an autoimmune and/or inflammatory conditions and/or cancer and/or pain and/or transplantation characterized by high C5a expression and/or abnormal C5a function comprising administering to the individual an effective amount of a pharmaceutical composition comprising an anti-C5a antibody (e.g., full-length anti-C5a antibody) specifically binding to an epitope on human C5a, wherein the isolated anti-C5a antibody specifically binds to at least one amino acid residue selected from residue D at position 31, residue E at position 32 and residue R at position 40 of human C5a as shown in SEQ ID NO: 141. In some embodiments, the anti-C5a antibody described herein specifically binds residues 31-40 of human C5a as shown in SEQ ID NO: 141. In some embodiments, the anti-C5a antibody is a full-length antibody. In some embodiments, the full-length anti-C5a antibody is an IgG1 or IgG4 antibody. In some embodiments, the disease or condition is selected from the group consisting of inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer. In some embodiments, the individual is human.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a pharmaceutical composition comprising an anti-C5a antibody (e.g., full-length anti-C5a antibody) comprising a heavy chain variable domain ($V_H$) comprising an HC-CDR1 comprising $X_1YYX_2Q$ (SEQ ID NO: 67), wherein $X_1$ is D, or N, and $X_2$ is M, or I; an HC-CDR2 comprising $LIRX_1KX_2X_3GX_4TX_5X_6X_7AASX_8KG$ (SEQ ID NO: 68), wherein $X_1$ is K, or N, $X_2$ is A, or V, $X_3$ is V, N, or I, $X_4$ is G, E, F, H, I, Q, or R, $X_5$ is T, V, or A, $X_6$ is Q, E, T, or S, $X_7$ is Y or F, and $X_8$ is V or L; and an HC-CDR3 comprising $RX_1GPPGLX_2$ (SEQ ID NO: 69), wherein $X_1$ is A, L, or V, and $X_2$ is T, S, or A; and a light chain variable domain ($V_L$) comprising a light chain complementarity determining region (LC-CDR) 1 comprising $RSSQX_1LLX_2X_3X_4X_5YX_6YX_7D$ (SEQ ID NO: 70), wherein $X_1$ is S, R, or N, $X_2$ is A, H, or D, $X_3$ is S or T, $X_4$ is D or N, $X_5$ is G, A, or R, $X_6$ is N, I, T, E, or A, and $X_7$ is I, M, L, or V; a LC-CDR2 comprising $GX_1SX_2RAS$ (SEQ ID NO: 71), wherein $X_1$ is G or A, $X_2$ is N or K; and a LC-CDR3 comprising $X_1QHX_2X_3LPX_4T$ (SEQ ID NO: 72), wherein $X_1$ is L or M, $X_2$ is R or K, $X_3$ is A or V, and $X_4$ is P, or L.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with any one of SEQ ID NOs: 1-6, an HC-CDR2 comprising an amino acid sequence having at least about 90% identify with any one of SEQ ID NOs: 7-29, and an HC-CDR3 comprising an amino acid sequence having at least about 90% identify with any one of SEQ ID NOs: 30-38; and a $V_L$ comprising an LC-CDR1 comprising an amino acid sequence having at least about 90% identify with any one of SEQ ID NOs: 39-56, an LC-CDR2 comprising an amino acid sequence having at least about 90% identify with any one of SEQ ID NOs: 57-59, and an LC-CDR3 comprising an amino acid sequence having at least about 90% identify with SEQ ID NOs: 60-66.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising a $V_H$ comprising an amino acid sequence having at least about 90% identify with any one of SEQ ID NOs: 73-111, and a $V_L$ comprising an amino acid sequence having at least about 90% identify with any one of SEQ ID NOs: 112-140.

In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 1, an HC-CDR2 comprising an amino acid sequence having at least about 90% identify with SEQ ID NO: 7, and an HC-CDR3 comprising an amino acid sequence having at least about 90% identify with SEQ ID NO: 30; and a $V_L$ comprising an LC-CDR1 comprising an amino acid sequence having at least about 90% identify with SEQ ID NO: 39, an LC-CDR2 comprising an amino acid sequence having at least about 90% identify with SEQ ID NO: 57, and an LC-CDR3 comprising an amino acid sequence having at least about 90% identify with SEQ ID NO: 60.

In some embodiments, the anti-C5a antibody provided herein comprises a $V_H$ comprising the amino acid sequence of SEQ ID NO: 73 and a $V_L$ comprising the amino acid sequence of SEQ ID NO: 112. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 2, an HC-CDR2 comprising an amino acid sequence having at least about 90% identify with SEQ ID NO: 8, and an HC-CDR3 comprising an amino acid sequence having at least about 90% identify with SEQ ID NO: 31; and a $V_L$ comprising an LC-CDR1 comprising an amino acid sequence having at least about 90% identify with SEQ ID NO: 40, an LC-CDR2 comprising an amino acid sequence having at least about 90% identify with SEQ ID NO: 57, and an LC-CDR3 comprising an amino acid sequence having at least about 90% identify with SEQ ID NO: 61.

In some embodiments, the anti-C5a antibody provided herein comprises a $V_H$ comprising the amino acid sequence of SEQ ID NO: 75 and a $V_L$ comprising the amino acid sequence of SEQ ID NO: 114. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 2, an HC-CDR2 comprising an amino acid sequence having at least about 90% identify with SEQ ID NO: 10, and an HC-CDR3 comprising an amino acid sequence having at least about 90% identify with SEQ ID NO: 32; and a $V_L$ comprising an LC-CDR1 comprising an amino acid sequence having at least about 90% identify with SEQ ID NO: 42, an LC-CDR2 comprising an amino acid sequence having at least about 90% identify with SEQ ID NO: 57, and an LC-CDR3 comprising an amino acid sequence having at least about 90% identify with SEQ ID NO: 61.

In some embodiments, the anti-C5a antibody provided herein comprises a $V_H$ comprising the amino acid sequence of SEQ ID NO: 100 and a $V_L$ comprising the amino acid sequence of SEQ ID NO: 135. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 2, an HC-CDR2 comprising an amino acid sequence having at least about 90% identify with SEQ ID NO: 11, and an HC-CDR3 comprising an amino acid sequence having at least about 90% identify with SEQ ID NO: 32; and a $V_L$ comprising an LC-CDR1 comprising an amino acid sequence having at least about 90% identify with SEQ ID NO: 41, an LC-CDR2 comprising an amino acid sequence having at least about 90% identify with SEQ ID NO: 57, and an LC-CDR3 comprising an amino acid sequence having at least about 90% identify with SEQ ID NO: 64.

In some embodiments, the anti-C5a antibody provided herein comprises a $V_H$ comprising the amino acid sequence of SEQ ID NO: 79 and a $V_L$ comprising the amino acid sequence of SEQ ID NO: 118. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 2, an HC-CDR2 comprising an amino acid sequence having at least about 90% identify with SEQ ID NO: 9, and an HC-CDR3 comprising an amino acid sequence having at least about 90% identify with SEQ ID NO: 32; and a $V_L$ comprising an LC-CDR1 comprising an amino acid sequence having at least about 90% identify with SEQ ID NO: 43, an LC-CDR2 comprising an amino acid sequence having at least about 90% identify with SEQ ID NO: 57, and an LC-CDR3 comprising an amino acid sequence having at least about 90% identify with SEQ ID NO: 63.

In some embodiments, the anti-C5a antibody provided herein comprises a $V_H$ comprising the amino acid sequence of SEQ ID NO: 85 and a $V_L$ comprising the amino acid sequence of SEQ ID NO: 117. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 2, an HC-CDR2 comprising an amino acid sequence having at least about 90% identify with SEQ ID NO: 11, and an HC-CDR3 comprising an amino acid sequence having at least about 90% identify with SEQ ID NO: 35; and a $V_L$ comprising an LC-CDR1 comprising an amino acid sequence having at least about 90% identify with SEQ ID NO: 44, an LC-CDR2 comprising an amino acid sequence having at least about 90% identify with SEQ ID NO: 57, and an LC-CDR3 comprising an amino acid sequence having at least about 90% identify with SEQ ID NO: 60.

In some embodiments, the anti-C5a antibody provided herein comprises a $V_H$ comprising the amino acid sequence of SEQ ID NO: 88 and a $V_L$ comprising the amino acid sequence of SEQ ID NO: 126. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 6, an HC-CDR2 comprising an amino acid sequence having at least about 90% identify with SEQ ID NO: 18, and an HC-CDR3 comprising an amino acid sequence having at least about 90% identify with SEQ ID NO: 36; and a $V_L$ comprising an LC-CDR1 comprising an amino acid sequence having at least about 90% identify with SEQ ID NO: 42, an LC-CDR2 comprising an amino acid sequence having at least about 90% identify with SEQ ID NO: 57, and an LC-CDR3 comprising an amino acid sequence having at least about 90% identify with SEQ ID NO: 61.

In some embodiments, the anti-C5a antibody provided herein comprises a $V_H$ comprising the amino acid sequence of SEQ ID NO: 93 and a $V_L$ comprising the amino acid sequence of SEQ ID NO: 116. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 5, an HC-CDR2 comprising an amino acid sequence having at least about 90% identify with SEQ ID NO: 21, and an HC-CDR3 comprising an amino acid sequence having at least about 90% identify with SEQ ID NO: 32; and a $V_L$ comprising an LC-CDR1 comprising an amino acid sequence having at least about 90% identify with SEQ ID NO: 42, an LC-CDR2 comprising an amino acid sequence having at least about 90% identify with SEQ ID NO: 57, and an LC-CDR3 comprising an amino acid sequence having at least about 90% identify with SEQ ID NO: 61.

In some embodiments, the anti-C5a antibody provided herein comprises a $V_H$ comprising the amino acid sequence of SEQ ID NO: 97 and a $V_L$ comprising the amino acid sequence of SEQ ID NO: 116. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 2, an HC-CDR2 comprising an amino acid sequence having at least about 90% identify with SEQ ID NO:10, and an HC-CDR3 comprising an amino acid sequence having at least about 90% identify with SEQ ID NO: 32; and a $V_L$ comprising an LC-CDR1 comprising an amino acid sequence having at least about 90% identify with SEQ ID NO: 53, an LC-CDR2 comprising an amino acid sequence having at least about 90% identify with SEQ ID NO: 59, and an LC-CDR3 comprising an amino acid sequence having at least about 90% identify with SEQ ID NO: 65.

In some embodiments, the anti-C5a antibody provided herein comprises a $V_H$ comprising the amino acid sequence of SEQ ID NO: 77 and a $V_L$ comprising the amino acid sequence of SEQ ID NO: 132. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 2, an HC-CDR2 comprising an amino acid sequence having at least about 90% identify with SEQ ID NO:23, and an HC-CDR3 comprising an amino acid sequence having at least about 90% identify with SEQ ID NO: 32; and a $V_L$ comprising an LC-CDR1 comprising an amino acid sequence having at least about 90% identify with SEQ ID NO: 42, an LC-CDR2 comprising an amino acid sequence having at least about 90% identify with SEQ ID NO: 57, and an LC-CDR3 comprising an amino acid sequence having at least about 90% identify with SEQ ID NO: 61.

In some embodiments, the anti-C5a antibody provided herein comprises a $V_H$ comprising the amino acid sequence of SEQ ID NO: 102 and a $V_L$ comprising the amino acid sequence of SEQ ID NO: 135. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 2, an HC-CDR2 comprising an amino acid sequence having at least about 90% identify with SEQ ID NO:23, and an HC-CDR3 comprising an amino acid sequence having at least about 90% identify with SEQ ID NO: 32; and a $V_L$ comprising an LC-CDR1 comprising an amino acid sequence having at least about 90% identify with SEQ ID NO: 56, an LC-CDR2 comprising an amino acid sequence having at least about 90% identify with SEQ ID NO: 57, and an LC-CDR3 comprising an amino acid sequence having at least about 90% identify with SEQ ID NO: 61.

In some embodiments, the anti-C5a antibody provided herein comprises a $V_H$ comprising the amino acid sequence of SEQ ID NO: 109 and a $V_L$ comprising the amino acid sequence of SEQ ID NO: 138. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 6, an HC-CDR2 comprising an amino acid sequence having at least about 90% identify with SEQ ID NO:18, and an HC-CDR3 comprising an amino acid sequence having at least about 90% identify with SEQ ID NO: 36; and a $V_L$ comprising an LC-CDR1 comprising an amino acid sequence having at least about 90% identify with SEQ ID NO: 52, an LC-CDR2 comprising an amino acid sequence having at least about 90% identify with SEQ ID NO: 58, and an LC-CDR3 comprising an amino acid sequence having at least about 90% identify with SEQ ID NO: 61.

In some embodiments, the anti-C5a antibody provided herein comprises a $V_H$ comprising the amino acid sequence of SEQ ID NO: 110 and a $V_L$ comprising the amino acid sequence of SEQ ID NO: 139. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 6, an HC-CDR2 comprising an amino acid sequence having at least about 90% identify with SEQ ID NO:18, and an HC-CDR3 comprising an amino acid sequence having at least about 90% identify with SEQ ID NO: 36; and a $V_L$ comprising an LC-CDR1 comprising an amino acid sequence having at least about 90% identify with SEQ ID NO: 53, an LC-CDR2 comprising an amino acid sequence having at least about 90% identify with SEQ ID NO: 59, and an LC-CDR3 comprising an amino acid sequence having at least about 90% identify with SEQ ID NO: 65.

In some embodiments, the anti-C5a antibody provided herein comprises a $V_H$ comprising the amino acid sequence of SEQ ID NO: 110 and a $V_L$ comprising the amino acid sequence of SEQ ID NO: 140. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 5, an HC-CDR2 comprising an amino acid sequence having at least about 90% identify with SEQ ID NO:21, and an HC-CDR3 comprising an amino acid sequence having at least about 90% identify with SEQ ID NO: 32; and a $V_L$ comprising an LC-CDR1 comprising an amino acid sequence having at least about 90% identify with SEQ ID NO: 52, an LC-CDR2 comprising an amino acid sequence having at least about 90% identify with SEQ ID NO: 58, and an LC-CDR3 comprising an amino acid sequence having at least about 90% identify with SEQ ID NO: 61.

In some embodiments, the anti-C5a antibody provided herein comprises a $V_H$ comprising the amino acid sequence of SEQ ID NO: 111 and a $V_L$ comprising the amino acid sequence of SEQ ID NO: 139. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, there is provided a method of treating an individual having an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer) comprising administering to the individual an effective amount of a composition comprising an anti-C5a antibody comprising: a $V_H$ comprising an HC-CDR1 comprising an amino acid sequence having at least about 90% identify with SEQ ID NO: 5, an HC-CDR2 comprising an amino acid sequence having at least about 90% identify with SEQ ID NO: 21, and an HC-CDR3 comprising an amino acid sequence having at least about 90% identify with SEQ ID NO: 32; and a $V_L$ comprising an LC-CDR1 comprising an amino acid sequence having at least about 90% identify with SEQ ID NO: 53, an LC-CDR2 comprising an amino acid sequence having at least about 90% identify with SEQ ID NO: 59, and an LC-CDR3 comprising an amino acid sequence having at least about 90% identify with SEQ ID NO: 65.

In some embodiments, the anti-C5a antibody provided herein comprises a $V_H$ comprising the amino acid sequence of SEQ ID NO: 111 and a $V_L$ comprising the amino acid sequence of SEQ ID NO: 140. In some embodiments, the anti-C5a antibody provided herein is a full-length anti-C5a antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 142. In some embodiments, the heavy chain constant region comprises or consists of the amino acid sequence of SEQ ID NO: 143. In some embodiments, the light chain constant region comprises or consists of the amino acid sequence of SEQ ID NO: 144.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual is diagnosed with or genetically prone to one or more of the diseases or disorders described herein (such as rheumatoid arthritis, asthma, chronic obstructive pulmonary disease, allergic response, multiple sclerosis, myeloid leukemia, or atherosclerosis). In some embodiments, the individual has one or more risk factors associated with one or more diseases or disorders described herein.

The present application in some embodiments provides a method of delivering an anti-C5a antibody (such as any one of the anti-C5a antibodies described herein, e.g., an isolated anti-C5a antibody) to a cell expressing C5a on its surface in an individual, the method comprising administering to the individual a composition comprising the anti-C5a antibody.

The complement system plays a central role in the clearance of immune complexes and in immune responses to infectious agents, foreign antigens, virus infected cells and tumor cells. Inappropriate or excessive activation of complement cascade can lead to uncontrolled C5a which then causes severe inflammation and tissue injury. Increased in C5a levels in body fluids and tissue samples can be used as a diagnosis biomarker for C5a-mediated diseases and severity thereof. Many diagnostic methods for inflammation or any other diseases exhibiting abnormal C5a expression and the clinical delineation of those diseases are known in the art. Such methods include, but are not limited to, e.g., immunohistochemistry, PCR, and fluorescent in situ hybridization (FISH).

In some embodiments, the anti-C5a antibodies (e.g., full-length anti-C5a antibodies) and/or compositions of the application are administered in combination with a second, third, or fourth agent (including, e.g., an antineoplastic agent, a growth inhibitory agent, a cytotoxic agent, or a chemotherapeutic agent) to treat diseases or disorders involving abnormal C5a expression.

Cancer treatments can be evaluated by, e.g., tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation 100−(T/C×100), where T is the mean relative tumor volume of the treated tumor, and C is the mean relative tumor volume of a non-treated tumor. In some embodiments, the % TGI is about 10%, about 20%, about 30%, about 40%, about 50%, about 60%, about 70%, about 80%, about 90%, about 91%, about 92%, about 93%, about 94%, about 95%, or more than 95%. In some embodiments, the efficacy of treatment is measured using shape change of granulocytes and/or increase in the survival of granulocytes. In some embodiments, the efficacy of treatment is measured by the increase of cytokine secretion by monocytes.

Dosing and Method of Administering the Anti-C5a Antibodies

The dose of the anti-C5a antibody (such as isolated anti-C5a antibody) compositions administered to an individual (such as a human) may vary with the particular composition, the mode of administration, and the type of disease being treated. In some embodiments, the amount of the composition (such as composition comprising isolated anti-C5a antibody) is effective to result in an objective response (such as a partial response or a complete response) in the treatment of cancer. In some embodiments, the amount of the anti-C5a antibody composition is sufficient to result in a complete response in the individual. In some embodiments, the amount of the anti-C5a antibody composition is sufficient to result in a partial response in the individual. In some embodiments, the amount of the anti-C5a antibody composition administered (for example when administered alone) is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the anti-C5a antibody composition. Responses of an individual to the treatment of the methods described herein can be determined, for example, based on RECIST levels.

In some embodiments, the amount of the composition (such as composition comprising isolated anti-C5a antibody) is sufficient to prolong progress-free survival of the individual. In some embodiments, the amount of the composition is sufficient to prolong overall survival of the individual. In some embodiments, the amount of the composition (for example when administered along) is sufficient to produce clinical benefit of more than about any of 50%, 60%, 70%, or 77% among a population of individuals treated with the anti-C5a antibody composition.

In some embodiments, the amount of the composition (such as composition comprising isolated anti-C5a antibody), alone or in combination with a second, third, and/or fourth agent, is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the anti-C5a antibody (such as a full-length anti-C5a antibody) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regimen. In some embodiments, the amount of the composition is more than about any of 80%, 90%, 95%, or 98% of the MTD.

In some embodiments, the amount of an anti-C5a antibody (such as a full-length anti-C5a antibody) in the composition is included in a range of about 0.001 pg to about 1000 μg.

In some embodiments of any of the above aspects, the effective amount of anti-C5a antibody (such as a full-length anti-C5a antibody) in the composition is in the range of about 0.1 μg/kg to about 100 mg/kg of total body weight.

The anti-C5a antibody compositions can be administered to an individual (such as human) via various routes, including, for example, intravenous, intra-arterial, intraperitoneal, intrapulmonary, oral, inhalation, intravascular, intramuscular, intra-tracheal, subcutaneous, intraocular, intrathecal, transmucosal, or transdermal. In some embodiments, sustained continuous release formulation of the composition may be used. In some embodiments, the composition is administered intravenously. In some embodiments, the composition is administered intraportally. In some embodiments, the composition is administered intraarterially. In some embodiments, the composition is administered intraperitoneally. In some embodiments, the composition is administered intrahepatically. In some embodiments, the composition is administered by hepatic arterial infusion. In some embodiments, the administration is to an injection site distal to a first disease site.

Articles of Manufacture and Kits

In some embodiments of the application, there is provided an article of manufacture containing materials useful for the treatment of autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer), or for delivering an anti-C5a antibody (such as a full-length anti-C5a antibody) to a cell expressing C5a on its surface. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is an anti-C5a antibody of the application. The label or package insert indicates that the composition is used for treating the particular condition. The label or package insert will further comprise instructions for administering the anti-C5a antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating autoimmune and/or inflammatory conditions and/or cancer and/or pain and/or transplantation disorders (such as inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, or solid organ cancer). In some embodiments, the package insert indicates that the composition is used for treating inflammatory conditions (e.g. inflammatory response syndrome).

Additionally, the article of manufacture may further comprise a second container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

Kits are also provided that are useful for various purposes, e.g., for treatment of an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer), or for delivering an anti-C5a antibody (such as a full-length anti-C5a antibody) to a cell expressing C5a on its surface, optionally in combination with the articles of manufacture. Kits of the application include one or more containers comprising anti-C5a antibody composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the application are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-C5a antibody (such as a full-length anti-C5a antibody). In some embodiments, the kit comprises a) a composition comprising any one of the anti-C5a antibodies described herein, and b) an effective amount of at least one other agent, wherein the other agent enhances the effects (e.g., treatment effect, detecting effect) of the anti-C5a antibody. In some embodiments, the kit comprises a) a composition comprising any one of the anti-C5a antibodies described herein, and b) instructions for administering the anti-C5a antibody composition to an individual for treatment of an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer). In some embodiments, the kit comprises a) a composition comprising any one of the anti-C5a antibodies described herein, b) an effective amount of at least one other agent, wherein the other agent enhances the effect (e.g., treatment effect, detecting effect) of the anti-C5a antibody, and c) instructions for administering the anti-C5a antibody composition and the other agent(s) to an individual for treatment of an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer). The anti-C5a antibody and the other agent(s) can be present in separate containers or in a single container. For example, the kit may comprise one distinct composition or two or more compositions wherein one composition comprises an anti-C5a antibody and another composition comprises another agent.

In some embodiments, the kit comprises a nucleic acid (or a set of nucleic acids) encoding an anti-C5a antibody (such as a full-length anti-C5a antibody). In some embodiments, the kit comprises a) a nucleic acid (or a set of nucleic acids) encoding an anti-C5a antibody, and b) a host cell for expressing the nucleic acid (or a set of nucleic acids). In some embodiments, the kit comprises a) a nucleic acid (or a set of nucleic acids) encoding an anti-C5a antibody, and b) instructions for i) expressing the anti-C5a antibody in a host cell, ii) preparing a composition comprising the anti-C5a antibody, and iii) administering the composition comprising the anti-C5a antibody to an individual for the treatment of an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer). In some embodiments, the kit comprises a) a nucleic acid (or set of nucleic acids) encoding an anti-C5a antibody, b) a host cell for expressing the nucleic acid (or set of nucleic acids), and c) instructions for i) expressing the anti-C5a antibody in the host cell, ii) preparing a composition comprising the anti-C5a antibody, and iii) administering the composition comprising the anti-C5a antibody to an individual for the treatment of an autoimmune and/or inflammatory conditions and/or cancer and/or pain and/or transplantation characterized by high C5a expression and/or abnormal C5a function (e.g., inflammatory response syndrome (SIRS), sepsis, severe sepsis, septic shock, ischemia/reperfusion related injuries, acute lung injury, pneumonia, acute and chronic graft rejection in transplant patients, graft versus host reactions, renal glomerular diseases, glomerulonephritis, entities of renal failure, rheumatoid arthritis, auto-immune diseases, Bechterew's disease, lupus-type diseases, inflammatory bowel disease, Crohn's disease, tumor growth, and solid organ cancer).

The kits of the application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-C5a antibody compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of an anti-C5a antibody (such as a full-length anti-C5a antibody) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-C5a antibody and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this application. The application will now be described in greater detail by reference to the following non-limiting examples. The following examples further illustrate the application but, of course, should not be construed as in any way limiting its scope.

EXAMPLES

In the experimental disclosure which follows, the following abbreviations apply: C5a (complement component 5a); Avih-C5a(Avi-10His-C5a); Bavih-C5a (Biotin-Avi-10His-C5a); recombinant C5a (rC5a); endogenous C5a (eC5a)

Example 1: Generation of Recombinant Human C5a and Selection of Anti-C5a scFv Antibodies Generation of Recombinant C5a Antigen The full-length sequence of human C5a (synthesized by Generay, Shanghai) was subcloned into the prokaryotic expression vector pTWIN1 and Eukaryotic expression vector pTT5. His-tag or other conventionally used tags were used to tag C5a. Expression vectors pTWIN1-C5a and pTT5-Avi-10His-C5a were generated, "His" stands for His-tag, and "Avi" stands for Avi tag.

Additionally, recombinant cynomolgus monkey C5a was synthesized, as described above, the expression vector pTWIN1-cynoC5a and pTT5-6His-cynoC5a were generated, "His" stands for His-tag.

The expression and purification of recombinant human Avi-10His-C5a was carried out according to manufacturer's protocol. Briefly, 293F cells were transfected with the expression vectors, and the cells were cultured at 37° C., under 5% $CO_2$ and 120 rpm for 5 days. The culture media was collected and proteins with His-tag were purified using Ni Sepharose purification according to manufacturer's protocol. Specifically, the Qiagen Ni-NTA superflow cartridges were used for immobilized metal affinity chromatography (IMAC) analysis. The cartridges were first equilibrated with buffer A1 (50 mM $Na_3PO_4$, 0.15M NaCl, pH 7.2) with a flow rate of 150 cm/h. The supernatant of the culture media, whose pH was adjusted to 7.2, flowed through the cartridges at room temperature with a flow rate of 150 cm/h. Next, buffer A1 (6 times the volume of that of the cartridges) was used to equilibrate the cartridges at 150 cm/h. A 50 mM PB solution (0.15M NaCl and 0.2M Imidazole, pH 7.2) with a volume that is 10 times that of the cartridges was used to wash the cartridges and the elution was collected.

Generation of Biotinylated C5a Antigen

Biotinylation of Avi-10His-C5a using the biotin ligase B0101A (GeneCopoeia) was carried out according to the manufacturer's protocol. Briefly, buffer A/B and BirA ligase were added to Avi-10His-C5a, followed by 2 hours of incubation at 30° C. The biotinylated Avi-10His-C5a is referred to as Bavih-C5a. The efficiency of biotinylation was measured using ELISA. Briefly, Bavih-C5a was serially diluted at a 1:2 ratio, from a starting concentration of 500 ng/mL, before being used to coat the ELISA plate. SA-HRP was used for detection and standard biotinylation products were used as control. The biotinylation efficiency was determined to be 70%.

Selection of Anti-C5a scFv Antibodies scFvs which recognized human C5a were isolated from a yeast display library of the company after several rounds of panning. Briefly, magnetic-activated cell sorting (MACS) was used to enrich cells expressing anti-C5a scFv antibodies. 1000 OD yeast cells were subjected to centrifugation for 5 minutes at 2500 g. Cell pellet was obtained and resuspended in 1 L of SGCAA culture media with OD600=1 as the starting concentration. Expression was induced for 40-48 hours at 20° C. and 250 rpm. After centrifugation and washing with PBSM, the pellet was resuspended in 5-10 times volume of 1 μM Bavih-C5a (in PBSM), and incubated for an hour at 4° C. After centrifugation and washing with PBSM, unbound antigens were washed off with PBSM. Magnetic beads were added and mixed thoroughly before incubation for 30 minutes at 4° C. on a rotator. The supernatant was discarded after centrifugation at 2500 g for 5 minutes, and the pellet was resuspended in PBSM with 5-10 times the volume. 7 mL of cells was added to the column at a time until all cells were passed through the column. Bound cells were collected and upon further culturing and centrifugation were subjected to plasmid isolation.

Generation of phage display library and selection of scFv antibodies: scFv antibody fragments from the selected yeast cells were PCR amplified using scFv-F and scFv-R primers. To generate phage display libraries, the scFv fragments were then cloned into the phage display vector pDAN5 using SfiI. Upon ligation, the vector was used to transduce TG1 phage display electroporation-competent cells to obtain the phage scFv antibody display library. scFv antibodies specific to human C5a were isolated from the phage display library in a series of repeated selection cycles. Briefly, phage scFv library (2×10$^{11}$ PFU) was added to biotinylated C5a, and incubated for 2 hours at 37° C. C5a with phage bound was captured on streptavidin coated magnetic beads. Unbound phages were washed away. After washing with TBST 8-15 times (increasing number of washes for every round of selection), phages that specifically bound to C5a were washed off with Glycine-HCl (pH2.2). These phages were used to transduce TG1 cells in log phase, with the addition of Ampicillin, and cultured for an hour. Upon the addition of helper phage, the cells were cultured on a rocking bed overnight at 200 rpm at 28° C. Culture media was collected the next day, centrifuged to obtain the supernatant, and was subjected to the next round of selection. A panel of positive scFv antibodies were obtained at the end of the selection process.

Figure 1B:
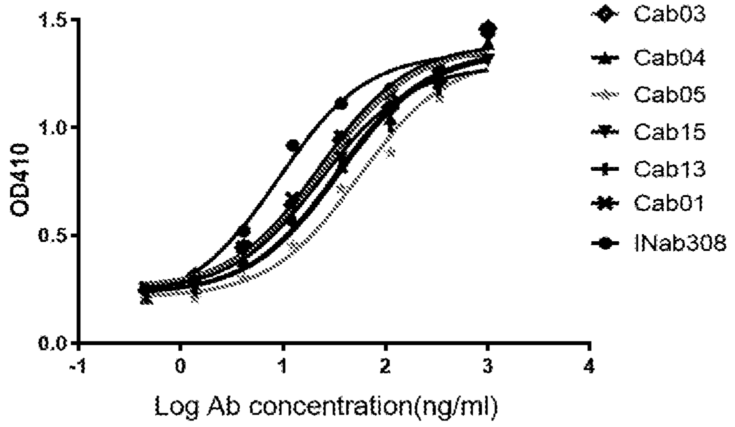

C5a ELISA Binding Assay:

Monoclonal scFv antibodies were selected and subjected to ligand binding assays. The binding assay was designed to identify scFv antibodies that bound human recombinant C5a or endogenous C5a. Briefly, a 96-well plate was coated with human rC5a or eC5a in PBS at 0.1 μg/well and left overnight at 4° C. Before loading the scFv antibodies, the plates were washed with TBST, blocked for 1-2 hours at 37° C. using 5% milk and washed again with TBST. Each scFv sample was first diluted to 10 μg/mL, and 150 μL was added to the first row of wells. The 10 μg/mL scFv samples were then serially diluted at a 1:3 ratio and added to the remaining wells. After incubating for 1 hour at 37° C., followed by washing with TBST 6 times, 100 μl of the primary antibody and secondary antibody mixture (mouse anti-flag (1:2500) and anti-mouse FC-AP (1:2000)) was added to each well. After incubation for 1 hour under 37° C., the plate was washed 3 times using TBST. pNPP was then added at 50 μL/well and incubated for 10-20 minutes at 37° C. 50 μL 3M NaOH was used to stop the reaction. The ELISA results (OD410) were then analyzed and the binding curves were generated by PRISM. The antibody INab308 (an anti-C5a antibody, InflaRx) was used as control, all the selected scFv antibodies exhibited great binding affinity to human recombinant C5a or endogenous C5a. The binding affinity of the partial scFv antibodies Cab01, Cab03, Cab04, Cab05, Cab13, and Cab15 to human rC5a or eC5a was shown in FIGS. 1A-1B.

Reactive oxygen species (ROS) release assay: C5a can stimulate neutrophils to release reactive oxygen species (ROS), promoting neutrophils to participate in a wide range of inflammatory reactions. Based on this biological activity mechanism, induced neutrophils were used to detect the blocking effect of anti-C5a antibodies. The cell line HL-60 is a human promyelocytic leukemia cell line, in brief, 1 mM di-butyryl cAMP sodium salt (sigma, D0260) was used to induce HL60 differentiation for 48 hours, the cell decreased, became spindle-shaped, and differentiated toward neutrophils. C5a can stimulate differentiated HL-60 cells to produce ROS in a dose-dependent manner. A mixed solution of a series of concentrations of C5a antibodies and C5a (5 nM) was used to treat the differentiated cell. DCFH-DA fluorescence probe (sigma, D6883) was added after 30 minutes. After incubation, detected fluorescence intensity at an excitation wavelength of 480 nm and emission wavelength of 525 nm. The data was normalized to calculate the inhibitory activity of the antibody, only C5a stimulation and free of C5a stimulation as 0% and 100% inhibition respectively. All the selected antibodies can effectively reduce neutrophils to release ROS. The ROS production inhibitory activity of the antibodies was shown in Table 5.

TABLE 5

| Antibody | ROS IC50 (nM) |
|---|---|
| Cab01 | 1.51 |
| Cab02 | 1.67 |
| Cab03 | 1.41 |
| Cab04 | 1.87 |
| Cab05 | 1.56 |
| Cab06 | 1.03 |
| Cab07 | 1.07 |
| Cab08 | 1.29 |
| Cab09 | 1.54 |
| Cab10 | 2.02 |
| Cab11 | 1.57 |
| Cab12 | 1.22 |
| Cab13 | 1.08 |
| Cab14 | 1.20 |
| Cab15 | 0.64 |
| Cab16 | 0.87 |
| Cab17 | 1.87 |
| Cab18 | 1.36 |
| Cab19 | 1.32 |
| Cab20 | 0.81 |
| Cab21 | 0.84 |
| Cab22 | 0.91 |
| Cab24 | 1.44 |
| Cab23 | 0.92 |
| Cab25 | 0.54 |
| Cab26 | 1.13 |
| Cab27 | 1.21 |
| Cab28 | 0.98 |
| Cab29 | 0.96 |
| Cab30 | 1.18 |
| Cab31 | 1.26 |

Example 2: Generation and Characterization of Full-Length Anti-C5a Antibodies Generation of Full-Length Anti-C5a Antibodies The most potent scFv antibodies were reformatted as human IgG1 or IgG4 antibody molecules with a human IgG1 or IgG4 heavy chain constant domain, and a human kappa or lambda light chain constant domain. $V_L$ and $V_H$ were amplified from the prokaryotic expression vector and introduced into eukaryotic expression vectors pTT5-K (containing kappa constant domain) or pTT5-L (containing lambda constant domain) and pTT5-H1 (containing IgG1 heavy chain constant domain), or pTT5-H4 (containing IgG4 heavy chain constant domain). Plasmids expressing the light or heavy chains were extracted and used to co-transfect 293F cells. After the cells were cultured at 37° C., 8% $CO_2$ and 120 rpm for 5 days, the culture media was purified using Protein A affinity chromatography. Briefly, Protein A column was first equilibrated with a PBS buffer containing 50 mM PBS and 0.15M NaCl (pH7.2), at a flow rate of 150 cm/h and with a volume that is six times the volume of the column. The supernatant of the culture media (pH was adjusted to 7.2) was passed through the column at the flow rate of 150 cm/h. Upon further equilibration, the column was washed using 50 mM sodium citrate (pH3.5) and the elution was collected.

Improved the affinity and the biological activity of the antibodies: To improve the affinity and the activity of the C5a antibodies, out of the full-length antibodies that were generated, Cab05 was selected as the original antibody. Using the scFv of Cab05, a phage scFv display library containing mutations in the CDR regions was generated.

Variants that were able to block human C5a with high potencies were assessed for biological activity in the ROS release assay. scFv antibodies that showed great biological activity were used to generate full-length antibodies. A further round of selection of the full-length antibodies using the ROS release assay was carried out. The selected optimized antibodies were then subjected to further biochemical and biological analysis.

Reactive Oxygen Species (ROS) Release Assay

ROS release assay was performed as described in Example 1. The optimized antibodies (reformatted as human IgG1) were tested for their abilities to inhibit ROS release. As shown in Table 6, the optimized antibodies showed a high ability to inhibit ROS release.

TABLE 6

| Antibody | ROS IC50 (nM) |
|---|---|
| Cab05 | 1.56 |
| Cab32 | 1.76 |
| Cab33 | 1.70 |
| Cab34 | 1.61 |
| Cab35 | 1.28 |
| Cab36 | 1.41 |
| Cab37 | 0.92 |
| Cab38 | 0.53 |
| Cab39 | 0.91 |
| Cab40 | 0.70 |
| Cab41 | 0.70 |
| Cab42 | 0.78 |
| Cab43 | 0.62 |
| Cab44 | 0.51 |
| Cab45 | 0.64 |
| Cab46 | 0.66 |

Affinity of Anti-C5a Antibodies

Figure 2A:
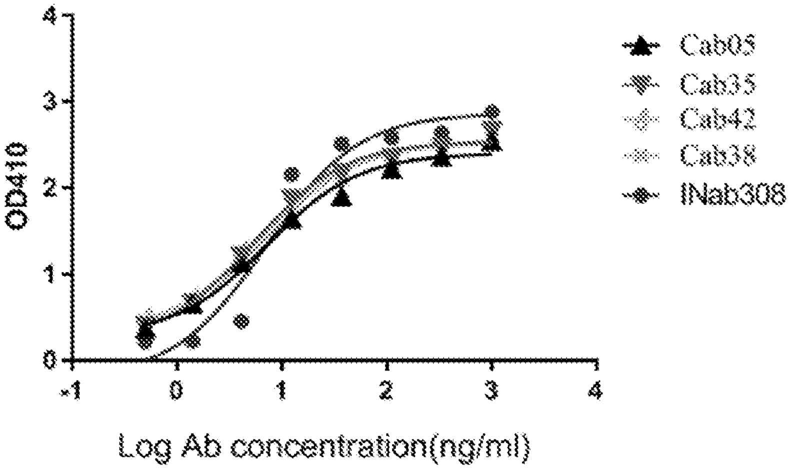
FIG. 2A shows the binding affinity of full-length optimized anti-C5a antibody Cab05-IgG4, Cab35, Cab38, or Cab42, (reformatted as human IgG1) to human recombinant C5a as analyzed by ELISA.
Figure 2B:
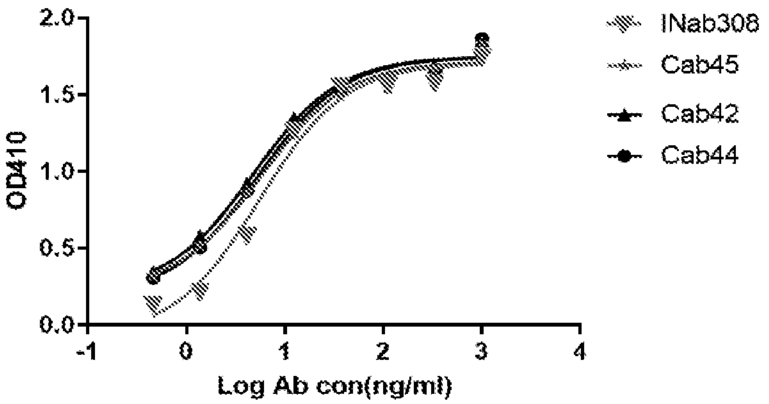
FIG. 2B shows the binding affinity of full-length optimized anti-C5a antibody Cab42, Cab44, or Cab45 (reformatted as human IgG1) to human recombinant C5a as analyzed by ELISA.

C5a ELISA Binding Assay: The affinity of the full-length C5a antibodies for human C5a was evaluated using ELISA, INab308 was used as control. As shown in FIG. 2A, the optimized antibody Cab35, Cab38, or Cab42 (reformatted as human IgG1) exhibited greater or equal affinity for human C5a as compared to the control antibody INab308, and the optimized antibodies also exhibited better or comparable affinity as compared to Cab05. As shown in FIG. 2B, all the optimized antibody Cab42, Cab44, or Cab45 (reformatted as human IgG1) exhibited greater or equal affinity for human C5a as compared to the control antibody INab308.

Figure 2C:
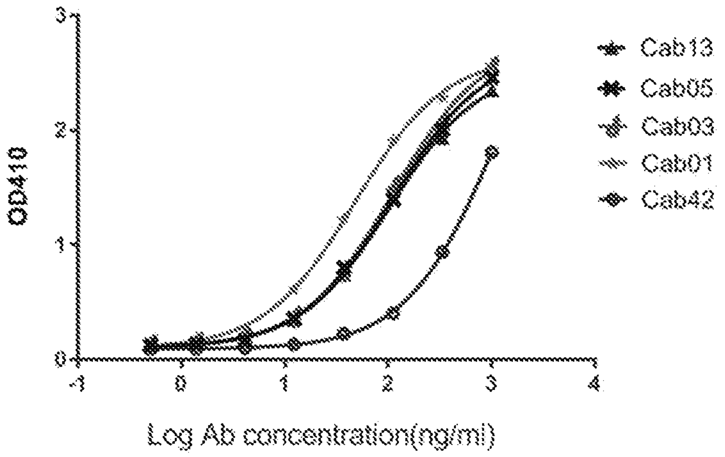
FIG. 2C shows the binding affinity of full-length anti-C5a antibody Cab01, Cab03, Cab05, Cab13 (reformatted as human IgG4) or the optimized C5a antibody Cab42-IgG1 to cynomolgus monkey C5a as analyzed by ELISA.

Next, the affinity of the full-length antibodies Cab01, Cab03, Cab05, and Cab13 (reformatted as human IgG4) and the optimized C5a antibody Cab42-IgG1 for cynomolgus monkey C5a was also detected. These antibodies all exhibited cross-reacted with cynomolgus monkey C5a, as shown in FIG. 2C.

Figure 3A:
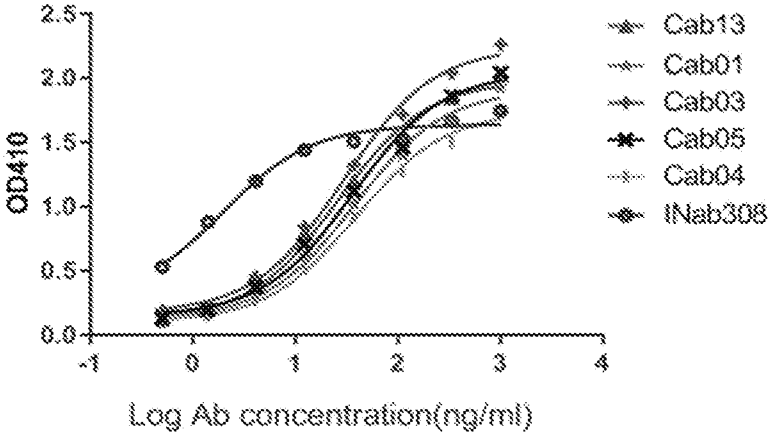
FIGS. 3A-3C shows the binding affinity of full-length exemplary anti-C5a antibodies to human native C5 as analyzed by ELISA.
Figure 3B:
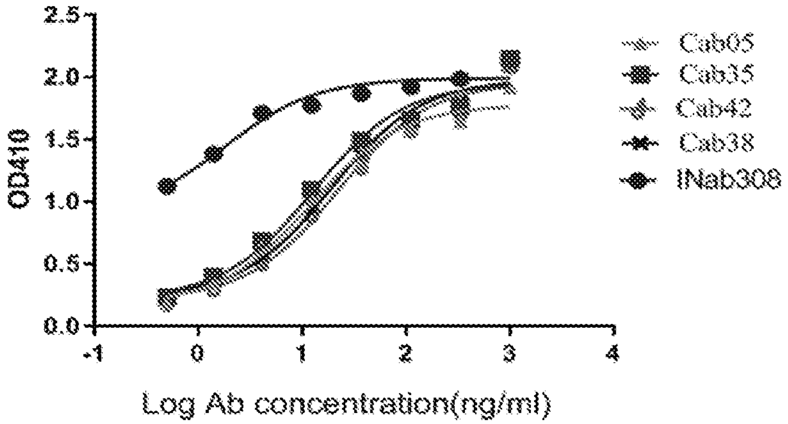
Figure 3C:
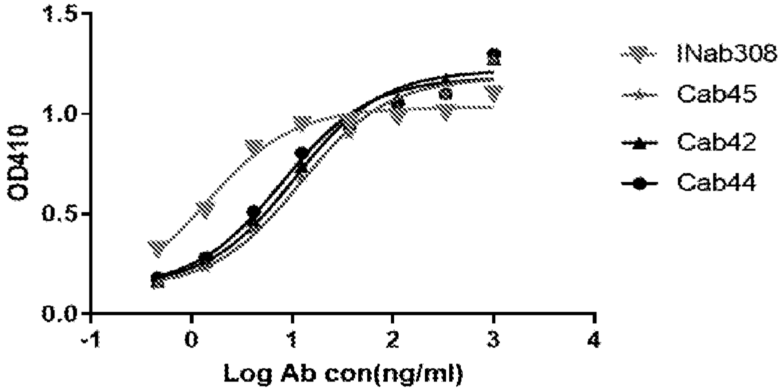

C5 ELISA Binding Assay:

At the same time, a binding ELISA was carried out to determine the binding affinity of the monoclonal antibodies Cab01, Cab03, Cab04, Cab05, Cab13 (reformatted as human IgG4) and the optimized antibodies Cab35, Cab38, Cab42, Cab44, and Cab45 (reformatted as human IgG1) to native full-length human complement component C5. INab308 was used as control, the ELISA binding assay was performed as described above. As shown in FIGS. 3A-3C, all the C5a antibodies exhibited quite weak binding affinity to human native C5, as compared to the control antibody INab308.

Non-Specificity Binding of Anti-C5a Antibodies

Cross-reactivity to BV ELISA: Using ELISA, the full-length antibodies Cab01, Cab03, Cab04, Cab05, Cab13 (reformatted as human IgG4), and the optimized antibodies Cab35 or Cab42 (reformatted as human IgG1) were tested for the cross-reactivity to BV particles.

This experiment detected the cross-reactivity to BV particles according to the method described previously (See Hötzel I, et al, 2012, mAbs 4:6, 753-760). In brief, the purified baculovirus was coated in an ELISA plate at 4° C. overnight. Co-incubated the test antibodies with baculovirus at room temperature, and washed with PBS before adding anti-human IgG antibody-HRP. After incubation at room temperature, washed with PBS, TMB was added to the wells for color development, and then read the absorbance at 450 nm.

Figure 4A:
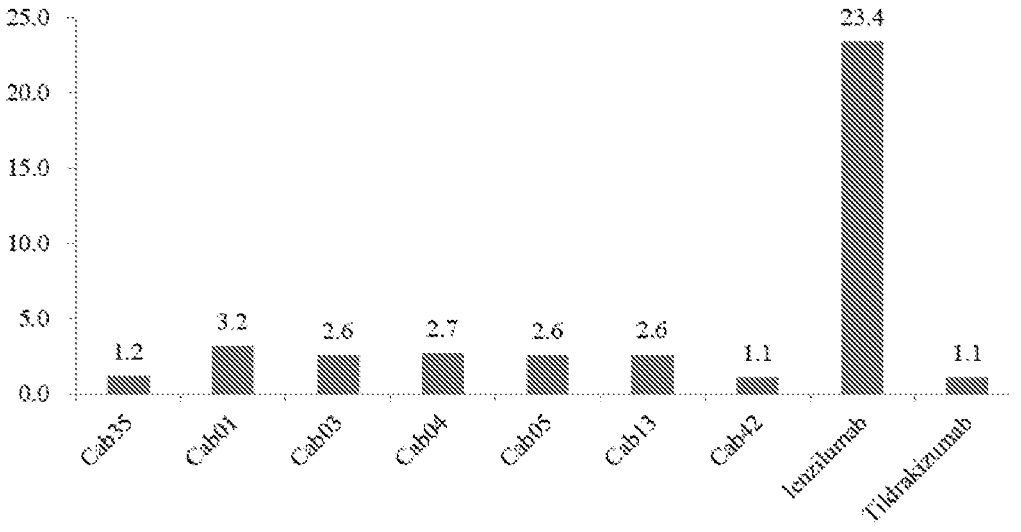
FIG. 4A shows the non-specific binding of the full-length antibody Cab01, Cab03, Cab04, Cab05, Cab13 (reformatted as human IgG4), or the optimized antibodies Cab35, Cab42 (reformatted as human IgG1) to BV particles.

As shown in FIG. 4A, all the antibodies didn't give rise to any significant polyspecificity reactions to BV particles as compared to the positive control lenzilumab.

Figure 4B:
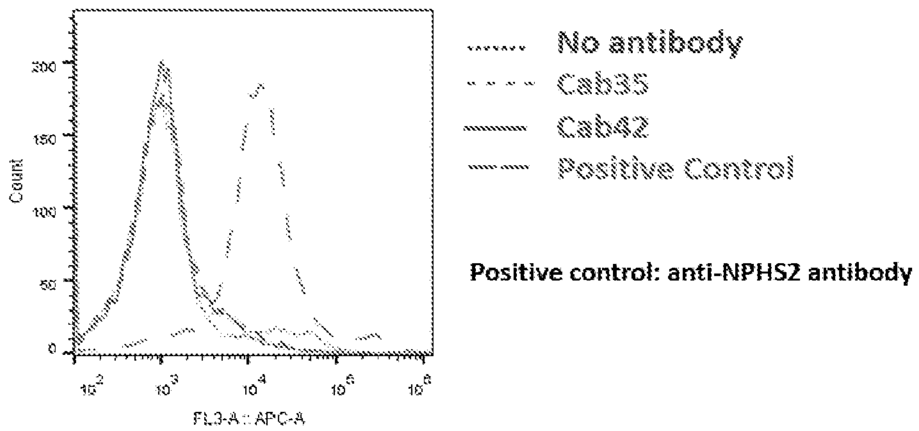
FIG. 4B shows the low cross-reactivity of the antibody Cab35-IgG1 or Cab42-IgG1 to C5a-negative 293 cells.

Cross-reactivity to 293 cells: Using FACS, the optimized antibodies Cab35-IgG1 and Cab42-IgG1 as well as the positive control anti-NPHS2 antibody were tested for the cross-reactivity to C5a-negative 293 cells. As shown in FIG. 4B, both Cab35-IgG1 and Cab42-IgG1 displayed similarly low levels of C5a-negative 293 cell binding as the negative control (no antibody), while the positive control antibody specific to NPHS2 on 293 cells displayed a higher level of binding to the cells. Taken together, these results indicated that all the selected anti-C5a antibodies displayed low levels of non-specific binding in BV ELISA and C5a-negative 293 cells cross-reactivity assay.

Characterization of Binding Affinity and Dissociation Constant (Kd)

The binding affinity of anti-C5a antibodies Cab05-IgG4 for human eC5a and human c5 was characterized using Biacore T200 (GE). Antibody Cab05-IgG4 was stabilized on sensor chip CM5. The affinities for eC5a and c5 at various concentrations were measured. The range of concentrations included 10, 5, 2.5, 1.25, 0.625, 0.3125, 0.15625, 0.078, 0.039, 0.0195, and 0 nM. The concentrations of 0.625 and 0 nM were repeated once. Using the SPR technology, the association and dissociation rates were measured, and binding affinity was determined. Table 7 shows the Kon, Koff, and Kd of Cab05-IgG4 for antigen C5 or eC5a, indicating that the anti-C5a antibody Cab05 exhibited high binding to C5a, and quite weak binding affinity to human C5.

TABLE 7

| Antibody | Antigen | Kon (1/Ms) | Koff (1/s) | Kd (M) |
|---|---|---|---|---|
| INab308 | C5 | 2.931E+05 | 2.178E−04 | 7.430E−10 |
| Cab05 | C5 | No signal | No signal | >1E−7 |
| INab308 | eC5a | 7.01E+06 | 3.25E−04 | 4.64E−11 |
| Cab05 | eC5a | 4.02E+05 | 4.22E−05 | 1.05E−10 |

Example 3: CD11b Blocking Assay in the Whole Blood

As CD11b up-regulation is a hallmark and a sensitive marker for neutrophil activation, CD11b levels on neutrophils were employed to evaluate the neutrophil activation. The human whole blood model was used to assess the blocking activity of the anti-C5a antibodies Cab01, Cab03, and Cab05 (reformatted as human IgG4) to recombinant human C5a and endogenous C5a in this study. Simultaneously, the blocking activity of the optimized antibodies Cab42, Cab43, Cab44, Cab45, and Cab46 (reformatted as human IgG1) to endogenous human C5a were assessed, INab308 was used as control. Human whole blood was incubated with human C5a alone, or combinations of human C5a and various antibodies with different concentrations. After incubation, cells were stained with detected antibody CD11b:FITC, After lysis of red blood cells, CD11b MFI was analyzed by flow cytometry for activation levels of blood neutrophils.

Figure 5A:
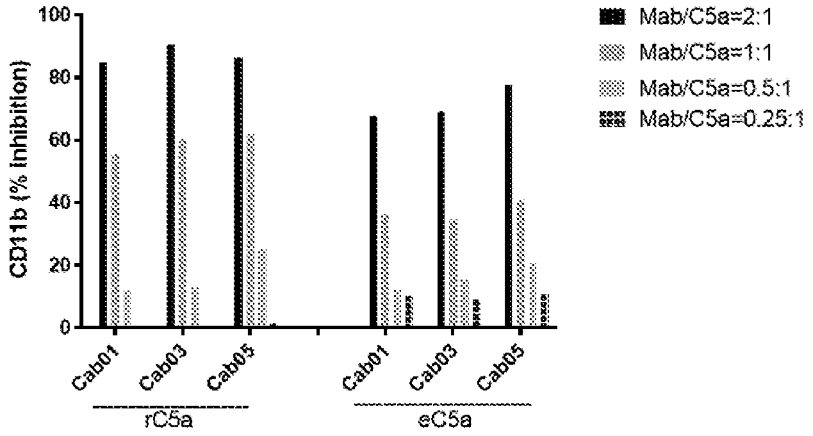
FIG. 5A shows the results of the CD11b blocking assay, showing the ability of the C5a antibody Cab01, Cab03, or Cab05 (reformatted as human IgG4) to block both human recombinant C5a and endogenous C5a stimulated the CD11b up-regulation on human neutrophils.

As shown in FIG. 5A, both human recombinant C5a and endogenous C5a strongly stimulated the CD11b up-regulation on human neutrophils. The overall blocking activity of C5a antibodies Cab01, Cab03 and Cab05 (reformatted as human IgG4) is dose-dependent. The presence of anti-C5a antibodies significantly decreased the CD11b expression on human neutrophils stimulated by recombinant C5a or endogenous C5a, even at an Ab:Ag molar ratio of 0.25:1.

Figure 5B:
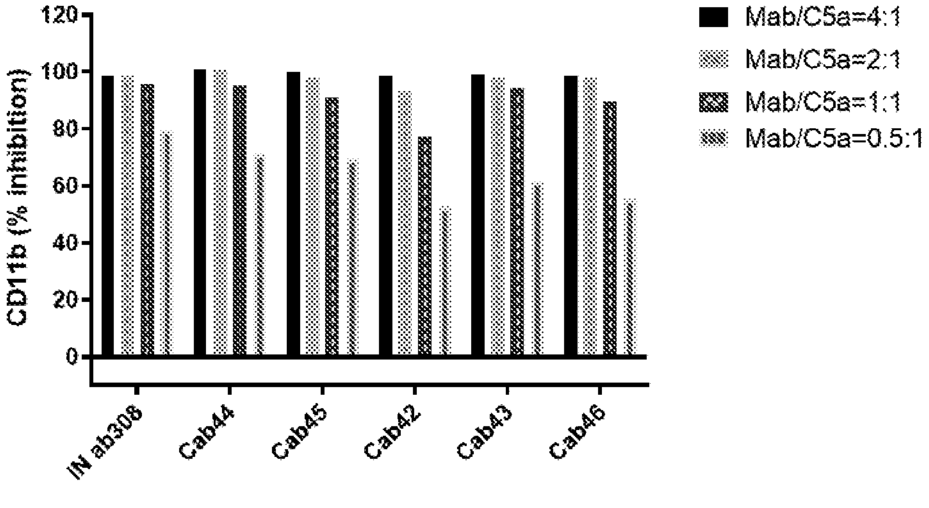
FIG. 5B shows the results of the CD11b blocking assay, showing the ability of the optimized C5a antibody Cab42, Cab43, Cab44, Cab45, or Cab46 (reformatted as human IgG1) to block human endogenous C5a stimulated the CD11b up-regulation on human neutrophils.

As shown in FIG. 5B, all the optimized antibodies significantly decreased the CD11b expression on human neutrophils stimulated by endogenous C5a, even at an Ab:Ag molar ratio of 0.5:1, showing comparable ability to inhibit the CD11b up-regulation with the reference antibody INab308.

Figure 5C:
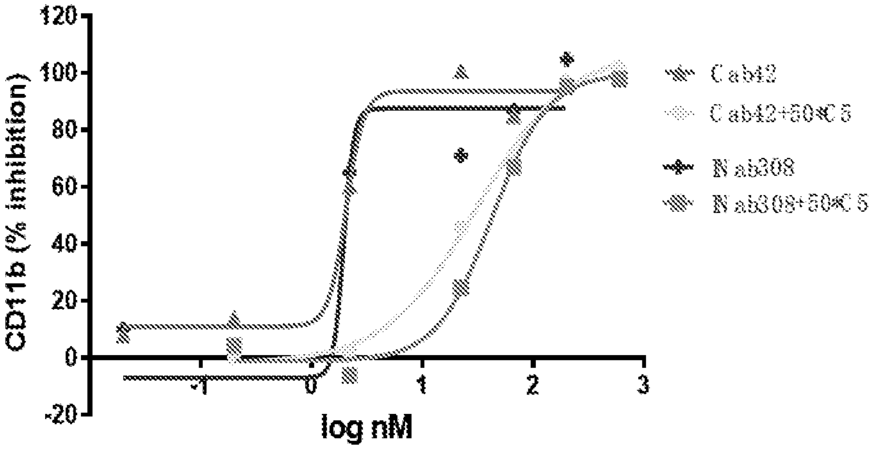
FIG. 5C shows results of the CD11b blocking assay for the ability of the optimized C5a antibody Cab42-IgG1 to block human endogenous C5a stimulated the CD11b up-regulation on human neutrophils even exist 50 times more molar C5 in the reaction, as compared to the reference antibody INab308.

As shown in FIG. 5C and Table 8, both the reference antibody INab308 and the optimized C5a antibody Cab42-IgG1 can inhibit the CD11b expression on human neutrophils stimulated by endogenous C5a, as the optimized C5a antibody Cab42-IgG1 was weakly bound to human C5, even when the amount of C5 existed in the reaction is 50 times more, it exhibited higher efficacy in decreasing endogenous C5a mediated CD11b up regulation on human neutrophils as compared to the reference antibody INab308.

TABLE 8

| Antibody | eC5a IC50(nM) | eC5a + 50*C5 IC50(nM) |
|---|---|---|
| Cab42-IgG1 | 2.05 | 31.04 |
| INab308 | 1.95 | 42.53 |

Example 4: Plasma Hemolytic Activity of Anti-C5a Antibodies

The complement system can be activated separately through three activation pathways, and finally forms a membrane attack complex. Under specific experimental conditions, it can directly attack the red blood cell membrane, causing red blood cell lysis. Based on this mechanism, the experiments were performed to evaluate whether the C5a antibodies can affect the biological activity of C5 convertase to cleave C5 to C5b.

Detection of the effect of C5a antibodies on complement-mediated classical activation pathways: The complement hemolysis 50% assay is a method for measuring the total classical complement activity in serum. This test is a lytic assay, which uses antibody sensitized erythrocytes as the activator of the classical complement pathway and various dilutions of the test serum to determine the amount required to give 50% lysis (CHSO). The percent hemolysis can be determined, for example, using a spectrophotometer. The complement hemolysis 50% assay provides an indirect measure of terminal complement complex (TCC) formation, since the TCC themselves are directly responsible for the hemolysis that is measured. The assay is well known and commonly practiced by those skilled in the art, e.g. as described in Limei Zhao et al. Front Immunol. 2017 May 31; 8:636; Zhao et al. Parasites & Vectors. 2014 Feb. 24; 7:80.

In brief, Guinea Pig red blood cell were prepared from fresh Guinea Pig whole blood by centrifugation, and then were sensitized with sheep anti-RBC antibody. It could activate the complement classical pathway of hemolysis, causing red blood cell lysis. Read the absorbance at 412 nm. The C5 antibody Eculizumab was used as control.

Detection of the effect of C5a antibodies on complement-mediated alternative activation pathways: In brief, Rabbit erythrocytes can activate the alternative pathway to form a membrane attack complex without sensitization by antibodies, resulting in lysis of rabbit erythrocytes. Adding ethylene glycol Ethylene Glycol tetraacetic acid (EGTA) to the reaction system, as it can chelate with $Ca^{2+}$ in plasma, but the binding capacity to $Mg^{2+}$ is weak, so the classical pathway was blocked. The complement hemolysis 50% assay described above was used to measure the alternative pathway activity, the C5 antibody Eculizumab was used as control.

Figure 6A:
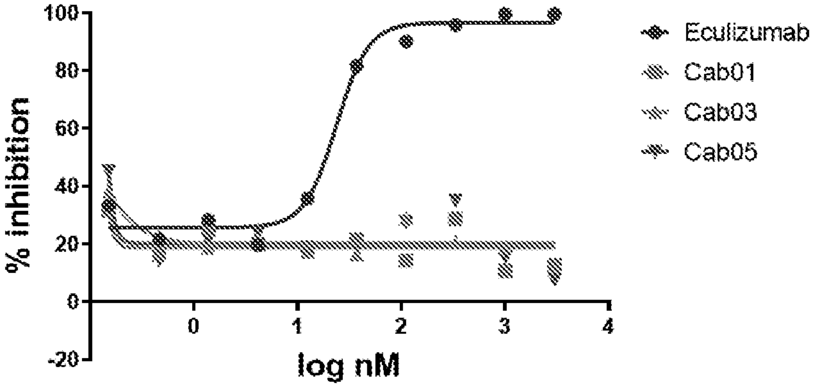
FIGS. 6A-6D show the results of the Plasma Hemolytic Activity of the C5a antibodies. The C5a antibodies Cab01, Cab03, Cab05 (reformatted as human IgG4) (FIG. 6A) and the optimized C5a antibodies Cab35, Cab42, Cab43, Cab44, Cab45, and Cab46 (reformatted as human IgG1) (FIG. 6B) didn't inhibit the plasma hemolytic activity in complement-mediated classical activation pathway as compared to the control Eculizumab. The C5a antibodies Cab01, Cab03, Cab05 (reformatted as human IgG4) (FIG. 6C) and the optimized C5a antibodies Cab35, Cab42, Cab43, Cab44, Cab45, and Cab46 (reformatted as human IgG1) (FIG. 6D) didn't inhibit the plasma hemolytic activity in complement-mediated alternative activation pathway as compared to the control Eculizumab.
Figure 6B:
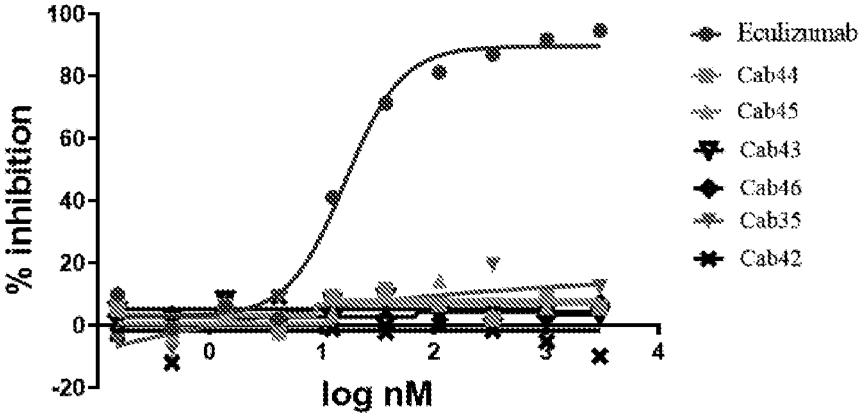
Figure 6C:
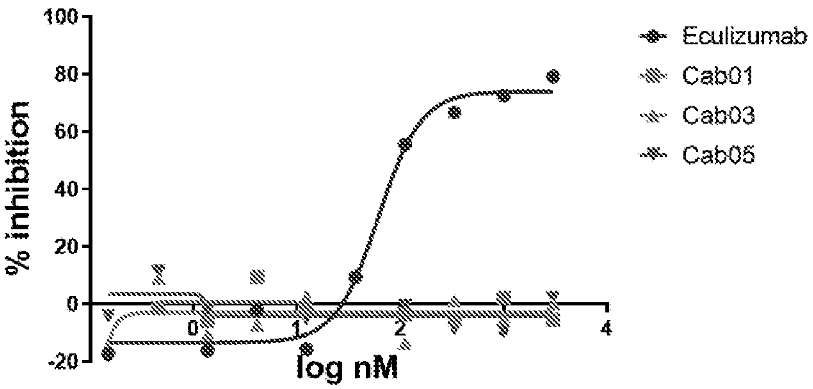
Figure 6D:
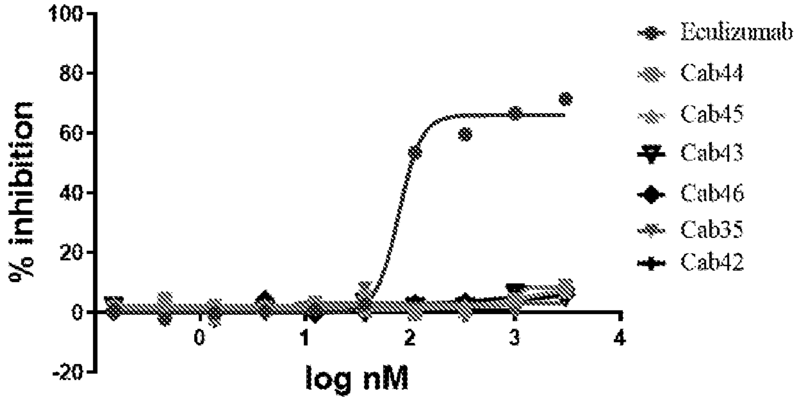

As shown in FIGS. 6A-6B, the addition of C5 antibody Eculizumab could inhibit the hemolytic response, and the degree of hemolysis was antibody-dose dependent, while the C5a antibodies Cab01, Cab03, Cab05 (reformatted as human IgG4) (FIG. 6A) and the optimized antibodies Cab35, Cab42, Cab43, Cab44, Cab45, and Cab46 (reformatted as human IgG1) (FIG. 6B) did not inhibit total classical complement activity. As shown in FIGS. 6C-6D, the addition of C5 antibody Eculizumab could inhibit the hemolytic response, while the C5a antibodies Cab01, Cab03, Cab05 (reformatted as human IgG4) (FIG. 6C) and the optimized antibodies Cab35, Cab42, Cab43, Cab44, Cab45, and Cab46 (reformatted as human IgG1) (FIG. 6D) did not inhibit alternative pathway activity. In conclusion, the C5a antibodies did not affect C5b function in neither complement-mediated classical activation pathways nor alternative activation pathways.

Example 5: In Vivo Biological Activity Assay of Anti-C5a Antibodies

C5a has a strong chemotactic effect on neutrophils. Intravenous injection of C5a into mouse will quickly cause neutrophils to migrate to peripheral tissues within a short time (3-5 minutes), and the neutrophils in the whole blood will significantly decrease.

In brief, the test antibody or control antibody was injected intraperitoneally 24 hours before the experiment, and 200 μg/kg of human C5a was injected intravenously on the day of the experiment. After 5 minutes, blood was collected for anticoagulation, and the number of neutrophils in whole blood was detected. The effect of anti-C5a antibodies was evaluated through the decrease of C5a-induced neutrophils chemotaxis.

Figure 7:
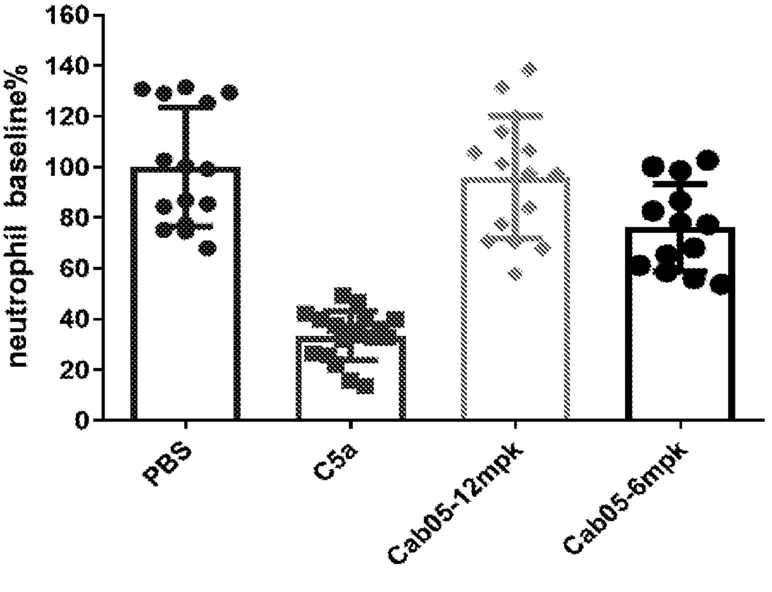
FIG. 7 shows the inhibitory effect of the anti-C5a antibody Cab05-IgG4 with different antibody doses in C5a-induced neutrophils chemotaxis.

As shown in FIG. 7, the C5a antibody Cab05-IgG4 exhibited great inhibitory effect in C5a-induced neutrophils chemotaxis ($P<0.0001$), and the inhibitory effect was antibody dose-dependent.

Example 6: Pharmacokinetics of Anti-C5a Antibodies

Figure 8:
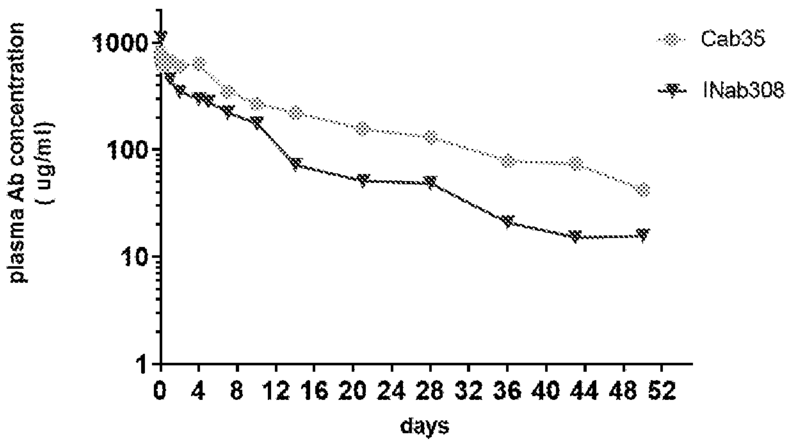
FIG. 8 shows the results of pharmacokinetics analysis of Cab35-IgG1 or the reference antibody INab308 in cynomolgus monkey as measured by ELISA.

PK studies in cynomolgus monkey: Four cynomolgus monkeys (approximately 3 kg by weight) were injected with either Cab35-IgG1 or the control antibody INab308 at a dose of 10 mg/kg. Specifically. Animal #1 and #2 were injected with INab308, and Animal #3 and #4 were injected with Cab35-IgG1. 6 mL of blood was collected from each animal the day before injection (D-1), one day after injection (D1), and subsequently at D2, D4, D8, D15, D22, D29, D36, D44 and D56. To evaluate the pharmacokinetics of the antibodies, plasma was collected from 1 mL of the blood sample collected at each time point by centrifuging for 15 minutes at 5000 g, and stored at −80° C. as 50 μL aliquots. The concentrations of Cab35-IgG1 and INab308 were analyzed using ELISA. Briefly, synthetic human C5a was used to coat the wells of a 96-well plate. On the following day, after washing with PBST, blocking with 200 μL PBS-milk for an hour, followed by another wash with PBST, the plasma was added and incubated for an hour at 37° C. The plate was washed with 0.1% TBST 6 times before 100 μL of Goat-anti-human Fc antibody-AP (1:3000 in PBS) was added to each well and incubated for an hour. After washing with 0.1% TBST 6 times, 50 μL of pNPP was added to each well, and color was developed for 10-20 minutes at 37° C. The results were read by a microplate reader at 410 nm. As shown in FIG. 8, the half-life of Cab35-IgG1 was longer than the control antibody INab308.

Example 7: Competitive ELISA Binding Assay

This experiment was performed to detect whether the C5a antibody Cab35-IgG1 or Cab42-IgG1 competes with the known antibodies INab308 (an anti-C5a antibody, InflaRx), MEDI-7814 (an anti-C5a antibody, MedImmune), or BNJ383 (an anti-C5a antibody, Alexion) for binding to human recombinant C5a. In brief, the first antibody was coated on an ELISA plate, blocked at 4° C. overnight. After washing with TBST, then adding the first antibody or other anti-C5a antibodies with different concentrations to the coated wells, 50 μL of Biotinylated C5a (1 μg/mL) was immediately added to the wells and incubated for 1 hour at 37° C. After incubation at 37° C., the wells were then washed with PBST buffer, the bound Biotinylated C5a was then detected by reaction with SA-HRP (horseradish peroxidase-labeled *Streptomyces* avidin) for 1 h at 37° C., then washed with PBST, TMB was added to the wells for color development, the reaction was terminated by addition of 50 μL of 2M $H_2SO_4$ per well, and then the absorbance at 410 nm was read. If other antibodies compete with the coated first antibody, the binding signal of C5a will be weakened.

Figure 9A:
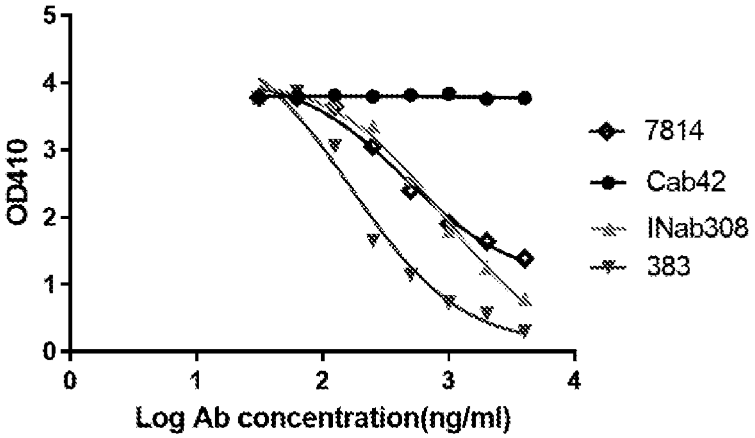
FIGS. 9A-9D show the results of the competitive ELISA binding curves of the antibody INab308, Cab42-IgG1, BNJ383 or MEDI-7814.
Figure 9B:
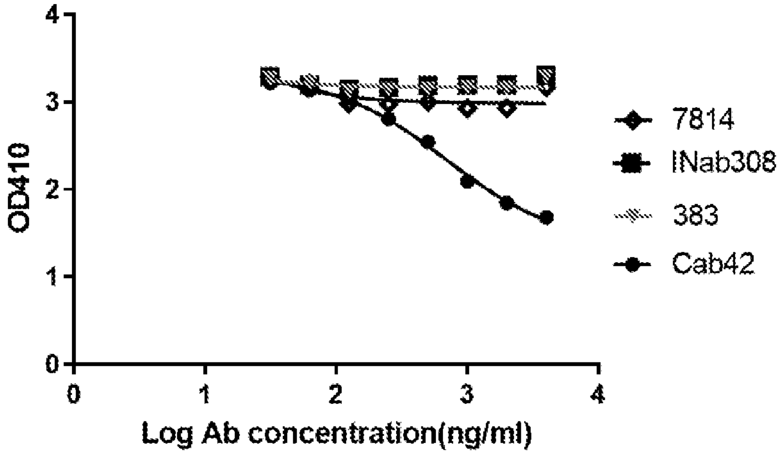
Figure 9C:
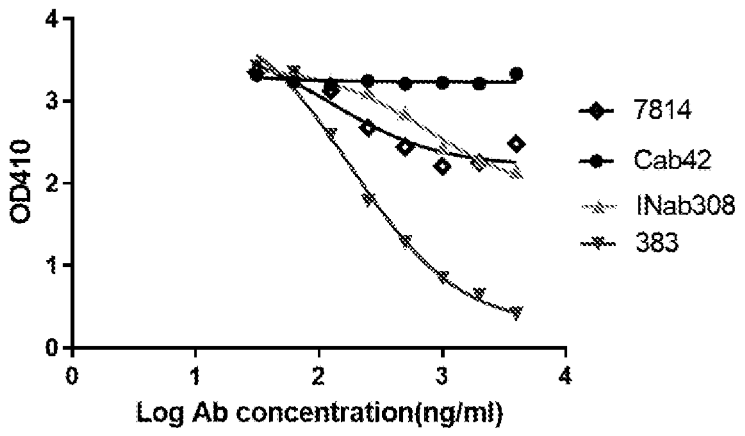
Figure 9D:
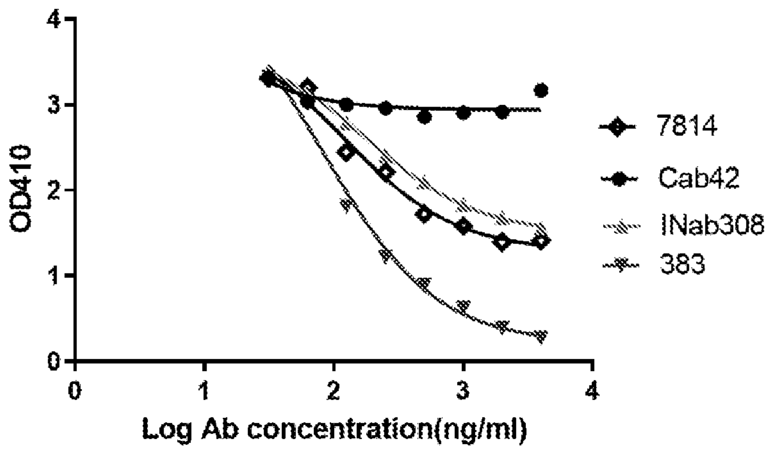
Figure 9E:
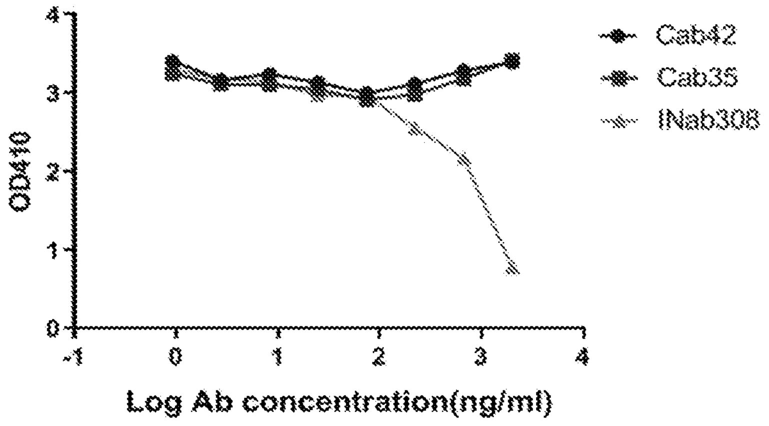
FIGS. 9E-9F show results of the competitive ELISA binding curves of the antibody INab308, Cab42-IgG1 or Cab35-
Figure 9F:
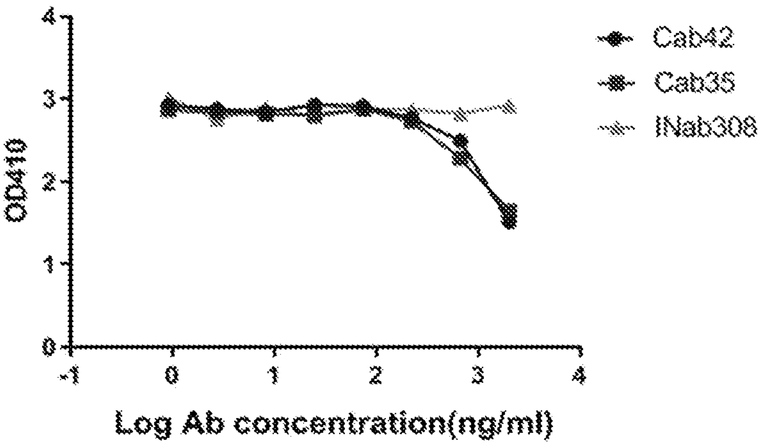
Figure 10A:
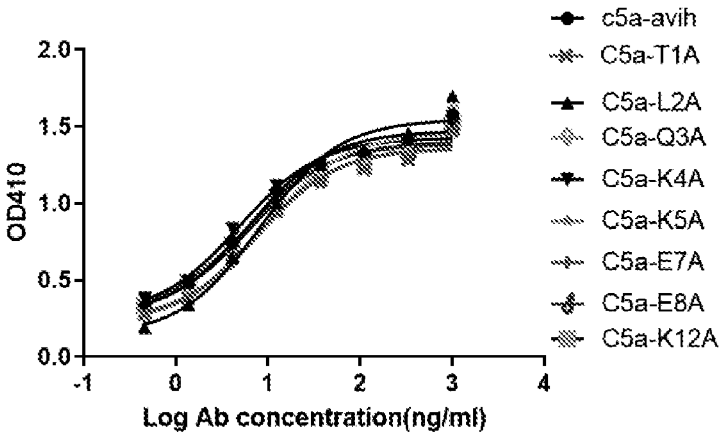
Figure 10B:
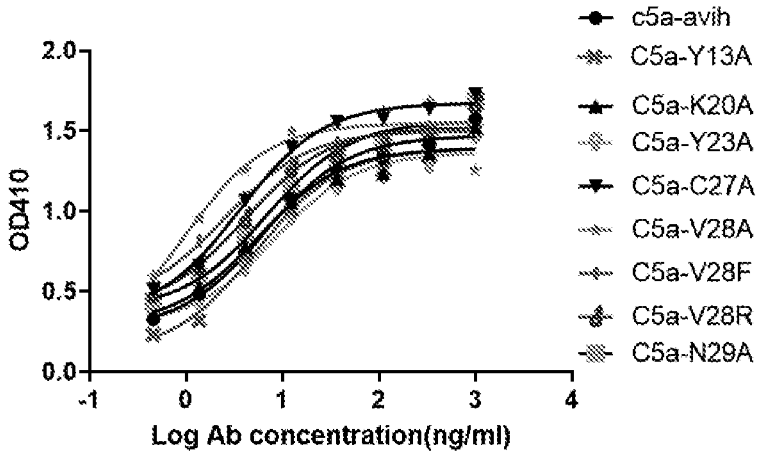
Figure 10C:
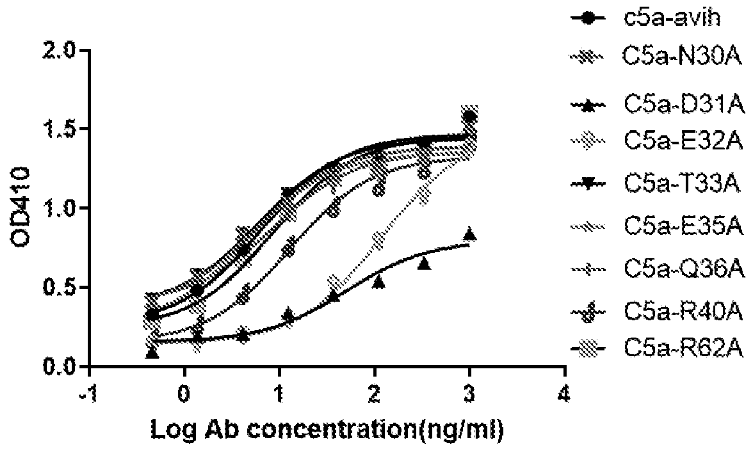
Figure 10D:
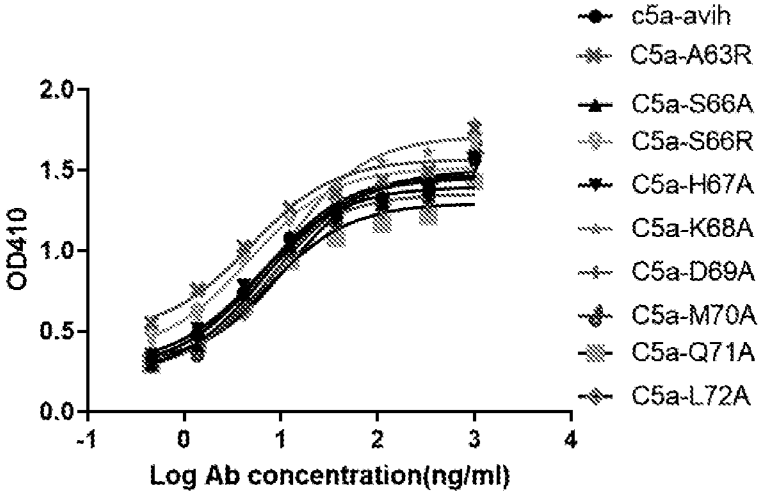
Figure 10E:
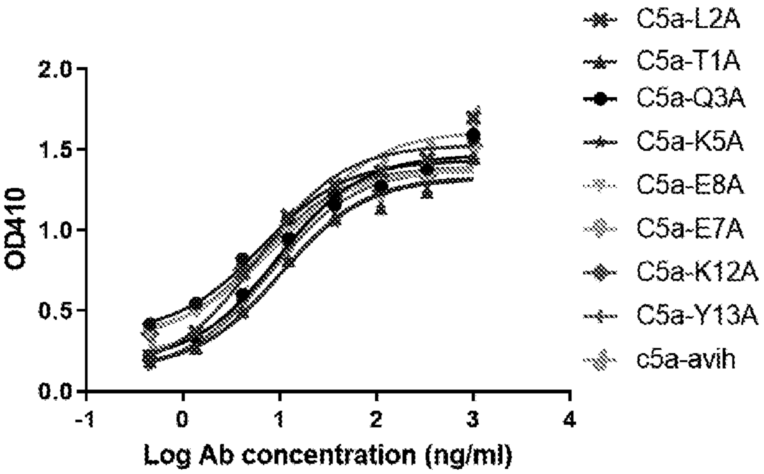
Figure 10F:
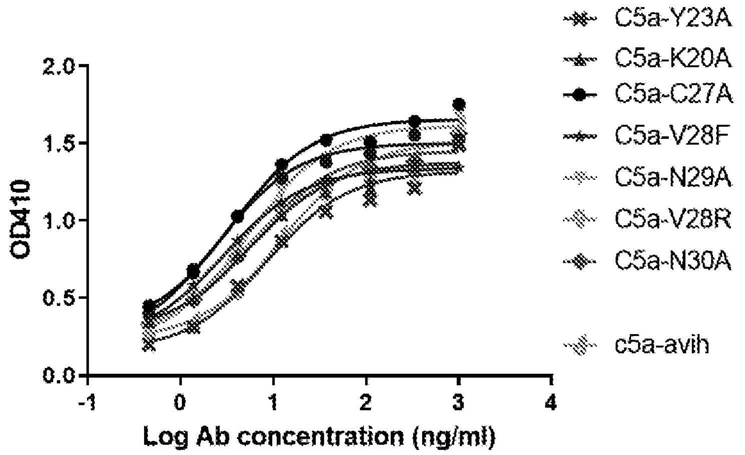
Figure 10G:
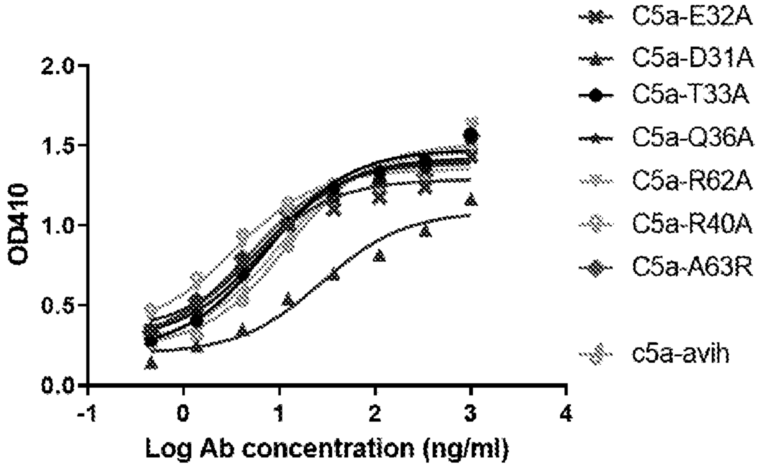
Figure 10H:
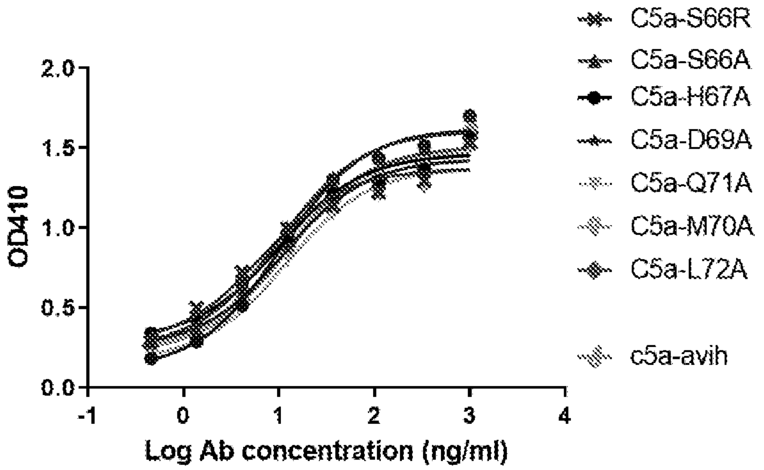
Figure 10I:
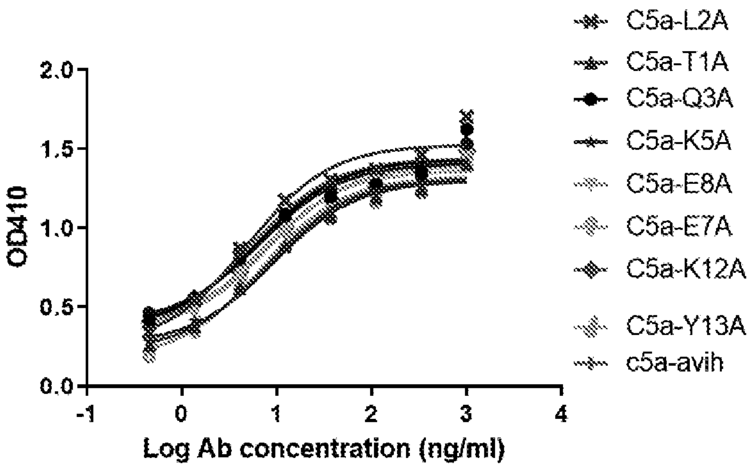
Figure 10J:
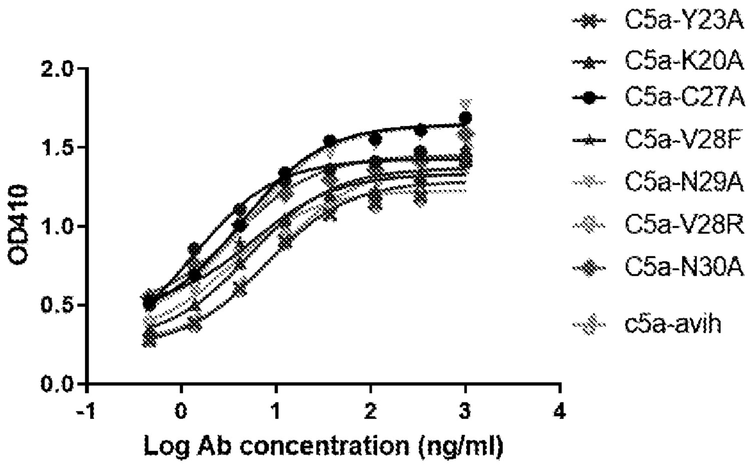
Figure 10K:
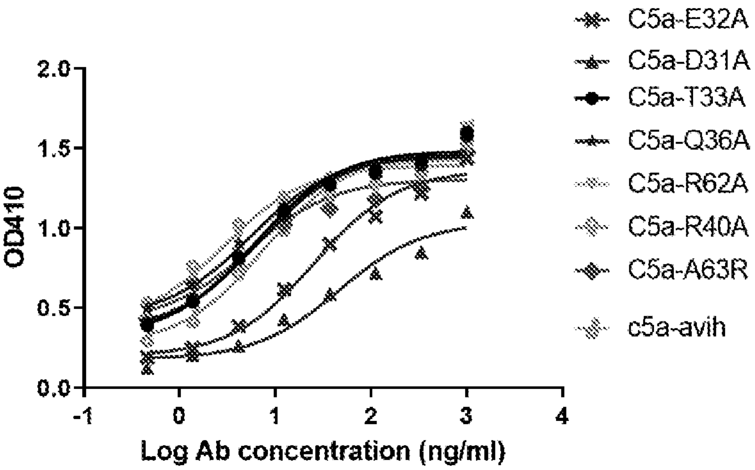
Figure 10L:
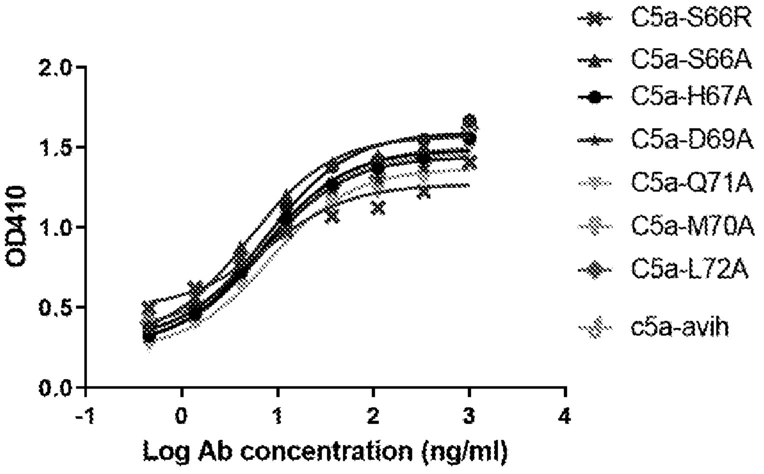

As shown in FIG. 9A, the C5a antibody INab308 did not compete with Cab42-IgG1, but competed with MEDI-7814 or BNJ383. As shown in FIG. 9B, the C5a antibody Cab42-IgG1 did not compete with INab308, MEDI-7814 or BNJ383. As shown in FIG. 9C, the C5a antibody BNJ383 did not compete with Cab42-IgG1, but partially competed with INab308 or MEDI-7814. As shown in FIG. 9D, the C5a antibody MEDI-7814 did not compete with Cab42-IgG1, but competed with INab308 or BNJ383. As shown in FIG. 9E, the C5a antibody INab308 did not compete with Cab35-IgG1 or Cab42-IgG1. As shown in FIG. 9F, the C5a antibody Cab35-IgG1 or Cab42-IgG1 did not compete with INab308, but competed with each other.

Example 8: Epitope Mapping of Anti-C5a Antibodies

Alanine scanning: Amino acid residues in proximity to the binding sites of C5a on C5aR were identified based on their crystal structures: C5 crystal structure (PDB: ID5I5K), C5a monomer NMR structure (PDB ID: 1KJS) and crystal structure of C5a and MEDI-7814 complex (an anti-C5a antibody, MedImmune) (PDB ID: 4uu9). Using the Discovery11 Studio software, the predicted binding sites for Cab42-IgG1 were identified, and the amino acid residues within the binding sites and in proximity to the binding sites were selected and subjected to alanine scanning. Some of these binding sites were also mutated to amino acids R or F, which is different from the amino acid A in size, in order to better improve whether the positions will affect the antibody binding. C5a proteins with these selected mutations were expressed.

The binding affinity of Cab42-IgG1 for each mutated C5a protein was analyzed using ELISA. FIGS. 10A-10D show the ELISA binding curves of the antibody Cab42-IgG1 for mutated C5a. Mutations at various positions of the amino acid sequence of the wild type C5a were generated using alanine scanning as described above. As shown in FIGS. 10A-10D, mutation at position D31 significantly affected the binding affinity of Cab42-IgG1, and was determined to be the most important mutation that affected C5a binding. In addition, the mutation at position E32 and position R40 also affected the binding affinity of Cab42-IgG1.

The binding affinity of Cab44-IgG1 for each mutated C5a protein was analyzed using ELISA. FIGS. 10E-10H show the ELISA binding curves of the antibody Cab44-IgG1 for mutated C5a. Mutations at various positions of the amino acid sequence of the wild type C5a were generated using alanine scanning as described above. As shown in FIGS. 10E-10H, mutation at position D31 significantly affected the binding affinity of Cab44-IgG1.

The binding affinity of Cab45-IgG1 for each mutated C5a protein was analyzed using ELISA. FIGS. 10I-10L show the ELISA binding curves of the antibody Cab45-IgG1 for mutated C5a. Mutations at various positions of the amino acid sequence of the wild type C5a were generated using alanine scanning as described above. As shown in FIGS. 10I-10L, mutation at position D31 significantly affected the binding affinity of Cab45-IgG1, and was determined to be the most important mutation that affected C5a binding. In addition, the mutation at position E32 also affected the binding affinity of Cab45-IgG1.

Figure 11A:
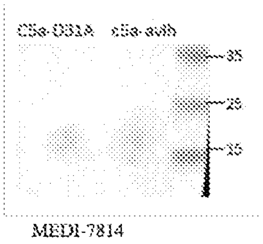
FIGS. 11A-11C show the Western blotting results of antibody MEDI-7814, Cab42-IgG1 or anti-His antibody binding with Avih-C5a or mutation Avih-C5a-D31A.
Figure 11B:
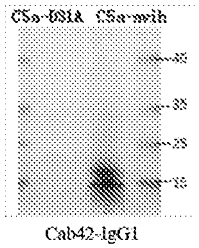
Figure 11C:
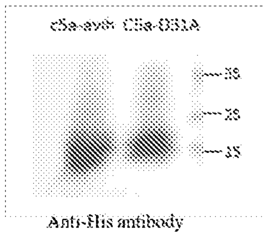

Determination of linear epitope: Based on these results, we used the antibody Cab42-IgG1 to determine whether the epitopes were linear or conformational by a Western blotting method. The Western blot is an important laboratory technique that allows for specific identification and characterization of proteins. Sodium dodecyl sulfate-polyacrylamide gel electrophoresis (SDS-PAGE)-separated proteins are electrophoretically transferred to a polyvinylidene fluoride (PVDF) membrane which is then incubated with specific antibodies, then developed to show the protein of interest. Methods for Western blotting are within the purview of those skilled in the art as described in Taylor S C et al. Biomed Res Int. 2014; 2014:361590. We expected that after structural destruction of the recombinant C5a by heating, if the anti-C5a antibody binds linear epitopes of human C5a, it can be directly detected by Western blotting. The antibodies MEDI-7814 and mouse anti-His were used as controls. The epitopes of MEDI-7814 were described in Colley C S, et al. MAbs. 2018 January; 10(1):104-117, the epitope encompasses human C5a residues Y13-C21 (inter a-helical loop 1/helix 2), D24 and G25 (helix 2), C27 (inter a-helical loop 2), R37 (Helix 3), R40-C47 (inter a-helical loop 3) and F51 (helix 4). As shown in FIG. 11A-11C, MEDI-7814 binds weakly to Avih-C5a, and there was no difference in binding strength between Avih-C5a and Avih-C5a-D31A mutation, indicating that the binding epitope of MEDI-7814 was conformational, and the epitope was not related to D31, consistent with the literature reported. In contrast, the antibody Cab42-IgG1 binds strongly to Avih-C5a, indicating that the binding epitope of Cab42-IgG1 was linear, while binds extremely weakly to the mutation Avih-C5a-D31A, indicating the position D31 was a key binding site.

Figure 11D:
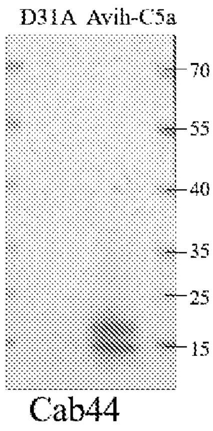
FIGS. 11D-11E show the Western blotting results of antibody Cab44-IgG1 or Cab45-IgG1 binding with human Avih-C5a or human C5a mutation Avih-C5a-D31A and FIG. 11F shows the SDS-PAGE result of human Avih-C5a and human C5a mutation Avih-C5a-D31A.
Figure 11E:
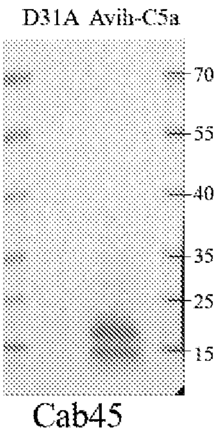
Figure 11F:
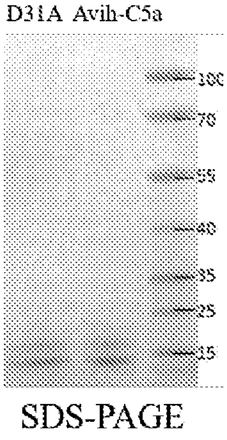

Also, we detected the antibody Cab44-IgG1 and Cab45-IgG1 to determine whether the position D31 was their key binding site, using the Western blotting method. SDS-PAGE of Avih-C5a and Avih-C5a-D31A mutation was used as controls. As shown in FIG. 11D-11F, the epitopes of Cab44-IgG1 or Cab45-IgG1 were linear, and position D31 also significantly affected the antibodies Cab44-IgG1 and Cab45-IgG1 binding to C5a.

Linear Peptide Mapping of Anti-C5a Antibodies:

as follows: (i) DGACVNNDETCEQRAARISLGPR (SEQ ID NO: 145); (ii) NDETCEQRAARISLGPR (SEQ ID NO: 146); or (iii) DETCEQRAAR (SEQ ID NO: 147). The isolated anti-C5a antibodies described herein specially binds to a peptide consisting of or comprising the sequence as follows: (i) DGACVNNDETCEQRAARISLGPR (SEQ ID NO: 145); (ii) NDETCEQRAARISLGPR (SEQ ID NO: 146); or (iii) DETCEQRAAR (SEQ ID NO: 147). The numbering of the amino acid residues in C5a is according to SEQ ID NO: 141.

TABLE 9

| peptide | position | sequence |
|---|---|---|
| C5a-p1 | 24-46 amino acid positions of human C5a (SEQ ID NO 141) | DGACVNNDETCEQRAARISLGPR (SEQ ID NO: 145) |
| C5a-p2 | 30-46 amino acid positions of human C5a (SEQ ID NO 141) | NDETCEQRAARISLGPR (SEQ ID NO: 146) |
| C5a-p4 | 31-40 amino acid positions of human C5a (SEQ ID NO 141) | DETCEQRAAR (SEQ ID NO: 147) |

The amino acid sequences of the C5a-p1, C5a-p2, and C5a-p4 were shown in Table 9, the sequence of peptide-Fc fusion: C5a-p1-Fc, C5a-p2-Fc, or C5a-p4-Fc, and the peptide C5a or Fc were synthesized and subcloned into the Eukaryotic expression vector pTT5. The Expression of C5a-p1-Fc, C5a-p2-Fc, or C5a-p4-Fc proteins was performed in 293 cells, and the purification was carried out according to the manufacturer's protocol.

The binding of the anti-C5a antibody Cab42 or INab308 to each of the peptide-Fc fusion was tested in an ELISA format. Briefly, linear peptides C5a-p1-Fc, C5a-p2-Fc, or C5a-p4-Fc corresponding to various regions within human C5a was diluted in coating buffer and placed on Microtiter Plates, The biotinylated anti-C5a antibody Cab42 or INab308 was added to each well followed by incubation at 37° C. for 1 h, the wells were then washed with PBST buffer, the bound Biotinylated C5a antibody was detected by reaction with SA-HRP (horseradish peroxidase-labeled *Streptomyces* Avidin) for 1 h at 37° C., then washed with PBST, TMB was added to the wells for color development, the reaction was terminated by addition of 50 μL of 3M NaOH per well, and then the absorbance at 410 nm was read.

Figure 12A:
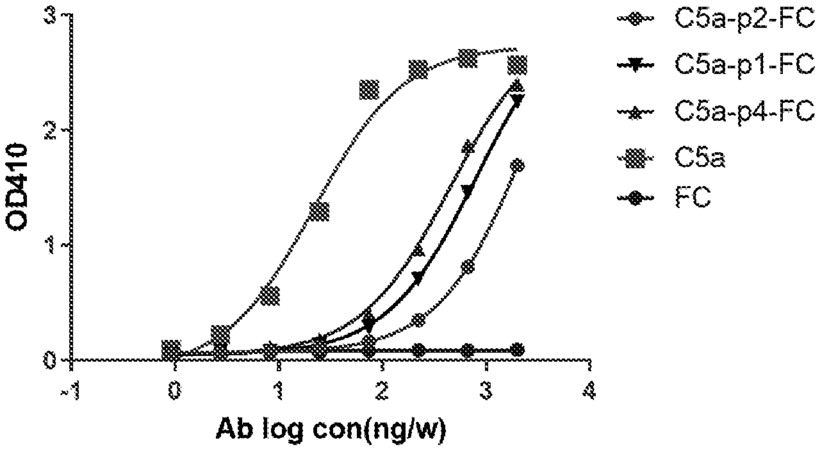
FIG. 12A shows the ELISA binding results of the antibody Cab42 that specifically binds to a peptide comprising the amino acid positions 24-46, positions 30-46, or positions 31-40 of human C5a as shown in SEQ ID NO 141.
Figure 12B:
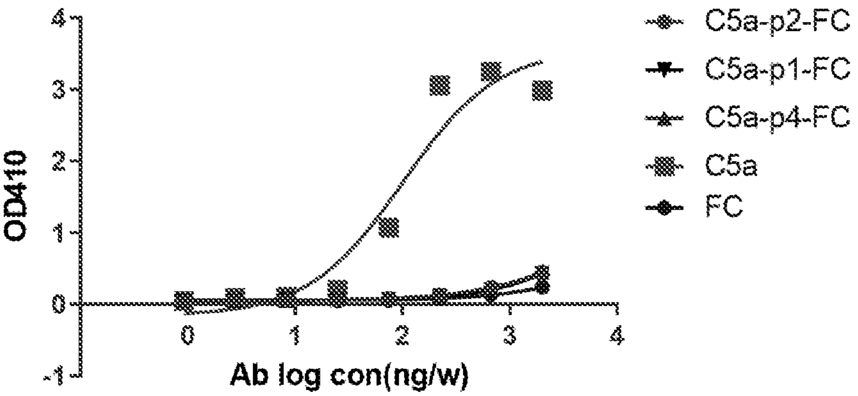
FIG. 12B shows the ELISA binding results of the antibody INab308, which doesn't bind to any of the 3 peptide-Fc fusions: C5a-p1-Fc, C5a-p2-Fc, or C5a-p4-Fc.

Results of these ELISA-based assays were shown in FIGS. 12A-12B, as shown in FIG. 12A, the antibody Cab42 that specifically binds to a peptide comprising the amino acid positions 24-46, positions 30-46, or positions 31-40 of SEQ ID NO: 141. But the antibody INab308 doesn't bind to any of the 3 peptide-Fc fusions:C5a-p1-Fc, C5a-p2-Fc, or C5a-p4-Fc as shown in FIG. 12B.

According to the result of Western Blot, Alanine scanning, and linear peptide mapping of anti-C5a antibodies, exemplary epitopes of antibodies Cab42-IgG1, Cab44-IgG1 and Cab45-IgG1 were identified as linear epitopes. Position D31 was the key binding site, position E32 and position R40 also affected the antibody binding to human C5a. The isolated anti-C5a antibodies described herein specially binds to residue D at position 31, or binds to residue D at position 31 and residue E at position 32, or binds to residue D at position 31, residue E at position 32 and residue R at position 40 of human C5a (SEQ ID NO: 141). The isolated anti-C5a antibodies described herein specially binds to an epitope of human C5a within, consisting of or comprising the sequence

Example 9: The Therapeutic Effects of Anti-C5a Antibody on Coronavirus-Related ARDS In Vivo A coronavirus-related ARDS animal model was established to evaluate the therapeutic effects of Cab35, Cab42, Cab44 and Cab45 antibodies in vivo.

ARDS animal model and Normal Control: C5a-humanized mice (available from Shanghai Model Organisms Center, Inc.) were utilized. The mice were raised under the condition of room temperature 20° C.-26° C., relative humidity of 40-70% and 12*h* light/dark cycle. On day 4, 3 and 2 before the study, the mice were infected with adenovirus carrying and expressing Covid-19 N protein (see Ting Gao etc., Highly pathogenic coronavirus N protein aggravates lung injury by MASP-2-mediated complement over-activation, medRxiv 2020.03.29.20041962; https://doi.org/10.1101/2020.03.29.20041962), with the dose of $7.5\times10^8$ PFU/100 μL/mouse/once a day and sodium chloride solution instead of the adenovirus was injected into the mice as Normal Control group. On day 0 (the day of the experiment), Cab35, Cab42, Cab44 or Cab45 antibody with different doses or sodium chloride solution was injected into mice in groups respectively as followed.

Groups and Administration: The mice were divided into groups and treated with different reagents respectively as followed: (1) Normal Control Group (n=6), injected with 100 μL 0.9% sodium chloride solution. (2) Model Control Group (n=10), injected with 100 μL 0.9% sodium chloride solution. (3) Low Dose Experimental Group (n=10), injected with antibody in the dose of 1 mg/kg. (4) Middle Dose Experimental Group (n=10), injected with antibody in the dose of 3 mg/kg. (5) High Dose Experimental Group (n=10), injected with antibody in the dose of 10 mg/kg. 30 min after administration, LPS-K235 (Sigma-Aldrich) was injected for the model group and all experimental groups (1 mg/mL, 100 μL/mouse). Sodium chloride solution was injected for the normal control group. All the reagents were injected via the tail vein in the study. This study was performed with the approval of the ethics committee at the Beijing Institute of Biotechnology and conformed to the relevant regulatory standards.

Survival Rate Analysis: At 12 h, 24 h, 36 h, 48 h, 60 h and 72 h after administration, the survival of the mice in all groups was observed and analyzed.

Whole Blood White Blood Cell Count: 72 h after administration, the mice were anaesthetized and orbital blood sampling was carried out. Whole blood white cell count and classification was performed with ADVIA® 2120 analyzer, including white blood cells (WBC), neutrophil granulocytes (Neut), lymphocytes (Lymph) and monocytes (Mono).

Survival Rate Results: all the animals in the normal group and high dose experimental group with different anti-C5a antibody (Cab35, Cab42, Cab44, or Cab45) survived within 72 hours after administration. In the model group, the total mortality was 30% (3/10). In the low dose group with different anti-C5a antibody (Cab35, Cab42, Cab44, or Cab45), the total mortality was 10-20% (1-2/10). Also, in the middle dose group with different anti-C5a antibody (Cab35, Cab42, Cab44, or Cab45), the total mortality was 10% (1/10). These results demonstrated that the anti-C5a antibodies of the present invention could effectively reduce or prevent the death of mice caused by a coronavirus, and increase the survival rate of the mice.

Whole Blood White Cell Count Results: the numbers of WBC, Lymph, or Mono of the mice in the model control group statistically significantly decreased when compared to that in the normal control group ($P<0.05$). Compared to the model group, all 3 experimental groups with different anti-C5a antibody (Cab35, Cab42, Cab44, or Cab45) showed increased levels of WBC and Lymph, with statistically significant differences between the model control group and either of the middle or high dose group ($P<0.05$). These results demonstrated that the anti-C5a antibodies of the present invention may help to recover the balance among the various immune cells in ARDS model mice.

Inflammatory cytokines assay Results: the levels of GM-CSF, IL-1β, IL-6, TNF-α and MCP-1 of the mice in the model control group statistically significantly increased when compared to that in the normal control group ($P<0.05$). When compared to the model control group, 3 experimental groups with different anti-C5a antibody (Cab35, Cab42, Cab44, or Cab45) all showed a reduction in levels of GM-CSF, IL-1β, IL-6, TNF-α, MCP-1 or C5a in a dose-dependent manner. Moreover, the levels of most of these cytokines in experimental groups were statistically significantly different from that in the model control ($P<0.05$). These results demonstrated that the anti-C5a antibodies of the present invention could significantly reduce cytokine storm and inflammatory reaction induced by Covid-19 in vivo.

The invention claimed is:

1. An isolated anti-C5a antibody or antigen binding fragment thereof, comprising:

(i) a $V_H$ comprising an HC-CDR1 comprising the amino acid sequence of SEQ ID NO: 2, an HC-CDR2 comprising the amino acid sequence of SEO ID NO: 10, and an HC-CDR3 comprising the amino acid sequence of SEQ ID NO: 32, and a $V_L$ comprising an LC-CDR1 comprising the amino acid sequence of SEO ID NO: 55, an LC-CDR2 comprising the amino acid sequence of SEQ ID NO: 57, and an LC-CDR3 comprising the amino acid sequence of SEO ID NO: 61;

(ii) a $V_H$ comprising an HC-CDR1 comprising the amino acid sequence of SEO ID NO: 2, an HC-CDR2 comprising the amino acid sequence of SEO ID NO: 22, and an HC-CDR3 comprising the amino acid sequence of SEQ ID NO: 32; and a $V_L$ comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61;

(iii) a $V_H$ comprising an HC-CDR1 comprising the amino acid sequence of SEQ ID NO: 2, an HC-CDR2 comprising to amino acid sequence of SEQ ID NO: 23, and an HC-CDR3 comprising the amino acid sequence of SEQ ID NO: 32; and a $V_L$ comprising an LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61;

(iv) a $V_H$ comprising an HC-CDR1 comprising the amino acid sequence of SEQ ID NO: 2, an HC-CDR2 comprising the amino acid sequence of SEQ ID NO: 24, and an HC-CDR3 comprising the amino acid sequence of SEQ ID NO: 32; and a $V_L$ comprising an LC-CDR1 comprising the amino acid sequence of SEQ ID NO: 42, an LC-CDR2 comprising an amino acid sequence of SEQ ID NO: 57, and an LC-CDR3 comprising the amino acid sequence of SEQ ID NO: 61;

(v) a $V_H$ comprising an HC-CDR1 comprising the amino acid sequence of SEQ ID NO: 2, an HC-CDR2 comprising the amino acid sequence of SEQ ID NO: 25, and an HC-CDR3 comprising the amino acid sequence of SEQ ID NO: 32; and a $V_L$ comprising an LC-CDR1 comprising an amino acid sequence of SEQ ID NO: 42, an LC-CDR2 comprising the amino acid sequence of SEQ ID NO: 57, and an LC-CDR3 comprising the amino acid sequence of SEQ ID NO: 61;

(vi) a $V_H$ comprising an HC-CDR1 comprising the amino acid sequence of SEQ ID NO: 2, an HC-CDR2 comprising the amino acid sequence of SEQ ID NO: 26, and an HC-CDR3 comprising the amino acid sequence of SEQ ID NO: 32; and a $V_L$ comprising the LC-CDR1 comprising t amino acid sequence of SEQ ID NO: 42, an LC-CDR2 comprising an amino acid sequence of SEQ ID NO: 57, and an LC-CDR3 comprising the amino acid sequence of SEQ ID NO: 61;

(vii) a $V_H$ comprising an HC-CDR1 comprising the amino acid sequence of SEQ ID NO: 2, an HC-CDR2 comprising the amino acid sequence of SEQ ID NO: 27, and an HC-CDR3 comprising the amino acid sequence of SEQ ID NO: 32; and a $V_L$ comprising the LC-CDR1 comprising am amino acid sequence of SEQ ID NO: 42, an LC-CDR2 comprising the amino acid sequence of SEQ ID NO: 57, and an LC-CDR3 comprising the amino acid sequence of SEQ ID NO: 61;

(viii) a $V_H$ comprising an HC-CDR1 comprising the amino acid sequence of SEQ ID NO: 2, an HC-CDR2 comprising the amino acid sequence of SEQ ID NO: 28, and an HC-CDR3 comprising the amino acid sequence of SEQ ID NO: 32; and a $V_L$ comprising an LC-CDR1 comprising the amino acid sequence of SEQ ID NO: 42, an LC-CDR2 comprising an amino acid sequence of SEQ ID NO: 57, and an LC-CDR3 comprising the amino acid sequence of SEQ ID NO: 61;

(ix) a $V_H$ comprising an HC-CDR1 comprising the amino acid sequence of SEQ ID NO: 2, an HC-CDR2 comprising the amino acid sequence of SEQ ID NO: 29, and an HC-CDR3 comprising the amino acid sequence of SEQ ID NO: 32; and a $V_L$ comprising the LC-CDR1 comprising the amino acid sequence of SEQ ID NO: 42, an LC-CDR2 comprising the amino acid sequence of SEQ ID NO: 57, and an LC-CDR3 comprising the amino acid sequence of SEQ ID NO: 61; or (xi) a $V_H$ comprising an HC-CDR1 comprising the amino acid sequence of SEQ ID NO: 2, an HC-CDR2 comprising the amino acid sequence of SEQ ID NO: 23, and an HC-CDR3 comprising the amino acid sequence of SEQ ID NO: 32; and a $V_L$ comprising an LC-CDR1 comprising the amino acid sequence of SEQ ID NO: 56, an LC-CDR2 comprising the amino acid sequence of SEQ ID NO: 57, and an LC-CDR3 comprising the amino acid sequence of SEQ ID NO: 61.

2. The isolated anti-C5a antibody or antigen binding fragment thereof of claim 1, comprising:

(i) a $V_H$ comprising the amino acid sequence of SEQ ID NO: 100 or a variant thereof having at least about 90% sequence identity to the amino acid sequence of SEQ ID NO: 100; and a $V_L$ comprising the amino acid sequence of SEQ ID NO: 136 or a variant thereof having at least about 90% sequence identity to the amino acid sequence of SEQ ID NO: 136;

(ii) a $V_H$ comprising the amino acid sequence of SEQ ID NO: 101 or a variant thereof having at least about 90% sequence identity to the amino acid sequence of SEQ ID NO: 101; and a $V_L$ comprising the amino acid sequence of SEQ ID NO: 135 or a variant thereof having at least about 90% sequence identity to the amino acid sequence of SEQ ID NO: 135;

(iii) a $V_H$ comprising the amino acid sequence of SEQ ID NO: 102 or a variant thereof having at least about 90% sequence identity to the amino acid sequence of SEQ ID NO: 135; and a $V_L$ comprising the amino acid sequence of SEQ ID NO: 135 or a variant thereof having at least about 90% sequence identity to the amino acid sequence of SEQ ID NO: 135;

(iv) a $V_H$ comprising the amino acid sequence of SEQ ID NO: 101 or a variant thereof having at least about 90% sequence identity to the amino acid sequence of SEQ ID NO: 103; and a $V_L$ comprising the amino acid sequence of SEQ ID NO: 135 or a variant thereof having at least about 90% sequence identity to the amino acid sequence of SEQ ID NO: 135;

(v) a $V_H$ comprising the amino acid sequence of SEQ ID NO: 104 or a variant thereof having at least about 90% sequence identity to the amino acid sequence of SEQ ID NO: 104; and a $V_L$ comprising the amino acid sequence of SEQ ID NO: 135 or a variant thereof having at least about 90% sequence identity to the amino acid sequence of SEQ ID NO: 135;

(vi) a $V_H$ comprising the amino acid sequence of SEQ ID NO: 105 or a variant thereof having at least about 90% sequence identity to the amino acid sequence of SEQ ID NO: 105; and a $V_L$ comprising the amino acid sequence of SEQ ID NO: 135 or a variant thereof having at least about 90% sequence identity to the amino acid sequence of SEQ ID NO: 135;

(vii) a $V_H$ comprising the amino acid sequence of SEQ ID NO: 106 or a variant thereof having at least about 90% sequence identity to the amino acid sequence of SEQ ID NO: 106; and a $V_L$ comprising the amino acid sequence of SEQ ID NO: 135 or a variant thereof having at least about 90% sequence identity to the amino acid sequence of SEQ ID NO: 135;

(viii) a $V_H$ comprising the amino acid sequence of SEQ ID NO: 107 or a variant thereof having at least about 90% sequence identity to the amino acid sequence of SEQ ID NO: 107; and a $V_L$ comprising the amino acid sequence of SEQ ID NO: 135 or a variant thereof having at least about 90% sequence identity to the amino acid sequence of SEQ ID NO: 135;

(ix) a $V_H$ comprising the amino acid sequence of SEQ ID NO: 108 or a variant thereof having at least about 90% sequence identity to the amino acid sequence of SEQ ID NO: 108; and a $V_L$ comprising the amino acid sequence of SEQ ID NO: 135 or a variant thereof having at least about 90% sequence identity to the amino acid sequence of SEQ ID NO: 135; or (x) a $V_H$ comprising the amino acid sequence of SEQ ID NO: 109 or a variant thereof having at least about 90% sequence identity to the amino acid sequence of SEQ ID NO: 109; and a $V_L$ comprising the amino acid sequence of SEQ ID NO: 138 or a variant thereof having at least about 90% sequence identity to the amino acid sequence of SEQ ID NO: 138.

3. The isolated anti-C5a antibody or antigen binding fragment thereof according to claim 1, wherein:

(i) the anti-C5a antibody or antigen binding fragment thereof comprises an Fc fragment; and/or (ii) the anti-C5a antibody or antigen binding fragment thereof is a full-length IgG antibody; and/or (iii) the anti-C5a antibody or antigen binding fragment thereof is a full-length IgG1 or IgG4 antibody; and/or (iv) the anti-C5a antibody or antigen binding fragment thereof binds to human C5a with a Kd from about 0.1 pM to about 1 nM; and/or (v) the anti-C5a antibody or antigen binding fragment thereof binds to free human C5a polypeptide in the presence of a 2-fold or more molar excess of uncleaved, native human C5.

4. The isolated anti-C5a antibody or antigen binding fragment thereof of claim 1, wherein the anti-C5a antibody or antigen binding fragment thereof is chimeric or humanized.

5. The isolated anti-C5a antibody or antigen binding fragment thereof according to claim 1, wherein the anti-C5a antibody or antigen binding fragment thereof is selected from the group consisting of a Fab, a Fab' a F(ab)'2, a Fab'-SH, a single-chain Fv (scFv), an Fv fragment, and a diabody.

6. An isolated nucleic acid molecule that encodes the anti-C5a antibody or antigen binding fragment thereof according to claim 1.

7. A vector comprising the isolated nucleic acid molecule of claim 6.

8. An isolated host cell comprising the anti-C5a antibody or antigen binding fragment thereof of claim 1, an isolated nucleic acid, or a vector;

wherein the isolated nucleic acid molecule encodes the anti-C5a antibody or antigen binding fragment thereof according to claim 1; and the vector comprises the isolated nucleic acid molecule.

9. A method of producing an anti-C5a antibody or antigen binding fragment thereof, comprising:

a) expressing the anti-C5a antibody or antigen binding fragment thereof by culturing the isolated host cell of claim 8; and b) obtaining the expressed anti-C5a antibody or antigen binding fragment thereof from the isolated host cell.

10. A pharmaceutical composition comprising the anti-C5a antibody or antigen binding fragment thereof according to claim 1, an isolated nucleic acid, a vector, or an isolated host cell, and a pharmaceutically acceptable carrier;

wherein the isolated nucleic acid molecule encodes the anti-C5a antibody or antigen binding fragment thereof according to claim 1; the vector comprises the isolated nucleic acid molecule; and the isolated host cell comprises the anti-C5a antibody or antigen binding fragment thereof of claim 1, the isolated nucleic acid, or the vector.

11. A method of treating a disease or condition in an individual in need thereof, comprising administering to the individual an effective amount of the pharmaceutical composition of claim 10; wherein the individual has inflammatory response syndrome (SIRS), sepsis, severe sepsis, septic shock, ischemia reperfusion injury, pneumonia, acute or chronic graft rejection, graft versus host disease, glomerulonephritis, rheumatoid arthritis, inflammatory bowel disease, or Crohn's disease.

* * * * *

SEQUENCE LISTING

```
<160> NUMBER OF SEQ ID NOS: 147

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Lys Tyr Tyr Met Gln
1               5


<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Asp Tyr Tyr Met Gln
1               5


<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Asp Tyr Tyr Leu Gln
1               5


<210> SEQ ID NO 4
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 4

Asp Phe Tyr Met Gln
1               5


<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Asp Tyr Tyr Ile Gln
1               5


<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Asn Tyr Tyr Ile Gln
1               5


<210> SEQ ID NO 7
<211> LENGTH: 19
<212> TYPE: PRT
<213> ORGANISM: Artificial Sequence
<220> FEATURE:
<223> OTHER INFORMATION: Synthetic Construct

<400> SEQUENCE: 7

Leu Ile Arg Asn Lys Ala Asn Gly Gly Thr Ala Glu Tyr Val Ala Ser
1               5                   10                  15

Val Lys Asp


<210> SEQ ID NO 8
<211> LENGTH: 19
<212> TYPE: PRT
<213> ORGANISM: Artificial Sequence
<220> FEATURE:
<223> OTHER INFORMATION: Synthetic Construct

<400> SEQUENCE: 8

Leu Ile Arg Lys Lys Val Asn Gly Gly Thr Thr Glu Tyr Ala Ala Ser
1               5                   10                  15

Val Lys Gly


<210> SEQ ID NO 9
<211> LENGTH: 19
<212> TYPE: PRT
<213> ORGANISM: Artificial Sequence
<220> FEATURE:
<223> OTHER INFORMATION: Synthetic Construct

<400> SEQUENCE: 9

Leu Ile Arg Asn Lys Ala Ile Gly Gly Thr Thr Gln Tyr Ala Ala Ser
1               5                   10                  15

Val Lys Gly


<210> SEQ ID NO 10
<211> LENGTH: 19
```

<212> TYPE: PRT
<213> ORGANISM: Artificial Sequence
<220> FEATURE:
<223> OTHER INFORMATION: Synthetic Construct

<400> SEQUENCE: 10

Leu Ile Arg Asn Lys Ala Val Gly Gly Thr Thr Gln Tyr Ala Ala Ser
1 5 10 15

Val Lys Gly

<210> SEQ ID NO 11
<211> LENGTH: 19
<212> TYPE: PRT
<213> ORGANISM: Artificial Sequence
<220> FEATURE:
<223> OTHER INFORMATION: Synthetic Construct

<400> SEQUENCE: 11

Leu Ile Arg Asn Lys Ala Ile Gly Glu Thr Thr Glu Tyr Ala Ala Ser
1 5 10 15

Val Lys Gly

<210> SEQ ID NO 12
<211> LENGTH: 19
<212> TYPE: PRT
<213> ORGANISM: Artificial Sequence
<220> FEATURE:
<223> OTHER INFORMATION: Synthetic Construct

<400> SEQUENCE: 12

Leu Ile Arg Thr Lys Arg Tyr Gly Gly Thr Ser Glu Tyr Ala Ala Ser
1 5 10 15

Val Lys Gly

<210> SEQ ID NO 13
<211> LENGTH: 19
<212> TYPE: PRT
<213> ORGANISM: Artificial Sequence
<220> FEATURE:
<223> OTHER INFORMATION: Synthetic Construct

<400> SEQUENCE: 13

Leu Ile Arg Asn Lys Pro Tyr Gly Gly Thr Ala Glu Tyr Ala Ala Ser
1 5 10 15

Val Lys Gly

<210> SEQ ID NO 14
<211> LENGTH: 19
<212> TYPE: PRT
<213> ORGANISM: Artificial Sequence
<220> FEATURE:
<223> OTHER INFORMATION: Synthetic Construct

<400> SEQUENCE: 14

Leu Ile Arg Asn Lys Ala Ile Gly Glu Thr Thr Gln Tyr Ala Ala Ser
1 5 10 15

Val Lys Gly

<210> SEQ ID NO 15
<211> LENGTH: 19
<212> TYPE: PRT
<213> ORGANISM: Artificial Sequence
<220> FEATURE:
<223> OTHER INFORMATION: Synthetic Construct

<400> SEQUENCE: 15

Leu Ile Arg Asn Lys Ala Val Gly Glu Thr Val Gln Tyr Ala Ala Ser
1               5                   10                  15

Leu Lys Gly

<210> SEQ ID NO 16
<211> LENGTH: 19
<212> TYPE: PRT
<213> ORGANISM: Artificial Sequence
<220> FEATURE:
<223> OTHER INFORMATION: Synthetic Construct

<400> SEQUENCE: 16

Leu Ile Arg Asn Lys Ala Val Gly Gly Thr Thr Ser Tyr Ala Ala Ser
1               5                   10                  15

Val Lys Gly

<210> SEQ ID NO 17
<211> LENGTH: 19
<212> TYPE: PRT
<213> ORGANISM: Artificial Sequence
<220> FEATURE:
<223> OTHER INFORMATION: Synthetic Construct

<400> SEQUENCE: 17

Leu Ile Arg Asn Lys Ala Ile Gly Glu Thr Ala Glu Tyr Ala Ala Ser
1               5                   10                  15

Val Lys Gly

<210> SEQ ID NO 18
<211> LENGTH: 19
<212> TYPE: PRT
<213> ORGANISM: Artificial Sequence
<220> FEATURE:
<223> OTHER INFORMATION: Synthetic Construct

<400> SEQUENCE: 18

Leu Ile Arg Asn Lys Ala Ile Gly Glu Thr Thr Glu Phe Ala Ala Ser
1               5                   10                  15

Val Lys Gly

<210> SEQ ID NO 19
<211> LENGTH: 19
<212> TYPE: PRT
<213> ORGANISM: Artificial Sequence
<220> FEATURE:
<223> OTHER INFORMATION: Synthetic Construct

<400> SEQUENCE: 19

Leu Ile Arg Asn Lys Ala Asn Gly Gly Thr Thr Glu Tyr Ala Ala Ser
1               5                   10                  15

Val Lys Gly

<210> SEQ ID NO 20
<211> LENGTH: 19
<212> TYPE: PRT
<213> ORGANISM: Artificial Sequence
<220> FEATURE:
<223> OTHER INFORMATION: Synthetic Construct

<400> SEQUENCE: 20

Leu Ile Arg Asn Lys Ala Ile Gly Gly Thr Val Glu Tyr Ala Ala Ser 1 5 10 15

Val Lys Gly

<210> SEQ ID NO 21
<211> LENGTH: 19
<212> TYPE: PRT
<213> ORGANISM: Artificial Sequence
<220> FEATURE:
<223> OTHER INFORMATION: Synthetic Construct

<400> SEQUENCE: 21

Leu Ile Arg Asn Lys Ala Val Gly Gly Thr Thr Thr Tyr Ala Ala Ser
1 5 10 15

Val Lys Gly

<210> SEQ ID NO 22
<211> LENGTH: 19
<212> TYPE: PRT
<213> ORGANISM: Artificial Sequence
<220> FEATURE:
<223> OTHER INFORMATION: Synthetic Construct

<400> SEQUENCE: 22

Leu Ile Arg Asn Lys Ala Val Gly Gly Thr Thr Glu Tyr Ala Ala Ser
1 5 10 15

Val Lys Gly

<210> SEQ ID NO 23
<211> LENGTH: 19
<212> TYPE: PRT
<213> ORGANISM: Artificial Sequence
<220> FEATURE:
<223> OTHER INFORMATION: Synthetic Construct

<400> SEQUENCE: 23

Leu Ile Arg Asn Lys Ala Val Gly Glu Thr Thr Gln Tyr Ala Ala Ser
1 5 10 15

Val Lys Gly

<210> SEQ ID NO 24
<211> LENGTH: 19
<212> TYPE: PRT
<213> ORGANISM: Artificial Sequence
<220> FEATURE:
<223> OTHER INFORMATION: Synthetic Construct

<400> SEQUENCE: 24

Leu Ile Arg Asn Lys Ala Val Gly Glu Thr Thr Glu Tyr Ala Ala Ser
1 5 10 15

Val Lys Gly

<210> SEQ ID NO 25
<211> LENGTH: 19
<212> TYPE: PRT
<213> ORGANISM: Artificial Sequence
<220> FEATURE:
<223> OTHER INFORMATION: Synthetic Construct

<400> SEQUENCE: 25

Leu Ile Arg Asn Lys Ala Val Gly Phe Thr Thr Gln Tyr Ala Ala Ser
1 5 10 15

Val Lys Gly

<210> SEQ ID NO 26
<211> LENGTH: 19
<212> TYPE: PRT
<213> ORGANISM: Artificial Sequence
<220> FEATURE:
<223> OTHER INFORMATION: Synthetic Construct

<400> SEQUENCE: 26

Leu Ile Arg Asn Lys Ala Val Gly His Thr Thr Gln Tyr Ala Ala Ser
1 5 10 15

Val Lys Gly

<210> SEQ ID NO 27
<211> LENGTH: 19
<212> TYPE: PRT
<213> ORGANISM: Artificial Sequence
<220> FEATURE:
<223> OTHER INFORMATION: Synthetic Construct

<400> SEQUENCE: 27

Leu Ile Arg Asn Lys Ala Val Gly Ile Thr Thr Gln Tyr Ala Ala Ser
1 5 10 15

Val Lys Gly

<210> SEQ ID NO 28
<211> LENGTH: 19
<212> TYPE: PRT
<213> ORGANISM: Artificial Sequence
<220> FEATURE:
<223> OTHER INFORMATION: Synthetic Construct

<400> SEQUENCE: 28

Leu Ile Arg Asn Lys Ala Val Gly Gln Thr Thr Gln Tyr Ala Ala Ser
1 5 10 15

Val Lys Gly

<210> SEQ ID NO 29
<211> LENGTH: 19
<212> TYPE: PRT
<213> ORGANISM: Artificial Sequence
<220> FEATURE:
<223> OTHER INFORMATION: Synthetic Construct

<400> SEQUENCE: 29

Leu Ile Arg Asn Lys Ala Val Gly Arg Thr Thr Gln Tyr Ala Ala Ser
1 5 10 15

Val Lys Gly

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct

<400> SEQUENCE: 30

Arg Asp Asn Gly Tyr His
1 5

<210> SEQ ID NO 31
<211> LENGTH: 8
<212> TYPE: PRT
<213> ORGANISM: Artificial Sequence
<220> FEATURE:

<223> OTHER INFORMATION: Synthetic Construct

<400> SEQUENCE: 31

Arg Ala Gly Pro Pro Gly Leu Thr
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

<400> SEQUENCE: 32

Arg Ala Gly Pro Pro Gly Leu Ser
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct

<400> SEQUENCE: 33

Arg Ile Phe Thr Gly Leu His
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Construct

<400> SEQUENCE: 34

Arg Asn Asn Gly Tyr His
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic Construct

<400> SEQUENCE: 35

Arg Leu Gly Pro Pro Gly Leu Ser
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Arg Leu Gly Pro Pro Gly Leu Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Arg Val Gly Pro Pro Gly Leu Thr
1 5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Arg Ala Gly Pro Pro Gly Leu Ala
1 5

<210> SEQ ID NO 39
<211> LENGTH: 16
<212> TYPE: PRT
<213> ORGANISM: Artificial Sequence
<220> FEATURE:
<223> OTHER INFORMATION: Synthetic Construct

<400> SEQUENCE: 39

Arg Ser Ser Gln Arg Leu Leu His Ser Asp Gly Tyr Thr Tyr Leu Asp
1 5 10 15

<210> SEQ ID NO 40
<211> LENGTH: 16
<212> TYPE: PRT
<213> ORGANISM: Artificial Sequence
<220> FEATURE:
<223> OTHER INFORMATION: Synthetic Construct

<400> SEQUENCE: 40

Arg Ser Ser Gln Ser Leu Leu Ala Ser Asp Gly Tyr Thr Tyr Leu Asp
1 5 10 15

<210> SEQ ID NO 41
<211> LENGTH: 16
<212> TYPE: PRT
<213> ORGANISM: Artificial Sequence
<220> FEATURE:
<223> OTHER INFORMATION: Synthetic Construct

<400> SEQUENCE: 41

Arg Ser Ser Gln Arg Leu Leu His Thr Asp Gly Tyr Thr Tyr Leu Asp
1 5 10 15

<210> SEQ ID NO 42
<211> LENGTH: 16
<212> TYPE: PRT
<213> ORGANISM: Artificial Sequence
<220> FEATURE:
<223> OTHER INFORMATION: Synthetic Construct

<400> SEQUENCE: 42

Arg Ser Ser Gln Ser Leu Leu Ala Ser Asp Gly Tyr Asn Tyr Ile Asp
1 5 10 15

<210> SEQ ID NO 43
<211> LENGTH: 16
<212> TYPE: PRT
<213> ORGANISM: Artificial Sequence
<220> FEATURE:
<223> OTHER INFORMATION: Synthetic Construct

<400> SEQUENCE: 43

Arg Ser Ser Gln Ser Leu Leu Ala Ser Asp Gly Tyr Asn Tyr Met Asp
1 5 10 15

<210> SEQ ID NO 44
<211> LENGTH: 16
<212> TYPE: PRT
<213> ORGANISM: Artificial Sequence
<220> FEATURE:
<223> OTHER INFORMATION: Synthetic Construct

<400> SEQUENCE: 44

Arg Ser Ser Gln Ser Leu Leu His Thr Asp Gly Tyr Thr Tyr Leu Asp
1 5 10 15

<210> SEQ ID NO 45
<211> LENGTH: 16
<212> TYPE: PRT
<213> ORGANISM: Artificial Sequence
<220> FEATURE:
<223> OTHER INFORMATION: Synthetic Construct

<400> SEQUENCE: 45

Arg Ser Ser Gln Ser Leu Leu His Ser Asp Gly Tyr Thr Tyr Val Asp
1 5 10 15

<210> SEQ ID NO 46
<211> LENGTH: 16
<212> TYPE: PRT
<213> ORGANISM: Artificial Sequence
<220> FEATURE:
<223> OTHER INFORMATION: Synthetic Construct

<400> SEQUENCE: 46

Arg Ser Ser Gln Ser Leu Leu His Thr Asp Gly Tyr Ile Tyr Leu Asp
1 5 10 15

<210> SEQ ID NO 47
<211> LENGTH: 16
<212> TYPE: PRT
<213> ORGANISM: Artificial Sequence
<220> FEATURE:
<223> OTHER INFORMATION: Synthetic Construct

<400> SEQUENCE: 47

Arg Ser Ser Gln Arg Leu Leu His Ser Asp Gly Tyr Thr Tyr Met Asp
1 5 10 15

<210> SEQ ID NO 48
<211> LENGTH: 16
<212> TYPE: PRT
<213> ORGANISM: Artificial Sequence
<220> FEATURE:
<223> OTHER INFORMATION: Synthetic Construct

<400> SEQUENCE: 48

Arg Ser Ser Gln Ser Leu Leu Ala Thr Asp Gly Tyr Thr Tyr Leu Asp
1 5 10 15

<210> SEQ ID NO 49
<211> LENGTH: 16
<212> TYPE: PRT
<213> ORGANISM: Artificial Sequence
<220> FEATURE:
<223> OTHER INFORMATION: Synthetic Construct

<400> SEQUENCE: 49

Arg Ser Ser Gln Arg Leu Leu Ala Ser Asp Gly Tyr Thr Tyr Val Asp
1 5 10 15

<210> SEQ ID NO 50
<211> LENGTH: 16
<212> TYPE: PRT
<213> ORGANISM: Artificial Sequence
<220> FEATURE:
<223> OTHER INFORMATION: Synthetic Construct

<400> SEQUENCE: 50

Arg Ser Ser Gln Ser Leu Leu Asp Ser Asn Arg Tyr Ala Tyr Val Asp
1 5 10 15

<210> SEQ ID NO 51
<211> LENGTH: 16
<212> TYPE: PRT
<213> ORGANISM: Artificial Sequence
<220> FEATURE:
<223> OTHER INFORMATION: Synthetic Construct

<400> SEQUENCE: 51

Arg Ser Ser Gln Ser Leu Leu His Ser Asp Gly Tyr Thr Tyr Leu Asp
1 5 10 15

<210> SEQ ID NO 52
<211> LENGTH: 16
<212> TYPE: PRT
<213> ORGANISM: Artificial Sequence
<220> FEATURE:
<223> OTHER INFORMATION: Synthetic Construct

<400> SEQUENCE: 52

Arg Ser Ser Gln Asn Leu Leu Ala Thr Asp Gly Tyr Thr Tyr Leu Asp
1 5 10 15

<210> SEQ ID NO 53
<211> LENGTH: 16
<212> TYPE: PRT
<213> ORGANISM: Artificial Sequence
<220> FEATURE:
<223> OTHER INFORMATION: Synthetic Construct

<400> SEQUENCE: 53

Arg Ser Ser Gln Ser Leu Leu Ala Thr Asp Gly Tyr Glu Tyr Leu Asp
1 5 10 15

<210> SEQ ID NO 54
<211> LENGTH: 16
<212> TYPE: PRT
<213> ORGANISM: Artificial Sequence
<220> FEATURE:
<223> OTHER INFORMATION: Synthetic Construct

<400> SEQUENCE: 54

Arg Ser Ser Gln Ser Leu Leu His Ser Asp Gly Tyr Thr Tyr Met Asp
1 5 10 15

<210> SEQ ID NO 55
<211> LENGTH: 16
<212> TYPE: PRT
<213> ORGANISM: Artificial Sequence
<220> FEATURE:
<223> OTHER INFORMATION: Synthetic Construct

<400> SEQUENCE: 55

Arg Ser Ser Gln Ser Leu Leu Ala Ser Asp Gly Tyr Ile Tyr Ile Asp
1 5 10 15

<210> SEQ ID NO 56
<211> LENGTH: 16
<212> TYPE: PRT
<213> ORGANISM: Artificial Sequence
<220> FEATURE:
<223> OTHER INFORMATION: Synthetic Construct

<400> SEQUENCE: 56

Arg Ser Ser Gln Ser Leu Leu Ala Ser Asp Ala Tyr Asn Tyr Ile Asp
1 5 10 15

<210> SEQ ID NO 57
<211> LENGTH: 7
<212> TYPE: PRT
<213> ORGANISM: Artificial Sequence
<220> FEATURE:
<223> OTHER INFORMATION: Synthetic Construct

<400> SEQUENCE: 57

Gly Gly Ser Asn Arg Ala Ser
1 5

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct

<400> SEQUENCE: 58

Gly Gly Ser Lys Arg Ala Ser
1 5

<210> SEQ ID NO 59
<211> LENGTH: 7
<212> TYPE: PRT
<213> ORGANISM: Artificial Sequence
<220> FEATURE:
<223> OTHER INFORMATION: Synthetic Construct

<400> SEQUENCE: 59

Gly Ala Ser Asn Arg Ala Ser
1 5

<210> SEQ ID NO 60
<211> LENGTH: 9
<212> TYPE: PRT
<213> ORGANISM: Artificial Sequence
<220> FEATURE:
<223> OTHER INFORMATION: Synthetic Construct

<400> SEQUENCE: 60

Met Gln His Lys Ala Leu Pro Leu Thr
1 5

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Leu Gln His Arg Ala Leu Pro Pro Thr 1 5

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct

<400> SEQUENCE: 62

Leu Gln His Lys Ala Leu Pro Leu Thr
1 5

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Met Gln His Lys Val Leu Pro Pro Thr
1 5

<210> SEQ ID NO 64
<211> LENGTH: 9
<212> TYPE: PRT
<213> ORGANISM: Artificial Sequence
<220> FEATURE:
<223> OTHER INFORMATION: Synthetic Construct

<400> SEQUENCE: 64

Met Gln His Lys Ala Leu Pro Pro Thr
1 5

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Leu Gln His Lys Ala Leu Pro Pro Thr
1 5

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Met Gln His Lys Val Leu Pro Leu Thr
1 5

<210> SEQ ID NO 67
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Asn
<220> FEATURE:

<221> NAME/KEY: VARIANT
<222> LOCATION: 4
<223> OTHER INFORMATION: Xaa = Met or Ile

<400> SEQUENCE: 67

Xaa Tyr Tyr Xaa Gln
1               5

<210> SEQ ID NO 68
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Lys or Asn
<220> FEATURE:
<221> NAME/KEY: VARIANT
<222> LOCATION: 6
<223> OTHER INFORMATION: Xaa = Ala or Val
<220> FEATURE:
<221> NAME/KEY: VARIANT
<222> LOCATION: 7
<223> OTHER INFORMATION: Xaa = Val, Asn, or Ile
<220> FEATURE:
<221> NAME/KEY: VARIANT
<222> LOCATION: 9
<223> OTHER INFORMATION: Xaa = Gly, Glu, Phe, His, Ile, Gln, or Arg
<220> FEATURE:
<221> NAME/KEY: VARIANT
<222> LOCATION: 11
<223> OTHER INFORMATION: Xaa = Thr, Val, or Ala
<220> FEATURE:
<221> NAME/KEY: VARIANT
<222> LOCATION: 12
<223> OTHER INFORMATION: Xaa = Gln, Glu, Thr, or Ser
<220> FEATURE:
<221> NAME/KEY: VARIANT
<222> LOCATION: 13
<223> OTHER INFORMATION: Xaa = Tyr or Phe
<220> FEATURE:
<221> NAME/KEY: VARIANT
<222> LOCATION: 17
<223> OTHER INFORMATION: Xaa = Val or Leu

<400> SEQUENCE: 68

Leu Ile Arg Xaa Lys Xaa Xaa Gly Xaa Thr Xaa Xaa Xaa Ala Ala Ser
1               5                   10                  15

Xaa Lys Gly

<210> SEQ ID NO 69
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ala, Leu, or Val
<220> FEATURE:
<221> NAME/KEY: VARIANT
<222> LOCATION: 8
<223> OTHER INFORMATION: Xaa = Thr, Ser, or Ala

<400> SEQUENCE: 69

Arg Xaa Gly Pro Pro Gly Leu Xaa
1               5

<210> SEQ ID NO 70

<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser, Arg, or Asn
<220> FEATURE:
<221> NAME/KEY: VARIANT
<222> LOCATION: 8
<223> OTHER INFORMATION: Xaa = Ala, His, or Asp
<220> FEATURE:
<221> NAME/KEY: VARIANT
<222> LOCATION: 9
<223> OTHER INFORMATION: Xaa = Ser or Thr
<220> FEATURE:
<221> NAME/KEY: VARIANT
<222> LOCATION: 10
<223> OTHER INFORMATION: Xaa = Asp or Asn
<220> FEATURE:
<221> NAME/KEY: VARIANT
<222> LOCATION: 11
<223> OTHER INFORMATION: Xaa = Gly, Ala, or Arg
<220> FEATURE:
<221> NAME/KEY: VARIANT
<222> LOCATION: 13
<223> OTHER INFORMATION: Xaa = Asn, Ile, Thr, Glu, or Ala
<220> FEATURE:
<221> NAME/KEY: VARIANT
<222> LOCATION: 15
<223> OTHER INFORMATION: Xaa = Ile, Met, Leu, or Val

<400> SEQUENCE: 70

```
Arg Ser Ser Gln Xaa Leu Leu Xaa Xaa Xaa Xaa Tyr Xaa Tyr Xaa Asp
1               5                   10                  15
```

<210> SEQ ID NO 71
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Gly or Ala
<220> FEATURE:
<221> NAME/KEY: VARIANT
<222> LOCATION: 4
<223> OTHER INFORMATION: Xaa = Asn or Lys

<400> SEQUENCE: 71

```
Gly Xaa Ser Xaa Arg Ala Ser
1               5
```

<210> SEQ ID NO 72
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Leu or Met
<220> FEATURE:
<221> NAME/KEY: VARIANT
<222> LOCATION: 4
<223> OTHER INFORMATION: Xaa = Arg or Lys
<220> FEATURE:
<221> NAME/KEY: VARIANT
<222> LOCATION: 5
<223> OTHER INFORMATION: Xaa = Ala or Val
<220> FEATURE:
<221> NAME/KEY: VARIANT
<222> LOCATION: 8
<223> OTHER INFORMATION: Xaa = Pro or Leu

<400> SEQUENCE: 72

```
Xaa Gln His Xaa Xaa Leu Pro Xaa Thr
1               5
```

<210> SEQ ID NO 73
<211> LENGTH: 117
<212> TYPE: PRT
<213> ORGANISM: Artificial Sequence
<220> FEATURE:
<223> OTHER INFORMATION: Synthetic Construct

<400> SEQUENCE: 73

```
Glu Val Gln Leu Val Glu Ser Gly Gly Gly Met Val Gln Pro Gly Gly
1               5                   10                  15

Ser Leu Arg Val Ser Cys Ala Ala Ser Gly Phe Thr Phe Thr Lys Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Asn Gly Gly Thr Ala Glu Tyr Val Ala
    50                  55                  60

Ser Val Lys Asp Arg Phe Thr Ile Ser Arg Asp Asp Ser Lys Ser Ile
65                  70                  75                  80

Ala Tyr Leu Gln Met Ser Ser Leu Lys Thr Glu Asp Thr Ala Val Tyr
                85                  90                  95

Tyr Cys Val Met Arg Asp Asn Gly Tyr His Trp Gly Gln Gly Val Leu
            100                 105                 110

Val Thr Val Ser Ser
        115
```

<210> SEQ ID NO 74
<211> LENGTH: 119
<212> TYPE: PRT
<213> ORGANISM: Artificial Sequence
<220> FEATURE:
<223> OTHER INFORMATION: Synthetic Construct

<400> SEQUENCE: 74

```
Glu Val Gln Leu Val Glu Ser Gly Gly Gly Leu Val Gln Pro Gly Gly
1               5                   10                  15

Ser Leu Lys Val Ser Cys Ala Ala Ser Gly Phe Ile Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Lys Lys Val Asn Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Ser Ser Leu Lys Ile Glu Asp Thr Ala Val Tyr
                85                  90                  95

Tyr Cys Val Ser Arg Ala Gly Pro Pro Gly Leu Thr Trp Gly Gln Gly
            100                 105                 110

Val Leu Val Thr Ile Ser Ser
        115
```

<210> SEQ ID NO 75
<211> LENGTH: 119
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Val Gln Pro Gly Gly
1 5 10 15

Ser Leu Lys Val Ser Cys Ala Ala Ser Gly Phe Ile Phe Ser Asp Tyr
20 25 30

Tyr Met Gln Trp Val Arg Gln Ala Pro Gly Lys Gly Pro Glu Trp Val
35 40 45

Gly Leu Ile Arg Lys Lys Val Asn Gly Gly Thr Thr Glu Tyr Ala Ala
50 55 60

Ser Val Lys Gly Arg Phe Thr Ile Ser Arg Asp Asp Ser Lys Ser Ile
65 70 75 80

Val Tyr Leu Gln Met Ser Ser Leu Lys Ile Glu Asp Thr Ala Val Tyr
85 90 95

Tyr Cys Val Ser Arg Ala Gly Pro Pro Gly Leu Thr Trp Gly Gln Gly
100 105 110

Val Leu Val Thr Val Ser Ser
115

<210> SEQ ID NO 76
<211> LENGTH: 119
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Gln Ser Gly Gly Gly Leu Val Gln Pro Gly Gly
1 5 10 15

Ser Leu Lys Val Ser Cys Ala Ala Ser Gly Phe Thr Phe Ser Asp Tyr
20 25 30

Tyr Met Gln Trp Val Arg Gln Ala Pro Gly Lys Gly Pro Glu Trp Val
35 40 45

Gly Leu Ile Arg Asn Lys Ala Ile Gly Gly Thr Thr Gln Tyr Ala Ala
50 55 60

Ser Val Lys Gly Arg Phe Thr Ile Ser Arg Asp Asp Ser Lys Ser Ile
65 70 75 80

Val Tyr Leu Gln Met Ser Ser Leu Lys Thr Glu Asp Thr Ala Val Tyr
85 90 95

Tyr Cys Val Ser Arg Ala Gly Pro Pro Gly Leu Ser Trp Gly Gln Gly
100 105 110

Val Val Val Thr Val Ser Ser
115

<210> SEQ ID NO 77
<211> LENGTH: 119
<212> TYPE: PRT
<213> ORGANISM: Artificial Sequence
<220> FEATURE:
<223> OTHER INFORMATION: Synthetic Construct

<400> SEQUENCE: 77

Asp Met Gln Leu Val Glu Ser Gly Gly Gly Leu Val Gln Pro Gly Gly
1 5 10 15

```
Ser Leu Lys Val Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Val Gly Gly Thr Thr Gln Tyr Ala Ala
    50                  55                  60

Ser Val Lys Gly Arg Phe Thr Ile Ser Arg Asp Asp Ser Lys Ser Ile
65                  70                  75                  80

Val Tyr Leu Glu Met Ser Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110

Val Leu Val Thr Val Ser Ser
        115


<210> SEQ ID NO 78
<211> LENGTH: 119
<212> TYPE: PRT
<213> ORGANISM: Artificial Sequence
<220> FEATURE:
<223> OTHER INFORMATION: Synthetic Construct

<400> SEQUENCE: 78

Glu Val His Leu Val Glu Ser Gly Gly Gly Leu Val Gln Pro Gly Gly
1               5                   10                  15

Ser Leu Lys Val Ser Cys Ala Ala Ser Gly Phe Ile Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Lys Lys Val Asn Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Lys Ile Glu Asp Thr Ala Val Tyr
                85                  90                  95

Tyr Cys Val Ser Arg Ala Gly Pro Pro Gly Leu Thr Trp Gly Gln Gly
            100                 105                 110

Val Leu Val Thr Ile Ser Ser
        115


<210> SEQ ID NO 79
<211> LENGTH: 119
<212> TYPE: PRT
<213> ORGANISM: Artificial Sequence
<220> FEATURE:
<223> OTHER INFORMATION: Synthetic Construct

<400> SEQUENCE: 79

Asp Val Gln Leu Val Glu Ser Gly Gly Gly Leu Val Gln Pro Gly Gly
1               5                   10                  15

Ser Leu Lys Val Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Ile Gly Glu Thr Thr Glu Tyr Ala Ala
    50                  55                  60

Ser Val Lys Gly Arg Phe Thr Ile Ser Arg Asp Asp Ser Lys Ser Ile
```

```
65                  70                  75                  80

Val Tyr Leu Gln Met Ser Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110

Val Leu Val Thr Ile Ser Ser
        115


<210> SEQ ID NO 80
<211> LENGTH: 118
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Val Glu Ser Gly Gly Gly Leu Ile Gln Pro Gly Gly
1               5                   10                  15

Ser Leu Arg Val Ser Cys Ala Ala Ser Gly Phe Thr Phe Ser Asp Tyr
            20                  25                  30

Tyr Leu Gln Trp Val Arg Gln Ala Pro Gly Lys Gly Pro Glu Trp Val
        35                  40                  45

Gly Leu Ile Arg Thr Lys Arg Tyr Gly Gly Thr Ser Glu Tyr Ala Ala
    50                  55                  60

Ser Val Lys Gly Arg Tyr Thr Ile Ser Arg Asp Asp Ser Lys Ala Ile
65                  70                  75                  80

Ala Tyr Leu Gln Met Ser Ser Leu Lys Thr Glu Asp Thr Ala Val Tyr
                85                  90                  95

Tyr Cys Val Val Arg Ile Phe Thr Gly Leu His Trp Gly Lys Gly Thr
            100                 105                 110

Pro Val Thr Val Ser Ser
        115


<210> SEQ ID NO 81
<211> LENGTH: 119
<212> TYPE: PRT
<213> ORGANISM: Artificial Sequence
<220> FEATURE:
<223> OTHER INFORMATION: Synthetic Construct

<400> SEQUENCE: 81

Glu Val Gln Leu Val Glu Ser Gly Gly Gly Leu Val Gln Pro Gly Gly
1               5                   10                  15

Ser Leu Lys Val Ser Cys Ala Ala Ser Gly Phe Ile Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Lys Lys Val Asn Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Ser Ser Leu Lys Ile Glu Asp Thr Ala Val Tyr
                85                  90                  95

Tyr Cys Val Ser Arg Ala Gly Pro Pro Gly Leu Thr Trp Gly Gln Gly
            100                 105                 110

Val Leu Val Thr Ile Ser Ser
        115
```

<210> SEQ ID NO 82
<211> LENGTH: 119
<212> TYPE: PRT
<213> ORGANISM: Artificial Sequence
<220> FEATURE:
<223> OTHER INFORMATION: Synthetic Construct

<400> SEQUENCE: 82

```
Gln Val Gln Leu Val Glu Ser Gly Gly Gly Leu Val Gln Pro Gly Gly
1               5                   10                  15

Ser Leu Lys Val Ser Cys Ala Ala Ser Gly Phe Ile Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Lys Lys Val Asn Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Lys Ile Glu Asp Thr Ala Val Tyr
                85                  90                  95

Tyr Cys Val Ser Arg Ala Gly Pro Pro Gly Leu Thr Trp Gly Gln Gly
            100                 105                 110

Val Leu Ile Thr Val Ser Ser
        115
```

<210> SEQ ID NO 83
<211> LENGTH: 117
<212> TYPE: PRT
<213> ORGANISM: Artificial Sequence
<220> FEATURE:
<223> OTHER INFORMATION: Synthetic Construct

<400> SEQUENCE: 83

```
Glu Val Gln Leu Val Glu Ser Gly Gly Gly Leu Val Gln Pro Gly Gly
1               5                   10                  15

Ser Leu Arg Val Ser Cys Ala Ala Ser Gly Phe Arg Phe Ser Asp Phe
            20                  25                  30

Tyr Met Gln Trp Val Arg Gln Ala Pro Gly Lys Arg Pro Glu Trp Val
        35                  40                  45

Gly Leu Ile Arg Asn Lys Pro Tyr Gly Gly Thr Ala Glu Tyr Ala Ala
    50                  55                  60

Ser Val Lys Gly Arg Phe Thr Ile Ser Arg Asp Asp Ser Lys Ser Val
65                  70                  75                  80

Thr Asp Leu Gln Met Ser Ser Leu Lys Thr Glu Asp Thr Ala Ile Tyr
                85                  90                  95

Tyr Cys Val Met Arg Asn Asn Gly Tyr His Trp Gly Gln Gly Val Leu
            100                 105                 110

Val Thr Ile Ser Ser
        115
```

<210> SEQ ID NO 84
<211> LENGTH: 119
<212> TYPE: PRT
<213> ORGANISM: Artificial Sequence
<220> FEATURE:
<223> OTHER INFORMATION: Synthetic Construct

<400> SEQUENCE: 84

```
Val Val Gln Leu Val Glu Ser Gly Gly Gly Leu Val Gln Pro Gly Gly
```

```
1               5                   10                  15

Ser Leu Lys Val Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Ile Gly Glu Thr Thr Gln Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110

Val Leu Val Thr Ile Ser Ser
        115


<210> SEQ ID NO 85
<211> LENGTH: 119
<212> TYPE: PRT
<213> ORGANISM: Artificial Sequence
<220> FEATURE:
<223> OTHER INFORMATION: Synthetic Construct

<400> SEQUENCE: 85

Val Val Gln Leu Val Glu Ser Gly Gly Gly Leu Val Gln Pro Gly Gly
1               5                   10                  15

Ser Leu Lys Val Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Ile Gly Gly Thr Thr Gln Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110

Val Leu Val Thr Ile Ser Ser
        115


<210> SEQ ID NO 86
<211> LENGTH: 119
<212> TYPE: PRT
<213> ORGANISM: Artificial Sequence
<220> FEATURE:
<223> OTHER INFORMATION: Synthetic Construct

<400> SEQUENCE: 86

Val Val Gln Leu Val Glu Ser Gly Gly Gly Leu Val Gln Pro Gly Gly
1               5                   10                  15

Ser Leu Lys Val Ser Cys Ala Thr Ser Gly Phe Thr Phe Ser Asp Tyr
            20                  25                  30

Tyr Met Gln Trp Val Arg Gln Ala Pro Gly Lys Gly Pro Glu Trp Leu
        35                  40                  45

Gly Leu Ile Arg Asn Lys Ala Ile Gly Gly Thr Thr Gln Tyr Ala Ala
    50                  55                  60
```

```
Ser Val Lys Gly Arg Phe Thr Ile Ser Arg Asp Asp Ser Lys Gly Ile
65                  70                  75                  80

Ala Tyr Leu Gln Met Ser Ser Leu Lys Thr Glu Asp Thr Ala Val Tyr
                85                  90                  95

Tyr Cys Val Cys Arg Ala Gly Pro Pro Gly Leu Ser Trp Gly Gln Gly
            100                 105                 110

Val Leu Val Thr Val Ser Ser
        115


<210> SEQ ID NO 87
<211> LENGTH: 119
<212> TYPE: PRT
<213> ORGANISM: Artificial Sequence
<220> FEATURE:
<223> OTHER INFORMATION: Synthetic Construct

<400> SEQUENCE: 87

Val Val Gln Leu Val Glu Ser Gly Gly Gly Leu Val Gln Pro Gly Gly
1               5                   10                  15

Ser Leu Lys Val Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Ile Gly Glu Thr Thr Glu Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Lys Pro Glu Asp Thr Ala Val Tyr
                85                  90                  95

Tyr Cys Ala Gly Arg Leu Gly Pro Pro Gly Leu Ser Trp Gly Gln Gly
            100                 105                 110

Val Leu Val Thr Val Ser Ser
        115


<210> SEQ ID NO 88
<211> LENGTH: 119
<212> TYPE: PRT
<213> ORGANISM: Artificial Sequence
<220> FEATURE:
<223> OTHER INFORMATION: Synthetic Construct

<400> SEQUENCE: 88

Glu Val His Leu Val Glu Ser Gly Gly Gly Leu Val Gln Pro Gly Gly
1               5                   10                  15

Ser Leu Lys Val Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Ile Gly Glu Thr Thr Glu Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Lys Pro Glu Asp Thr Ala Val Tyr
                85                  90                  95

Tyr Cys Ala Gly Arg Leu Gly Pro Pro Gly Leu Ser Trp Gly Gln Gly
            100                 105                 110

Val Leu Val Thr Val Ser Ser
        115
```

<210> SEQ ID NO 89
<211> LENGTH: 119
<212> TYPE: PRT
<213> ORGANISM: Artificial Sequence
<220> FEATURE:
<223> OTHER INFORMATION: Synthetic Construct

<400> SEQUENCE: 89

```
Val Val Gln Leu Val Glu Ser Gly Gly Gly Leu Val Leu Pro Gly Gly
1               5                   10                  15

Ser Leu Lys Val Ser Cys Ala Ala Ser Gly Phe Ile Phe Ser Asp Tyr
            20                  25                  30

Tyr Ile Gln Trp Val Arg Gln Ala Pro Gly Lys Gly Pro Glu Trp Val
        35                  40                  45

Gly Leu Ile Arg Asn Lys Ala Val Gly Glu Thr Val Gln Tyr Ala Ala
    50                  55                  60

Ser Leu Lys Gly Arg Phe Thr Ile Ser Arg Asp Asp Ser Lys Ser Ile
65                  70                  75                  80

Ala Tyr Leu Gln Met Thr Ser Leu Lys Thr Glu Asp Thr Ala Met Tyr
                85                  90                  95

Tyr Cys Val Ser Arg Ala Gly Pro Pro Gly Leu Thr Trp Gly Gln Gly
            100                 105                 110

Val Leu Val Thr Val Ser Ser
        115
```

<210> SEQ ID NO 90
<211> LENGTH: 119
<212> TYPE: PRT
<213> ORGANISM: Artificial Sequence
<220> FEATURE:
<223> OTHER INFORMATION: Synthetic Construct

<400> SEQUENCE: 90

```
Val Val Gln Leu Val Glu Ser Gly Gly Gly Leu Val Gln Pro Gly Gly
1               5                   10                  15

Ser Leu Lys Val Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Ile Gly Glu Thr Thr Gln Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110

Val Leu Val Thr Val Ser Ser
        115
```

<210> SEQ ID NO 91
<211> LENGTH: 119
<212> TYPE: PRT
<213> ORGANISM: Artificial Sequence
<220> FEATURE:
<223> OTHER INFORMATION: Synthetic Construct

<400> SEQUENCE: 91

```
Glu Val Gln Leu Val Glu Ser Gly Gly Gly Leu Val Gln Pro Gly Gly
1               5                   10                  15

Ser Leu Lys Val Ser Cys Val Ala Ser Gly Phe Thr Phe Ser Asp Tyr
            20                  25                  30

Tyr Ile Gln Trp Val Arg Gln Ala Pro Gly Lys Gly Pro Glu Trp Val
        35                  40                  45

Gly Leu Ile Arg Asn Lys Ala Val Gly Gly Thr Thr Ser Tyr Ala Ala
    50                  55                  60

Ser Val Lys Gly Arg Phe Thr Ile Ser Arg Asp Asp Ser Lys Ser Val
65                  70                  75                  80

Ala Tyr Leu Gln Met Thr Ser Leu Lys Thr Glu Asp Thr Ala Val Tyr
                85                  90                  95

Phe Cys Val Ser Arg Ala Gly Pro Pro Gly Leu Ser Trp Gly Gln Gly
            100                 105                 110

Val Leu Val Thr Val Ser Ser
        115


<210> SEQ ID NO 92
<211> LENGTH: 119
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Glu Ser Gly Gly Gly Leu Val Gln Pro Gly Gly
1               5                   10                  15

Ser Leu Lys Val Ser Cys Ala Ala Ser Gly Phe Thr Phe Arg Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Ile Gly Glu Thr Ala Glu Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Lys Thr Glu Asp Thr Ala Val Tyr
                85                  90                  95

Tyr Cys Thr Ser Arg Ala Gly Pro Pro Gly Leu Ser Trp Gly Gln Gly
            100                 105                 110

Val Leu Val Thr Val Ser Ser
        115


<210> SEQ ID NO 93
<211> LENGTH: 119
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Gln Ser Gly Gly Gly Leu Val Gln Pro Gly Gly
1               5                   10                  15

Ser Leu Lys Val Ser Cys Ala Ala Ser Gly Phe Ile Phe Ser Asn Tyr
            20                  25                  30

Tyr Ile Gln Trp Val Arg Gln Ala Pro Gly Lys Gly Pro Glu Trp Val
        35                  40                  45

Gly Leu Ile Arg Asn Lys Ala Ile Gly Glu Thr Thr Glu Phe Ala Ala
    50                  55                  60
```

```
Ser Val Lys Gly Arg Phe Thr Ile Ser Arg Asp Asp Ser Lys Ser Ile
65                  70                  75                  80

Val Tyr Leu Gln Met Thr Arg Leu Lys Thr Glu Asp Thr Ala Val Tyr
                85                  90                  95

Tyr Cys Ala Gly Arg Leu Gly Pro Pro Gly Leu Thr Trp Gly Gln Gly
            100                 105                 110

Val Leu Val Thr Ile Ser Ser
        115


<210> SEQ ID NO 94
<211> LENGTH: 119
<212> TYPE: PRT
<213> ORGANISM: Artificial Sequence
<220> FEATURE:
<223> OTHER INFORMATION: Synthetic Construct

<400> SEQUENCE: 94

Val Val Gln Leu Val Glu Ser Gly Gly Gly Leu Val Gln Pro Gly Gly
1               5                   10                  15

Ser Leu Lys Val Ser Cys Thr Ala Ser Gly Phe Ile Phe Asn Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Asn Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Lys Thr Glu Asp Thr Ala Val Tyr
                85                  90                  95

Phe Cys Thr Gly Arg Leu Gly Pro Pro Gly Leu Thr Trp Gly Gln Gly
            100                 105                 110

Val Leu Val Thr Ile Ser Ser
        115


<210> SEQ ID NO 95
<211> LENGTH: 119
<212> TYPE: PRT
<213> ORGANISM: Artificial Sequence
<220> FEATURE:
<223> OTHER INFORMATION: Synthetic Construct

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Ile Gln Trp Val Arg Gln Ala Pro Gly Lys Gly Pro Glu Trp Val
        35                  40                  45

Gly Leu Ile Arg Asn Lys Ala Ile Gly Gly Thr Val Glu Tyr Ala Ala
    50                  55                  60

Ser Val Lys Gly Arg Phe Thr Ile Ser Arg Asp Asp Ser Lys Arg Ile
65                  70                  75                  80

Ala Tyr Leu Gln Met Arg Ser Leu Lys Thr Glu Asp Thr Ala Val Tyr
                85                  90                  95

Phe Cys Thr Gly Arg Val Gly Pro Pro Gly Leu Thr Trp Gly Gln Gly
            100                 105                 110

Val Leu Val Thr Ile Ser Ser
```

115

<210> SEQ ID NO 96
<211> LENGTH: 119
<212> TYPE: PRT
<213> ORGANISM: Artificial Sequence
<220> FEATURE:
<223> OTHER INFORMATION: Synthetic Construct

<400> SEQUENCE: 96

Val Val Gln Leu Val Glu Ser Gly Gly Gly Leu Val Gln Pro Gly Gly
1 5 10 15

Ser Leu Lys Val Ser Cys Ala Ala Ser Gly Phe Ile Phe Ser Asp Tyr
20 25 30

Tyr Met Gln Trp Val Arg Gln Ala Pro Gly Lys Gly Pro Glu Trp Val
35 40 45

Gly Leu Ile Arg Lys Lys Val Asn Gly Gly Thr Thr Glu Tyr Ala Ala
50 55 60

Ser Val Lys Gly Arg Phe Thr Ile Ser Arg Asp Asp Ser Lys Ser Ile
65 70 75 80

Val Tyr Leu Gln Met Ser Ser Leu Lys Ile Glu Asp Thr Ala Val Tyr
85 90 95

Tyr Cys Val Ser Arg Ala Gly Pro Pro Gly Leu Ala Trp Gly Gln Gly
100 105 110

Val Leu Val Thr Ile Ser Ser
115

<210> SEQ ID NO 97
<211> LENGTH: 119
<212> TYPE: PRT
<213> ORGANISM: Artificial Sequence
<220> FEATURE:
<223> OTHER INFORMATION: Synthetic Construct

<400> SEQUENCE: 97

Glu Val Gln Leu Val Glu Ser Gly Gly Gly Phe Val Gln Pro Gly Gly
1 5 10 15

Ser Leu Lys Val Ser Cys Val Ala Ser Gly Phe Thr Phe Ser Asp Tyr
20 25 30

Tyr Ile Gln Trp Val Arg Gln Ala Pro Gly Lys Gly Pro Glu Trp Val
35 40 45

Gly Leu Ile Arg Asn Lys Ala Val Gly Gly Thr Thr Thr Tyr Ala Ala
50 55 60

Ser Val Lys Gly Arg Phe Thr Ile Ser Arg Asp Asp Ser Lys Ser Val
65 70 75 80

Ala Tyr Leu Gln Met Thr Ser Leu Lys Thr Glu Asp Thr Ala Val Tyr
85 90 95

Phe Cys Val Ser Arg Ala Gly Pro Pro Gly Leu Ser Trp Gly Gln Gly
100 105 110

Val Leu Val Thr Ile Ser Ser
115

<210> SEQ ID NO 98
<211> LENGTH: 119
<212> TYPE: PRT
<213> ORGANISM: Artificial Sequence
<220> FEATURE:
<223> OTHER INFORMATION: Synthetic Construct

<400> SEQUENCE: 98

```
Glu Val Gln Leu Val Glu Ser Gly Gly Gly Leu Val Leu Pro Gly Gly
1               5                   10                  15

Ser Leu Lys Val Ser Cys Ala Ala Ser Gly Phe Ile Phe Ser Asp Tyr
            20                  25                  30

Tyr Ile Gln Trp Val Arg Gln Ala Pro Gly Lys Gly Pro Glu Trp Val
        35                  40                  45

Gly Leu Ile Arg Asn Lys Ala Val Gly Glu Thr Val Gln Tyr Ala Ala
    50                  55                  60

Ser Leu Lys Gly Arg Phe Thr Ile Ser Arg Asp Asp Ser Lys Ser Ile
65                  70                  75                  80

Ala Tyr Leu Gln Met Thr Ser Leu Lys Thr Glu Asp Thr Ala Met Tyr
                85                  90                  95

Tyr Cys Val Ser Arg Ala Gly Pro Pro Gly Leu Thr Trp Gly Gln Gly
            100                 105                 110

Val Leu Val Thr Ile Ser Ser
        115
```

<210> SEQ ID NO 99
<211> LENGTH: 119
<212> TYPE: PRT
<213> ORGANISM: Artificial Sequence
<220> FEATURE:
<223> OTHER INFORMATION: Synthetic Construct

<400> SEQUENCE: 99

```
Glu Val Gln Leu Val Gln Ser Gly Gly Gly Leu Val Gln Pro Gly Gly
1               5                   10                  15

Ser Leu Lys Val Ser Cys Ala Ala Ser Gly Phe Thr Phe Arg Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Ile Gly Gly Thr Thr Gln Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Ser Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110

Val Leu Val Thr Val Ser Ser
        115
```

<210> SEQ ID NO 100
<211> LENGTH: 119
<212> TYPE: PRT
<213> ORGANISM: Artificial Sequence
<220> FEATURE:
<223> OTHER INFORMATION: Synthetic Construct

<400> SEQUENCE: 100

```
Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Val Gly Gly Thr Thr Gln Tyr Ala Ala
```

```
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110

Val Leu Val Thr Val Ser Ser
        115


<210> SEQ ID NO 101
<211> LENGTH: 119
<212> TYPE: PRT
<213> ORGANISM: Artificial Sequence
<220> FEATURE:
<223> OTHER INFORMATION: Synthetic Construct

<400> SEQUENCE: 101

Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Val Gly Gly Thr Thr Glu Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110

Val Leu Val Thr Val Ser Ser
        115


<210> SEQ ID NO 102
<211> LENGTH: 119
<212> TYPE: PRT
<213> ORGANISM: Artificial Sequence
<220> FEATURE:
<223> OTHER INFORMATION: Synthetic Construct

<400> SEQUENCE: 102

Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Val Gly Glu Thr Thr Gln Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110
```

Val Leu Val Thr Val Ser Ser
115

<210> SEQ ID NO 103
<211> LENGTH: 119
<212> TYPE: PRT
<213> ORGANISM: Artificial Sequence
<220> FEATURE:
<223> OTHER INFORMATION: Synthetic Construct

<400> SEQUENCE: 103

Glu Met Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Tyr Met Gln Trp Val Arg Gln Ala Pro Gly Lys Gly Pro Glu Trp Val
35 40 45

Gly Leu Ile Arg Asn Lys Ala Val Gly Glu Thr Thr Glu Tyr Ala Ala
50 55 60

Ser Val Lys Gly Arg Phe Thr Ile Ser Arg Asp Asp Ser Lys Asn Ser
65 70 75 80

Val Tyr Leu Gln Met Asn Ser Leu Lys Thr Glu Asp Thr Ala Val Tyr
85 90 95

Tyr Cys Val Ser Arg Ala Gly Pro Pro Gly Leu Ser Trp Gly Gln Gly
100 105 110

Val Leu Val Thr Val Ser Ser
115

<210> SEQ ID NO 104
<211> LENGTH: 119
<212> TYPE: PRT
<213> ORGANISM: Artificial Sequence
<220> FEATURE:
<223> OTHER INFORMATION: Synthetic Construct

<400> SEQUENCE: 104

Glu Met Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Tyr Met Gln Trp Val Arg Gln Ala Pro Gly Lys Gly Pro Glu Trp Val
35 40 45

Gly Leu Ile Arg Asn Lys Ala Val Gly Phe Thr Thr Gln Tyr Ala Ala
50 55 60

Ser Val Lys Gly Arg Phe Thr Ile Ser Arg Asp Asp Ser Lys Asn Ser
65 70 75 80

Val Tyr Leu Gln Met Asn Ser Leu Lys Thr Glu Asp Thr Ala Val Tyr
85 90 95

Tyr Cys Val Ser Arg Ala Gly Pro Pro Gly Leu Ser Trp Gly Gln Gly
100 105 110

Val Leu Val Thr Val Ser Ser
115

<210> SEQ ID NO 105
<211> LENGTH: 119
<212> TYPE: PRT
<213> ORGANISM: Artificial Sequence
<220> FEATURE:
<223> OTHER INFORMATION: Synthetic Construct

<400> SEQUENCE: 105

Glu Met Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Tyr Met Gln Trp Val Arg Gln Ala Pro Gly Lys Gly Pro Glu Trp Val
35 40 45

Gly Leu Ile Arg Asn Lys Ala Val Gly His Thr Thr Gln Tyr Ala Ala
50 55 60

Ser Val Lys Gly Arg Phe Thr Ile Ser Arg Asp Asp Ser Lys Asn Ser
65 70 75 80

Val Tyr Leu Gln Met Asn Ser Leu Lys Thr Glu Asp Thr Ala Val Tyr
85 90 95

Tyr Cys Val Ser Arg Ala Gly Pro Pro Gly Leu Ser Trp Gly Gln Gly
100 105 110

Val Leu Val Thr Val Ser Ser
115

<210> SEQ ID NO 106
<211> LENGTH: 119
<212> TYPE: PRT
<213> ORGANISM: Artificial Sequence
<220> FEATURE:
<223> OTHER INFORMATION: Synthetic Construct

<400> SEQUENCE: 106

Glu Met Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Tyr Met Gln Trp Val Arg Gln Ala Pro Gly Lys Gly Pro Glu Trp Val
35 40 45

Gly Leu Ile Arg Asn Lys Ala Val Gly Ile Thr Thr Gln Tyr Ala Ala
50 55 60

Ser Val Lys Gly Arg Phe Thr Ile Ser Arg Asp Asp Ser Lys Asn Ser
65 70 75 80

Val Tyr Leu Gln Met Asn Ser Leu Lys Thr Glu Asp Thr Ala Val Tyr
85 90 95

Tyr Cys Val Ser Arg Ala Gly Pro Pro Gly Leu Ser Trp Gly Gln Gly
100 105 110

Val Leu Val Thr Val Ser Ser
115

<210> SEQ ID NO 107
<211> LENGTH: 119
<212> TYPE: PRT
<213> ORGANISM: Artificial Sequence
<220> FEATURE:
<223> OTHER INFORMATION: Synthetic Construct

<400> SEQUENCE: 107

Glu Met Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Tyr Met Gln Trp Val Arg Gln Ala Pro Gly Lys Gly Pro Glu Trp Val
35 40 45

```
Gly Leu Ile Arg Asn Lys Ala Val Gly Gln Thr Thr Gln Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110

Val Leu Val Thr Val Ser Ser
        115


<210> SEQ ID NO 108
<211> LENGTH: 119
<212> TYPE: PRT
<213> ORGANISM: Artificial Sequence
<220> FEATURE:
<223> OTHER INFORMATION: Synthetic Construct

<400> SEQUENCE: 108

Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Val Gly Arg Thr Thr Gln Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110

Val Leu Val Thr Val Ser Ser
        115


<210> SEQ ID NO 109
<211> LENGTH: 119
<212> TYPE: PRT
<213> ORGANISM: Artificial Sequence
<220> FEATURE:
<223> OTHER INFORMATION: Synthetic Construct

<400> SEQUENCE: 109

Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Gln Trp Val Arg Gln Ala Pro Gly Lys Gly Pro Glu Trp Val
        35                  40                  45

Gly Leu Ile Arg Asn Lys Ala Val Gly Glu Thr Thr Gln Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Val Ser Arg Ala Gly Pro Pro Gly Leu Ser Trp Gly Gln Gly
            100                 105                 110
```

```
Val Leu Val Thr Val Ser Ser
        115


<210> SEQ ID NO 110
<211> LENGTH: 119
<212> TYPE: PRT
<213> ORGANISM: Artificial Sequence
<220> FEATURE:
<223> OTHER INFORMATION: Synthetic Construct

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Ile Gln Trp Val Arg Gln Ala Pro Gly Lys Gly Pro Glu Trp Val
        35                  40                  45

Gly Leu Ile Arg Asn Lys Ala Ile Gly Glu Thr Thr Glu Phe Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Ala Gly Arg Leu Gly Pro Pro Gly Leu Thr Trp Gly Gln Gly
            100                 105                 110

Val Leu Val Thr Val Ser Ser
        115


<210> SEQ ID NO 111
<211> LENGTH: 119
<212> TYPE: PRT
<213> ORGANISM: Artificial Sequence
<220> FEATURE:
<223> OTHER INFORMATION: Synthetic Construct

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Ile Gln Trp Val Arg Gln Ala Pro Gly Lys Gly Pro Glu Trp Val
        35                  40                  45

Gly Leu Ile Arg Asn Lys Ala Val Gly Gly Thr Thr Thr Tyr Ala Ala
    50                  55                  60

Ser Val Lys Gly Arg Phe Thr Ile Ser Arg Asp Asp Ser Lys Asn Ser
65                  70                  75                  80

Ala Tyr Leu Gln Met Asn Ser Leu Lys Thr Glu Asp Thr Ala Val Tyr
                85                  90                  95

Phe Cys Val Ser Arg Ala Gly Pro Pro Gly Leu Ser Trp Gly Gln Gly
            100                 105                 110

Val Leu Val Thr Val Ser Ser
        115


<210> SEQ ID NO 112
<211> LENGTH: 112
<212> TYPE: PRT
<213> ORGANISM: Artificial Sequence
<220> FEATURE:
<223> OTHER INFORMATION: Synthetic Construct
```

<400> SEQUENCE: 112

Asp Ile Val Leu Thr Gln Thr Pro Leu Ser Leu Pro Val Thr Pro Gly
1               5                   10                  15

Glu Pro Ala Ser Ile Ser Cys Arg Ser Ser Gln Arg Leu Leu His Ser
            20                  25                  30

Asp Gly Tyr Thr Tyr Leu Asp Trp Tyr Leu Gln Lys Pro Gly Gln Ser
        35                  40                  45

Pro Gln Leu Leu Ile Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln His
                85                  90                  95

Lys Ala Leu Pro Leu Thr Phe Gly Gly Gly Thr Lys Val Glu Ile Lys
            100                 105                 110

<210> SEQ ID NO 113
<211> LENGTH: 112
<212> TYPE: PRT
<213> ORGANISM: Artificial Sequence
<220> FEATURE:
<223> OTHER INFORMATION: Synthetic Construct

<400> SEQUENCE: 113

Asp Ile Val Met Ile Gln Thr Pro Leu Ser Leu Pro Val Thr Pro Gly
1               5                   10                  15

Glu Pro Ala Ser Ile Ser Cys Arg Ser Ser Gln Arg Leu Leu His Ser
            20                  25                  30

Asp Gly Tyr Thr Tyr Leu Asp Trp Tyr Leu Gln Lys Pro Gly Gln Ser
        35                  40                  45

Pro Gln Leu Leu Ile Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln His
                85                  90                  95

Lys Ala Leu Pro Leu Thr Phe Gly Gly Gly Thr Lys Leu Glu Ile Lys
            100                 105                 110

<210> SEQ ID NO 114
<211> LENGTH: 112
<212> TYPE: PRT
<213> ORGANISM: Artificial Sequence
<220> FEATURE:
<223> OTHER INFORMATION: Synthetic Construct

<400> SEQUENCE: 114

Asp Ile Val Leu Thr Gln Thr Pro Leu Ser Leu Ala Val Ser Pro Gly
1               5                   10                  15

Glu Pro Ala Ser Ile Ser Cys Arg Ser Ser Gln Ser Leu Leu Ala Ser
            20                  25                  30

Asp Gly Tyr Thr Tyr Leu Asp Trp Tyr Leu Gln Lys Pro Gly Gln Ser
        35                  40                  45

Pro Gln Ile Leu Ile Tyr Gly Gly Ser Asn Arg Ala Ser Gly Val Pro
    50                  55                  60

Asp Arg Phe Ser Gly Arg Gly Ser Gly Thr Asp Phe Thr Leu Lys Ile
65                  70                  75                  80

```
Thr Lys Val Glu Ala Glu Asp Val Gly Val Tyr Tyr Cys Leu Gln His
                85                  90                  95

Arg Ala Leu Pro Pro Thr Phe Gly Gln Gly Thr Lys Leu Glu Ile Lys
            100                 105                 110


<210> SEQ ID NO 115
<211> LENGTH: 112
<212> TYPE: PRT
<213> ORGANISM: Artificial Sequence
<220> FEATURE:
<223> OTHER INFORMATION: Synthetic Construct

<400> SEQUENCE: 115

Asp Ile Val Met Ile Gln Thr Pro Leu Ser Leu Pro Val Thr Pro Gly
1               5                   10                  15

Glu Pro Ala Ser Ile Ser Cys Arg Ser Ser Gln Arg Leu Leu His Thr
            20                  25                  30

Asp Gly Tyr Thr Tyr Leu Asp Trp Tyr Leu Gln Lys Pro Gly Gln Ser
        35                  40                  45

Pro Gln Leu Leu Ile Tyr Gly Gly Ser Asn Arg Ala Ser Gly Val Pro
    50                  55                  60

Asp Arg Phe Ser Gly Ser Gly Ser Gly Ser Asp Phe Thr Leu Lys Ile
65                  70                  75                  80

Ser Lys Val Glu Ala Glu Asp Val Gly Val Tyr Tyr Cys Leu Gln His
                85                  90                  95

Lys Ala Leu Pro Leu Thr Phe Gly Gly Gly Thr Lys Leu Glu Ile Lys
            100                 105                 110


<210> SEQ ID NO 116
<211> LENGTH: 112
<212> TYPE: PRT
<213> ORGANISM: Artificial Sequence
<220> FEATURE:
<223> OTHER INFORMATION: Synthetic Construct

<400> SEQUENCE: 116

Asp Ala Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Ala Ser
            20                  25                  30

Asp Gly Tyr Asn Tyr Ile Asp Trp Tyr Leu Gln Arg Pro Gly Gln Ser
        35                  40                  45

Pro Lys Val Leu Ile Tyr Gly Gly Ser Asn Arg Ala Ser Gly Val Pro
    50                  55                  60

Asp Arg Phe Ser Gly Ser Gly Ser Gly Thr Tyr Phe Thr Leu Lys Ile
65                  70                  75                  80

Ser Lys Val Glu Ala Glu Asp Val Gly Phe Tyr Phe Cys Leu Gln His
                85                  90                  95

Arg Ala Leu Pro Pro Thr Phe Gly Gln Gly Thr Lys Leu Glu Ile Lys
            100                 105                 110


<210> SEQ ID NO 117
<211> LENGTH: 112
<212> TYPE: PRT
<213> ORGANISM: Artificial Sequence
<220> FEATURE:
<223> OTHER INFORMATION: Synthetic Construct

<400> SEQUENCE: 117
```

Asp Ile Val Met Ile Gln Asn Pro Leu Ser Leu Pro Val Thr Pro Gly
1 5 10 15

Glu Pro Ala Ser Ile Ser Cys Arg Ser Ser Gln Ser Leu Leu Ala Ser
20 25 30

Asp Gly Tyr Asn Tyr Met Asp Trp Tyr Leu Gln Lys Pro Gly Gln Ser
35 40 45

Pro Lys Val Leu Ile Tyr Gly Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Thr Lys Val Glu Ala Glu Asp Val Gly Ile Tyr Tyr Cys Met Gln His
85 90 95

Lys Val Leu Pro Pro Thr Phe Gly Gln Gly Thr Lys Leu Glu Ile Lys
100 105 110

<210> SEQ ID NO 118
<211> LENGTH: 112
<212> TYPE: PRT
<213> ORGANISM: Artificial Sequence
<220> FEATURE:
<223> OTHER INFORMATION: Synthetic Construct

<400> SEQUENCE: 118

Asp Thr Val Met Thr Gln Ile Pro Leu Ser Leu Ser Val Thr Pro Gly
1 5 10 15

Glu Pro Ala Ser Ile Ser Cys Arg Ser Ser Gln Arg Leu Leu His Thr
20 25 30

Asp Gly Tyr Thr Tyr Leu Asp Trp Tyr His Gln Lys Pro Gly Gln Ser
35 40 45

Pro Gln Leu Leu Ile Tyr Gly Gly Ser Asn Arg Ala Ser Gly Val Pro
50 55 60

Asp Arg Phe Ser Gly Ser Gly Ser Val Thr Asp Phe Thr Leu Lys Ile
65 70 75 80

Ser Lys Met Glu Ala Glu Asp Val Gly Val Tyr Tyr Cys Met Gln His
85 90 95

Lys Ala Leu Pro Pro Thr Phe Gly Gly Gly Thr Lys Leu Glu Ile Lys
100 105 110

<210> SEQ ID NO 119
<211> LENGTH: 112
<212> TYPE: PRT
<213> ORGANISM: Artificial Sequence
<220> FEATURE:
<223> OTHER INFORMATION: Synthetic Construct

<400> SEQUENCE: 119

Asp Ile Val Met Thr Gln Thr Pro Leu Ser Arg Pro Val Thr Pro Gly
1 5 10 15

Glu Pro Ala Ser Ile Ser Cys Arg Ser Ser Gln Ser Leu Leu His Thr
20 25 30

Asp Gly Tyr Thr Tyr Leu Asp Trp Tyr Leu Gln Lys Pro Gly Gln Ser
35 40 45

Pro Gln Leu Leu Ile Tyr Gly Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Lys Val Glu Ala Glu Asp Val Gly Val Tyr Tyr Cys Met Gln His
85 90 95

```
Lys Ala Leu Pro Leu Thr Phe Gly Gly Gly Thr Lys Leu Glu Ile Lys
            100                 105                 110


<210> SEQ ID NO 120
<211> LENGTH: 112
<212> TYPE: PRT
<213> ORGANISM: Artificial Sequence
<220> FEATURE:
<223> OTHER INFORMATION: Synthetic Construct

<400> SEQUENCE: 120

Asp Ile Val Met Ile Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Thr Tyr Val Asp Trp Tyr Leu Gln Lys Pro Gly Gln Ser
        35                  40                  45

Pro Gln Ile Leu Ile Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Thr Asn Val Glu Ala Glu Asp Val Gly Val Tyr Tyr Cys Leu Gln His
                85                  90                  95

Lys Ala Leu Pro Pro Thr Phe Gly Gln Gly Thr Lys Leu Glu Ile Lys
            100                 105                 110


<210> SEQ ID NO 121
<211> LENGTH: 112
<212> TYPE: PRT
<213> ORGANISM: Artificial Sequence
<220> FEATURE:
<223> OTHER INFORMATION: Synthetic Construct

<400> SEQUENCE: 121

Asp Thr Val Met Ser Gln Ile Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asp Gly Tyr Ile Tyr Leu Asp Trp Tyr Leu Gln Lys Pro Gly Gln Ser
        35                  40                  45

Pro Gln Leu Leu Ile Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln His
                85                  90                  95

Lys Ala Leu Pro Leu Thr Phe Gly Gly Gly Thr Lys Leu Glu Ile Lys
            100                 105                 110


<210> SEQ ID NO 122
<211> LENGTH: 112
<212> TYPE: PRT
<213> ORGANISM: Artificial Sequence
<220> FEATURE:
<223> OTHER INFORMATION: Synthetic Construct

<400> SEQUENCE: 122

Asp Ala Val Met Thr Gln Ile Pro Leu Ser Leu Pro Val Thr Pro Gly
1               5                   10                  15
```

```
Glu Pro Ala Ser Ile Ser Cys Arg Ser Ser Gln Ser Leu Leu His Thr
            20                  25                  30

Asp Gly Tyr Thr Tyr Leu Asp Trp Tyr Leu Gln Lys Pro Gly Gln Ser
        35                  40                  45

Pro Gln Leu Leu Ile Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln His
                85                  90                  95

Lys Ala Leu Pro Pro Thr Phe Gly Gly Gly Thr Lys Leu Glu Ile Lys
            100                 105                 110


<210> SEQ ID NO 123
<211> LENGTH: 112
<212> TYPE: PRT
<213> ORGANISM: Artificial Sequence
<220> FEATURE:
<223> OTHER INFORMATION: Synthetic Construct

<400> SEQUENCE: 123

Asp Ile Val Leu Thr Gln Thr Pro Leu Ser Leu Pro Val Thr Pro Gly
1               5                   10                  15

Glu Pro Ala Ser Ile Ser Cys Arg Ser Ser Gln Arg Leu Leu His Ser
            20                  25                  30

Asp Gly Tyr Thr Tyr Met Asp Trp Tyr Leu Gln Lys Pro Gly Gln Ser
        35                  40                  45

Pro Gln Ile Leu Ile Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln His
                85                  90                  95

Lys Ala Leu Pro Pro Thr Phe Gly Gln Gly Thr Lys Leu Glu Ile Lys
            100                 105                 110


<210> SEQ ID NO 124
<211> LENGTH: 112
<212> TYPE: PRT
<213> ORGANISM: Artificial Sequence
<220> FEATURE:
<223> OTHER INFORMATION: Synthetic Construct

<400> SEQUENCE: 124

Asp Ile Glu Leu Thr Gln Thr Pro Leu Ser Arg Pro Val Thr Pro Gly
1               5                   10                  15

Glu Pro Ala Ser Ile Ser Cys Arg Ser Ser Gln Ser Leu Leu His Thr
            20                  25                  30

Asp Gly Tyr Thr Tyr Leu Asp Trp Tyr Leu Gln Lys Pro Gly Gln Ser
        35                  40                  45

Pro Gln Leu Leu Ile Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln His
                85                  90                  95

Lys Ala Leu Pro Leu Thr Phe Gly Gly Gly Thr Lys Leu Glu Ile Lys
            100                 105                 110
```

<210> SEQ ID NO 125
<211> LENGTH: 112
<212> TYPE: PRT
<213> ORGANISM: Artificial Sequence
<220> FEATURE:
<223> OTHER INFORMATION: Synthetic Construct

<400> SEQUENCE: 125

```
Asp Ile Val Met Thr Gln Asn Pro Leu Ser Leu Pro Val Thr Pro Gly
1               5                   10                  15

Glu Pro Ala Ser Ile Ser Cys Arg Ser Ser Gln Ser Leu Leu Ala Thr
            20                  25                  30

Asp Gly Tyr Thr Tyr Leu Asp Trp Tyr Leu Gln Lys Pro Gly Gln Ser
        35                  40                  45

Pro Gln Val Leu Ile Tyr Gly Gly Ser Lys Arg Ala Ser Gly Val Pro
    50                  55                  60

Asp Arg Phe Ser Gly Ser Gly Ser Gly Thr Asp Phe Thr Leu Lys Ile
65                  70                  75                  80

Thr Lys Val Glu Ala Glu Asp Val Gly Ile Tyr Tyr Cys Met Gln His
                85                  90                  95

Lys Ala Leu Pro Pro Thr Phe Gly Gln Gly Thr Lys Leu Glu Ile Lys
            100                 105                 110
```

<210> SEQ ID NO 126
<211> LENGTH: 112
<212> TYPE: PRT
<213> ORGANISM: Artificial Sequence
<220> FEATURE:
<223> OTHER INFORMATION: Synthetic Construct

<400> SEQUENCE: 126

```
Asp Ala Val Met Thr Gln Ile Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asp Gly Tyr Thr Tyr Leu Asp Trp Tyr Leu Gln Lys Pro Gly Gln Ser
        35                  40                  45

Pro Gln Leu Leu Ile Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln His
                85                  90                  95

Lys Ala Leu Pro Leu Thr Phe Gly Gly Gly Thr Arg Leu Glu Ile Lys
            100                 105                 110
```

<210> SEQ ID NO 127
<211> LENGTH: 112
<212> TYPE: PRT
<213> ORGANISM: Artificial Sequence
<220> FEATURE:
<223> OTHER INFORMATION: Synthetic Construct

<400> SEQUENCE: 127

```
Asp Ile Val Met Ile Gln Asn Pro Leu Ser Leu Ser Val Thr Pro Gly
1               5                   10                  15

Glu Pro Ala Ser Ile Ser Cys Arg Ser Ser Gln Arg Leu Leu Ala Ser
            20                  25                  30
```

```
Asp Gly Tyr Thr Tyr Val Asp Trp Tyr Leu Gln Lys Pro Gly Gln Ser
        35                  40                  45

Pro Gln Ile Leu Ile Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln His
                85                  90                  95

Lys Ala Leu Pro Pro Thr Phe Gly Gln Gly Thr Lys Leu Glu Ile Lys
            100                 105                 110


<210> SEQ ID NO 128
<211> LENGTH: 112
<212> TYPE: PRT
<213> ORGANISM: Artificial Sequence
<220> FEATURE:
<223> OTHER INFORMATION: Synthetic Construct

<400> SEQUENCE: 128

Asp Ile Val Met Thr Gln Asn Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asn Arg Tyr Ala Tyr Val Asp Trp Tyr Leu Gln Lys Pro Gly Gln Ser
        35                  40                  45

Pro Gln Ile Leu Val Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Ile Tyr Tyr Cys Met Gln His
                85                  90                  95

Lys Val Leu Pro Pro Thr Phe Gly Gln Gly Thr Lys Leu Glu Ile Lys
            100                 105                 110


<210> SEQ ID NO 129
<211> LENGTH: 112
<212> TYPE: PRT
<213> ORGANISM: Artificial Sequence
<220> FEATURE:
<223> OTHER INFORMATION: Synthetic Construct

<400> SEQUENCE: 129

Asp Ile Val Met Ile Gln Asn Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Thr Tyr Leu Asp Trp Tyr Gln Gln Lys Pro Gly Gln Ala
        35                  40                  45

Pro Gln Leu Leu Ile Tyr Gly Gly Ser Asn Arg Ala Ser Gly Val Pro
    50                  55                  60

Asp Arg Phe Ser Gly Ser Gly Ser Ala Thr Asp Phe Thr Leu Lys Ile
65                  70                  75                  80

Ser Lys Met Glu Ala Glu Asp Val Gly Val Tyr Tyr Cys Met Gln His
                85                  90                  95

Lys Ala Leu Pro Pro Thr Phe Gly Gly Gly Thr Lys Val Glu Ile Lys
            100                 105                 110


<210> SEQ ID NO 130
```

<211> LENGTH: 112
<212> TYPE: PRT
<213> ORGANISM: Artificial Sequence
<220> FEATURE:
<223> OTHER INFORMATION: Synthetic Construct

<400> SEQUENCE: 130

Asp Ile Val Met Ile Gln Asn Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asp Gly Tyr Thr Tyr Leu Asp Trp Tyr Leu Gln Lys Pro Gly Gln Ser
35 40 45

Pro Gln Leu Leu Ile Tyr Gly Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Lys Val Glu Ala Glu Asp Val Gly Val Tyr Tyr Cys Met Gln His
85 90 95

Lys Val Leu Pro Leu Thr Phe Ala Gly Gly Thr Lys Leu Glu Ile Lys
100 105 110

<210> SEQ ID NO 131
<211> LENGTH: 112
<212> TYPE: PRT
<213> ORGANISM: Artificial Sequence
<220> FEATURE:
<223> OTHER INFORMATION: Synthetic Construct

<400> SEQUENCE: 131

Asp Ile Val Met Ile Gln Asn Pro Leu Ser Leu Pro Val Thr Pro Gly
1 5 10 15

Glu Pro Ala Ser Ile Ser Cys Arg Ser Ser Gln Asn Leu Leu Ala Thr
20 25 30

Asp Gly Tyr Thr Tyr Leu Asp Trp Tyr Leu Gln Lys Pro Gly Gln Ser
35 40 45

Pro Gln Val Leu Ile Tyr Gly Gly Ser Lys Arg Ala Ser Gly Val Pro
50 55 60

Asp Arg Phe Ser Gly Ser Gly Ser Gly Thr Asp Phe Thr Leu Lys Ile
65 70 75 80

Ser Lys Val Glu Ala Glu Asp Val Gly Ile Tyr Tyr Cys Leu Gln His
85 90 95

Arg Ala Leu Pro Pro Thr Phe Gly Gln Gly Thr Lys Leu Glu Ile Lys
100 105 110

<210> SEQ ID NO 132
<211> LENGTH: 112
<212> TYPE: PRT
<213> ORGANISM: Artificial Sequence
<220> FEATURE:
<223> OTHER INFORMATION: Synthetic Construct

<400> SEQUENCE: 132

Asp Ile Val Met Ile Gln Asn Pro Leu Ser Leu Ser Val Ser Leu Gly
1 5 10 15

Glu Pro Ala Ser Ile Ser Cys Arg Ser Ser Gln Ser Leu Leu Ala Thr
20 25 30

Asp Gly Tyr Glu Tyr Leu Asp Trp Tyr Leu Gln Lys Pro Gly Gln Ser
35 40 45

Pro Gln Ile Leu Ile Tyr Gly Ala Ser Asn Arg Ala Ser Gly Val Pro
50 55 60

Asp Arg Phe Ser Gly Arg Gly Ser Gly Thr Asp Phe Thr Leu Lys Ile
65 70 75 80

Thr Lys Val Glu Ala Glu Asp Val Gly Val Tyr Tyr Cys Leu Gln His
85 90 95

Lys Ala Leu Pro Pro Thr Phe Gly Gln Gly Thr Lys Leu Glu Ile Lys
100 105 110

<210> SEQ ID NO 133
<211> LENGTH: 112
<212> TYPE: PRT
<213> ORGANISM: Artificial Sequence
<220> FEATURE:
<223> OTHER INFORMATION: Synthetic Construct

<400> SEQUENCE: 133

Asp Ile Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asp Gly Tyr Thr Tyr Leu Asp Trp Tyr Leu Gln Arg Pro Gly Gln Ser
35 40 45

Pro His Leu Leu Ile Tyr Gly Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Lys Val Glu Ala Glu Asp Val Gly Val Tyr Tyr Cys Met Gln His
85 90 95

Lys Val Leu Pro Pro Thr Phe Gly Gln Gly Thr Lys Leu Glu Ile Lys
100 105 110

<210> SEQ ID NO 134
<211> LENGTH: 112
<212> TYPE: PRT
<213> ORGANISM: Artificial Sequence
<220> FEATURE:
<223> OTHER INFORMATION: Synthetic Construct

<400> SEQUENCE: 134

Asp Thr Val Met Ser Gln Ile Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asp Gly Tyr Thr Tyr Met Asp Trp Tyr Leu Gln Lys Pro Gly Gln Ser
35 40 45

Pro Gln Leu Leu Ile Tyr Gly Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Lys Val Glu Ala Glu Asp Val Gly Val Tyr Tyr Cys Met Gln His
85 90 95

Lys Val Leu Pro Pro Thr Phe Gly Gln Gly Thr Arg Leu Glu Ile Lys
100 105 110

<210> SEQ ID NO 135
<211> LENGTH: 112
<212> TYPE: PRT
<213> ORGANISM: Artificial Sequence
<220> FEATURE:
<223> OTHER INFORMATION: Synthetic Construct

<400> SEQUENCE: 135

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Ala Ser
20 25 30

Asp Gly Tyr Asn Tyr Ile Asp Trp Tyr Leu Gln Lys Pro Gly Gln Ser
35 40 45

Pro Gln Leu Leu Ile Tyr Gly Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Leu Gln His
85 90 95

Arg Ala Leu Pro Pro Thr Phe Gly Gln Gly Thr Lys Leu Glu Ile Lys
100 105 110

<210> SEQ ID NO 136
<211> LENGTH: 112
<212> TYPE: PRT
<213> ORGANISM: Artificial Sequence
<220> FEATURE:
<223> OTHER INFORMATION: Synthetic Construct

<400> SEQUENCE: 136

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Ala Ser
20 25 30

Asp Gly Tyr Ile Tyr Ile Asp Trp Tyr Leu Gln Lys Pro Gly Gln Ser
35 40 45

Pro Gln Leu Leu Ile Tyr Gly Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Leu Gln His
85 90 95

Arg Ala Leu Pro Pro Thr Phe Gly Gln Gly Thr Lys Leu Glu Ile Lys
100 105 110

<210> SEQ ID NO 137
<211> LENGTH: 112
<212> TYPE: PRT
<213> ORGANISM: Artificial Sequence
<220> FEATURE:
<223> OTHER INFORMATION: Synthetic Construct

<400> SEQUENCE: 137

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Ala Ser
20 25 30

Asp Gly Tyr Asn Tyr Ile Asp Trp Tyr Leu Gln Lys Pro Gly Gln Ser
35 40 45

Pro Gln Leu Leu Ile Tyr Gly Gly Ser Asn Arg Ala Ser Gly Val Pro
50 55 60

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln His
                85                  90                  95

Lys Ala Leu Pro Pro Thr Phe Gly Gln Gly Thr Lys Leu Glu Ile Lys
            100                 105                 110


<210> SEQ ID NO 138
<211> LENGTH: 112
<212> TYPE: PRT
<213> ORGANISM: Artificial Sequence
<220> FEATURE:
<223> OTHER INFORMATION: Synthetic Construct

<400> SEQUENCE: 138

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Ala Ser
            20                  25                  30

Asp Ala Tyr Asn Tyr Ile Asp Trp Tyr Leu Gln Lys Pro Gly Gln Ser
        35                  40                  45

Pro Gln Leu Leu Ile Tyr Gly Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln His
                85                  90                  95

Arg Ala Leu Pro Pro Thr Phe Gly Gln Gly Thr Lys Leu Glu Ile Lys
            100                 105                 110


<210> SEQ ID NO 139
<211> LENGTH: 112
<212> TYPE: PRT
<213> ORGANISM: Artificial Sequence
<220> FEATURE:
<223> OTHER INFORMATION: Synthetic Construct

<400> SEQUENCE: 139

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Leu Leu Ala Thr
            20                  25                  30

Asp Gly Tyr Thr Tyr Leu Asp Trp Tyr Leu Gln Lys Pro Gly Gln Ser
        35                  40                  45

Pro Gln Leu Leu Ile Tyr Gly Gly Ser Lys Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln His
                85                  90                  95

Arg Ala Leu Pro Pro Thr Phe Gly Gln Gly Thr Lys Leu Glu Ile Lys
            100                 105                 110


<210> SEQ ID NO 140
<211> LENGTH: 112
<212> TYPE: PRT
<213> ORGANISM: Artificial Sequence
<220> FEATURE:
<223> OTHER INFORMATION: Synthetic Construct
```

<400> SEQUENCE: 140

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Ala Thr
20 25 30

Asp Gly Tyr Glu Tyr Leu Asp Trp Tyr Leu Gln Lys Pro Gly Gln Ser
35 40 45

Pro Gln Leu Leu Ile Tyr Gly Ala Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Leu Gln His
85 90 95

Lys Ala Leu Pro Pro Thr Phe Gly Gln Gly Thr Lys Leu Glu Ile Lys
100 105 110

<210> SEQ ID NO 141
<211> LENGTH: 74
<212> TYPE: PRT
<213> ORGANISM: Artificial Sequence
<220> FEATURE:
<223> OTHER INFORMATION: Synthetic Construct

<400> SEQUENCE: 141

Thr Leu Gln Lys Lys Ile Glu Glu Ile Ala Ala Lys Tyr Lys His Ser
1 5 10 15

Val Val Lys Lys Cys Cys Tyr Asp Gly Ala Cys Val Asn Asn Asp Glu
20 25 30

Thr Cys Glu Gln Arg Ala Ala Arg Ile Ser Leu Gly Pro Arg Cys Ile
35 40 45

Lys Ala Phe Thr Glu Cys Cys Val Val Ala Ser Gln Leu Arg Ala Asn
50 55 60

Ile Ser His Lys Asp Met Gln Leu Gly Arg
65 70

<210> SEQ ID NO 142
<211> LENGTH: 330
<212> TYPE: PRT
<213> ORGANISM: Artificial Sequence
<220> FEATURE:
<223> OTHER INFORMATION: Synthetic Construct

<400> SEQUENCE: 142

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 143
<211> LENGTH: 327
<212> TYPE: PRT
<213> ORGANISM: Artificial Sequence
<220> FEATURE:
<223> OTHER INFORMATION: Synthetic Construct

<400> SEQUENCE: 143

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 144
<211> LENGTH: 107
<212> TYPE: PRT
<213> ORGANISM: Artificial Sequence
<220> FEATURE:
<223> OTHER INFORMATION: Synthetic Construct

<400> SEQUENCE: 144

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 145
<211> LENGTH: 23
<212> TYPE: PRT
<213> ORGANISM: Artificial sequence
<220> FEATURE:
<223> OTHER INFORMATION: Synthetic Construct

<400> SEQUENCE: 145

```
Asp Gly Ala Cys Val Asn Asn Asp Glu Thr Cys Glu Gln Arg Ala Ala
1               5                   10                  15
```

-continued

```
Arg Ile Ser Leu Gly Pro Arg
            20


<210> SEQ ID NO 146
<211> LENGTH: 17
<212> TYPE: PRT
<213> ORGANISM: Artificial Sequence
<220> FEATURE:
<223> OTHER INFORMATION: Synthetic Construct

<400> SEQUENCE: 146

Asn Asp Glu Thr Cys Glu Gln Arg Ala Ala Arg Ile Ser Leu Gly Pro
1               5                   10                  15

Arg


<210> SEQ ID NO 147
<211> LENGTH: 10
<212> TYPE: PRT
<213> ORGANISM: Artificial Sequence
<220> FEATURE:
<223> OTHER INFORMATION: Synthetic Construct

<400> SEQUENCE: 147

Asp Glu Thr Cys Glu Gln Arg Ala Ala Arg
1               5                   10
```